United States Patent
Turley et al.

(10) Patent No.: US 10,766,927 B2
(45) Date of Patent: *Sep. 8, 2020

(54) PEPTIDES THAT STIMULATE SUBCUTANEOUS ADIPOGENESIS

(71) Applicant: THE REGENTS OF THE UNIVERSITY OF CALIFORNIA, Oakland, CA (US)

(72) Inventors: Eva A. Turley, London (CA); Seyed Bahram Bahrami, Emeryville, CA (US); Mina J. Bissell, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/089,445

(22) Filed: Nov. 25, 2013

(65) Prior Publication Data

US 2014/0179616 A1    Jun. 26, 2014

Related U.S. Application Data

(60) Provisional application No. 61/729,626, filed on Nov. 25, 2012, provisional application No. 61/778,084, filed on Mar. 12, 2013.

(51) Int. Cl.

| | | |
|---|---|---|
| *C07K 7/08* | (2006.01) | |
| *A61K 38/08* | (2019.01) | |
| *A61K 31/167* | (2006.01) | |
| *A61K 8/64* | (2006.01) | |
| *A61Q 19/08* | (2006.01) | |
| *C07K 14/705* | (2006.01) | |
| *A61K 38/03* | (2006.01) | |
| *A61Q 19/00* | (2006.01) | |
| *C07K 7/06* | (2006.01) | |
| *A61K 38/00* | (2006.01) | |

(52) U.S. Cl.
CPC ............... *C07K 7/08* (2013.01); *A61K 8/64* (2013.01); *A61K 31/167* (2013.01); *A61K 38/03* (2013.01); *A61K 38/08* (2013.01); *A61Q 19/001* (2013.01); *A61Q 19/08* (2013.01); *C07K 7/06* (2013.01); *C07K 14/70596* (2013.01); *A61K 38/00* (2013.01)

(58) Field of Classification Search
USPC ...................................................... 514/18.8
See application file for complete search history.

(56) References Cited

U.S. PATENT DOCUMENTS

| | | | |
|---|---|---|---|
| 6,127,525 A | 10/2000 | Crystal et al. | |
| 6,153,432 A | 11/2000 | Halvorsen et al. | |
| 6,211,149 B1 | 4/2001 | Chesebro et al. | |
| 6,271,344 B1 | 8/2001 | Turley | |
| 6,429,291 B1 | 8/2002 | Turley et al. | |
| 6,709,864 B1 | 3/2004 | Pittenger et al. | |
| 6,864,235 B1 | 3/2005 | Turley et al. | |
| 6,911,429 B2* | 6/2005 | Cruz et al. | 424/185.1 |
| 7,544,661 B2 | 6/2009 | Stupp et al. | |
| 7,576,052 B2 | 8/2009 | Kahn et al. | |
| 8,093,217 B2 | 1/2012 | Toole et al. | |
| 8,715,653 B2 | 5/2014 | Turley et al. | |
| 10,494,402 B2 | 12/2019 | Turley et al. | |
| 2002/0127227 A1 | 9/2002 | Holmes et al. | |
| 2003/0100490 A1 | 5/2003 | Cruz et al. | |
| 2003/0144329 A1 | 7/2003 | Pfahl et al. | |
| 2003/0170755 A1 | 9/2003 | Schmitt et al. | |
| 2003/0223997 A1* | 12/2003 | Challita-Eid | C07K 14/47 424/155.1 |
| 2004/0010812 A1 | 1/2004 | Turley et al. | |
| 2004/0037834 A1 | 2/2004 | Woloski et al. | |
| 2004/0171821 A1 | 9/2004 | Valenzuela et al. | |
| 2004/0229219 A1* | 11/2004 | Gallaher | C07K 14/005 435/5 |
| 2005/0008621 A1 | 1/2005 | Kirkland et al. | |
| 2005/0032064 A1 | 2/2005 | Staels | |
| 2005/0048135 A1 | 3/2005 | Iinuma et al. | |
| 2005/0058646 A1 | 3/2005 | Turley et al. | |
| 2005/0164183 A1 | 7/2005 | Imagawa et al. | |
| 2005/0209145 A1 | 9/2005 | Stupp et al. | |
| 2007/0116669 A1* | 5/2007 | Merzouk | C07K 14/522 424/85.1 |
| 2007/0179085 A1 | 8/2007 | Savani | |
| 2007/0185027 A1 | 8/2007 | Erickson et al. | |
| 2007/0292869 A1* | 12/2007 | Becker et al. | 435/6 |
| 2008/0234183 A1* | 9/2008 | Hallbrink | A61K 51/0448 514/1.1 |
| 2009/0176306 A1 | 7/2009 | Taira et al. | |
| 2009/0298164 A1 | 12/2009 | Cattadoris et al. | |

(Continued)

FOREIGN PATENT DOCUMENTS

| | | |
|---|---|---|
| CA | 2 160 603 C | 4/2003 |
| EP | 0 950 708 A2 | 10/1999 |

(Continued)

OTHER PUBLICATIONS

Genscript peptide modification (Oct. 2007).*

(Continued)

*Primary Examiner* — James H Alstrum-Acevedo
*Assistant Examiner* — Tara L Martinez
(74) *Attorney, Agent, or Firm* — Emily M. Haliday; Weaver Austin Villeneuve & Sampson LLP

(57) ABSTRACT

Peptides of 5 to 14 amino acids in length that stimulate subcutaneous adipogenesis and uses thereof are provided.

26 Claims, 14 Drawing Sheets

Specification includes a Sequence Listing.

(56) References Cited

U.S. PATENT DOCUMENTS

| | | | |
|---|---|---|---|
| 2009/0312746 A1 | 12/2009 | Khouri et al. | |
| 2010/0062000 A1 | 3/2010 | Turley et al. | |
| 2010/0093640 A1 | 4/2010 | Bonte et al. | |
| 2010/0143382 A1* | 6/2010 | Turley et al. | 424/172.1 |
| 2010/0290989 A1 | 11/2010 | Tolg | |
| 2010/0323984 A1 | 12/2010 | Piccirilli et al. | |
| 2011/0236411 A1 | 9/2011 | Scholler et al. | |
| 2011/0288034 A1 | 11/2011 | Chada et al. | |
| 2012/0076810 A1* | 3/2012 | Poland | C07K 14/005 424/186.1 |
| 2013/0224234 A1 | 8/2013 | Nakamura et al. | |
| 2013/0259807 A1 | 10/2013 | Bissell et al. | |
| 2015/0284433 A1 | 10/2015 | Turley et al. | |
| 2018/0230188 A1 | 8/2018 | Turley et al. | |

FOREIGN PATENT DOCUMENTS

| | | |
|---|---|---|
| EP | 1 158 044 A1 | 11/2001 |
| EP | 1 456 187 A1 | 9/2004 |
| EP | 1 696 945 A1 | 9/2006 |
| EP | 2 079 460 A2 | 7/2009 |
| JP | 2000-217576 A | 8/2000 |
| JP | 2000-512484 A | 9/2000 |
| JP | 2004-536819 A | 12/2004 |
| JP | 2005-525371 A | 8/2005 |
| JP | 2007-513174 A | 5/2007 |
| JP | 2010-506893 A | 3/2010 |
| WO | WO 1993/021312 | 10/1993 |
| WO | WO1994016328 * | 7/1994 |
| WO | WO/1997/024111 | 7/1997 |
| WO | WO 97/38098 A1 | 10/1997 |
| WO | WO 99/63080 A1 | 12/1999 |
| WO | WO 00/46348 A1 | 8/2000 |
| WO | WO/2000/044882 | 8/2000 |
| WO | WO 02/100428 A1 | 12/2002 |
| WO | WO/2003/033535 | 4/2003 |
| WO | WO2003033535 * | 4/2003 |
| WO | WO 03/075858 A2 | 9/2003 |
| WO | WO/2005/018552 | 3/2005 |
| WO | WO 2005/056039 A2 | 6/2005 |
| WO | WO 2006/130974 A1 | 12/2006 |
| WO | WO 2008/47061 A2 | 4/2008 |
| WO | WO/2008/140586 | 11/2008 |
| WO | WO 2009/036246 A2 | 3/2009 |
| WO | WO 2009/061130 A2 | 5/2009 |
| WO | WO 2011/150495 | 12/2011 |
| WO | WO/2012/031015 | 3/2012 |
| WO | WO/2014/082042 | 5/2014 |
| WO | WO 2015/184125 A1 | 12/2015 |

OTHER PUBLICATIONS

Genebank CA175473 (Genbank Accession No. CA175473[online]. [retrieved on Jan. 19, 2018]. Retrieved from the Internet: <https://www.ncbi.nlm.nih.gov/protein/CA175473>).*
PCT International Search Report and Written Opinion dated Nov. 7, 2008 issued in PCT/US2007/085453.
PCT International Preliminary Report on Patentability dated May 26, 2009 issued in PCT/US2007/085453.
PCT International Search Report and Written Opinion dated Jan. 4, 2012 issued in PCT/US2011/050054.
PCT International Preliminary Report on Patentability dated Mar. 5, 2013 issued in PCT/US2011/050054.
PCT International Search Report and Written Opinion dated May 26, 2014 issued in PCT/US2013/071719.
PCT Invitation to Pay Additional Fees dated Feb. 3, 2014 issued in PCT/US2013/071719.
Australian Examination Report dated Apr. 23, 2012 issued in AU2007353332.
European Supplemental Search Report dated Mar. 4, 2010 issued in EP07874313.5.
European Examination Report dated Jun. 21, 2010 issued in EP07874313.5.
European Examination Report dated Nov. 15, 2011 issued in EP07874313.5.
European Examination Report dated Sep. 10, 2013 issued in EP07874313.5.
European Partial Search Report dated Feb. 11, 2013 issued in EP12172124.5.
European Extended Search Report dated Jun. 5, 2013 issued in EP12172124.5.
European Examination Report dated Jul. 18, 2014 issued in EP12172124.5.
Extended European Search Report dated Mar. 5, 2014 issued in EP11822599.4.
U.S. Office Action dated Jul. 25, 2012 issued in U.S. Appl. No. 12/515,405.
U.S. Final Office Action dated Apr. 23, 2013 issued in U.S. Appl. No. 12/515,405.
U.S. Notice of Allowance dated Dec. 16, 2013 issued in U.S. Appl. No. 12/515,405.
Adamia et al. (2005) "Hyaluronan and hyaluronan synthases: potential therapeutic targets in cancer.", *Curr Drug Targets Cardiovasc Haematol Disord* 5: 3-14.
Aitken et al. (2001) "Stretch-Induced Bladder Smooth Muscle Cell (SMC) Proliferation is Mediated by RHAMM Dependent Extracellular-Regulated Kinase (erk) Signaling.", *Urology* 57(Supp 6A):109.
Babish et al. (2010) "Antidiabetic Screening of Commercial Botanical Products in 3T3-L1 Adipocytes and db/db Mice" *Journal of Medicinal Foof* 13(3): 535-547.
Bissell (2001) "Chronic liver injury, TGF-beta, and cancer.", *Exp Mol Med* 33:179-190.
Cheon et al. (2002) "beta-Catenin stabilization dysregulates mesenchymal cell proliferation, motility, and invasiveness and causes aggressive fibromatosis and hyperplastic cutaneous wounds.", *Proc. Natl. Acad. Sci.* 99(10): 6973-6978.
Cheung et al. (1999) "Receptor for hyaluronan mediated motility (RHAMM), a hyaladherin that regulates cell responses to growth factors.", *Biochem Soc Trans* 27: 135-142.
Database Geneseq [Online] (Dec. 18, 2003) "RHAMM/Erk 1 competitive binding peptide D5.", XP-002718746, retrieved from EBI accession No. GSP:ADC02454 Database accession No. ADC02454; One Page.
Database Geneseq [Online] (May 19, 2005) "Heparin binding protein associated amino acid sequence, SEQ ID No. 65.", XP-002718747, retrieved from EBI accession No. GSP:ADY52132 Database accession No. ADY52132; One Page.
Database Geneseq [Online] (Feb. 17, 2011) "Structural peptide SEQ ID No. 23563.", XP-002718745, retrieved from EBI accession No. GSP:AJG37689 Database accession No. AJG37689; One Page.
Domaszewska et al. (2006) "Dermal keratinocytes-protective mechanical, biochemical and immune functions related to grafting.", *Ann. Transplnt.* 11(4): 45-52.
Esguerra et al. (2010) "Tubulin derived peptides as optical imaging probes targeting RHAMM" *The Journal of Nuclear Medicine* 51 (Supplement 2):394; Abstract No. 394; Downloaded from Internet http://jnumedmtg.snmjournals.org/cgi/content/meeting_abstract/51/2_MeetingAbstracts/394 on Aug. 14, 2013; 2 pages.
Evanko et al. (Nov. 10, 2007) "Hyaluronan-Dependent Pericellular Matrix" *Adv Drug Deliv Rev.* 59(13): 1351-1365; NIH Public Access Author Manuscript; available in PMC Jan. 3, 2008; 30 pages.
Feldman et al. (1998) "Anti-TNF alpha therapy is useful in rheumatoid arthritis and Crohn's disease: analysis of the mechanism of action predicts utility in other disease." *Transplant. Proc.* 30: 4126-4127.
Fu et al. (2006) "Enhanced wound-healing quality with bone marrow mesenchymal stem cells autografting after skin injury.", *Wound Repair Regen.* 14: 325-335.
Fukumura et al. (2003) "Paracrine regulation of angiogenesis and adipocyte differentiation during vivo adipogenesis.", *Circulation Research* 93(9): E88-E97.
Greiner et al. (2005) "RHAMM/CD168-R3 Peptide Vaccination of HLA-A2+ Patients with Acute Myeloid Leukemia (AML),

(56) References Cited

OTHER PUBLICATIONS

Myelodysplastic Syndrome (MDS) and Multiple Myeloma (MM)." *Blood* 106: Abstract 2781; One Page.
Greiner et al. (Aug. 1, 2005) "Identification and characterization of epitopes of the receptor for hyaluronic acid-mediated motility (RHAMM/CD168) recognized by CD8+ T cells of HLA-A2-positive patients with acute myeloid leukemia" *Blood*, 106(3): 938-945.
Hall et al. (1995) "Overexpression of the hyaluronan receptor RHAMM is transforming and is also required for H-ras transformation.", *Cell* 82: 19-28.
Hall et al. (1996) "pp60(c-src) is required for cell locomotion regulated by the hyaluronanreceptor RHAMM.", *Oncogene* 13: 2213-2224.
Hall et al. (2001) "Fibroblasts require protein kinase C activation to respond to hyaluronan with increased locomotion.", *Matrix Biol* 20: 183-192.
Hardwick et al. (1992) "Molecular cloning of a novel hyaluronan receptor that mediates tumor cell motility.", *J Cell Biol.*, 117(6):1343-1350.
Huang et al. (2004) "MAP kinases and cell migration.", *J Cell Sci* 117: 4619-4628.
Kaya et al. (1997) "Selective suppression of CD44 in keratinocytes of mice bearing an antisense CD44 transgene driven by a tissue-specific promoter disrupts hyaluronate metabolism in the skin and impairs keratinocyte proliferation.", Genes and Development 11(8):996-1007.
Li et al. (2006) "Adult bone-marrow-derived mesenchymal stem cells contribute to wound healing of skin appendages.", *Cell Tissue Res*, 326(3): 725-736.
Lovvorn et al. (1998) "Hyaluronan receptor expression increases in fetal excisional skin wounds and correlates with fibroplasia.", *J Pediatr Surg* 33: 1062-1069.
Mansilla et al. (2006) "Bloodstream cells phenotypically identical to human mesenchymal bone marrow stem cells circulate in large amounts under the influence of acute large skin damage: new evidence for their use in regenerative medicine.", *Transplant Proc.* 38: 967-969.
Mestas et al. (2004) "Of Mice and Not Men: Differences between Mouse and Human Immunology" *Journal of Immunology* 172, pp. 2731-2738.
Moreno-Navarrete et al. (2012) "Adipocyte Differentiation" *Adipose Tissue Biology Chapter 2*, 23 Pages, DOI 10.1007/978-1-4614-0965-6_2.
Mummert et al. (2000) "Development of a Peptide Inhibitor of Hyaluronan-Mediated Leukocyte Trafficking", *The Journal of Experimental Medicine* 192(6): 769-779.
Nedvetzki et al. (2004) "RHAMM, a receptor for hyaluronan-mediated motility, compensates for CD44 in inflamed CD44-knockout mice: A different interpretation of redundancy.", *Proc. Natl. Acad. Sci. USA*, 101:18081-18086.
Nickel (2005) "Unconventional secretory routes: direct protein export across the plasma membrane of mammalian cells.", *Traffic* 6:607-614.
Niemelä et al. (2008) "Adipose Tissue and Adipocyte Differentiation: Molecular and Cellular Aspects and Tissue Engineering Applications" *Topics in Tissue Engineering*, vol. 4. Eds. N Asham makhi, R Reis, & F Chiellini 26 Pages.
Park et al. (2000) "The influence of the microenvironment on the malignant phenotype.", *Mol Med Today* 6: 324-329.
Peer et al. (2004) "Tumor-Targeted Hyaluronan Nanoliposomes Increase the Antitumor Activity of Liposomal Doxorubicin in Syngeneic and Human Xenograft Mouse Tumor Models" *Neoplasia* 6(4): 343-353.
Providence et al. (2004) "PAI-1 expression is required for epithelial cell migration in two distinct phases of in vitro wound repair.", *J Cell Physiol* 200: 297-308.
Reid et al. (2004) "The future of wound healing: pursuing surgical models in transgenic and knockout mice.", *J Am Coll Surg* 199: 578-585.
Samuel et al. (1993) "TGF-beta 1 stimulation of cell locomotion utilizes the hyaluronan receptor RHAMM and hyaluronan.", *J Cell Biol* 123: 749-758.
Savani et al. (1995) "Migration of bovine aortic smooth muscle cells after wounding injury. The role of hyaluronan and RHAMM.", *J Clin Invest* 95: 1158-1168.
Schmits et al. (1997) "CD44 regulates hematopoietic progenitor distribution, granuloma formation, and tumorigenicity.", *Blood* 90: 2217-2233.
Sequence Listing for WO/2011/150495 (PCT/CA2011/000613) published on Dec. 8, 2011; 16 Pages.
Shumakov (2003) "Mesenchymal bone marrow stem cells more effectively stimulate regeneration of deep burn wounds than embryonic fibroblasts.", *Bull Exp Biol Med* 136(2): 192-195.
Tammi et al. (2002) "Hyaluronan and homeostasis: a balancing act.", *J Biol Chem* 277: 4581-4584.
Tolg et al. (2003) "Genetic deletion of receptor for hyaluronan-mediated motility (Rhamm) attenuates the formation of aggressive fibromatosis (desmoid tumor)", *Oncogene* 22:6873-6882.
Tolg et al. (2006) "Rhamm -/- fiibroblasts are defective in CD44-mediated ERK1, 2 motogenic signaling, leading to defective skin wound repair", *J Cell Biol* 175(6):1017-1028.
Tolg et al. (Oct. 2012) "A RHAMM Mimetic Peptide Blocks Hyaluronan Signaling and Reduces Inflammation and Fibrogenesis in Excisional Skin Wounds", *The American Journal of Pathology* 181(4): 1250-1270; With supplemental Figures 1-5 and supplemental Table S1; Total 27 pages.
Toole (2004) "Hyaluronan: from extracellular glue to pericellular cue.", *Nat Rev Cancer* 4:528-539.
Tufveson et al. (1993) "New Immunosuppressants: Testing and Development in Animal Models and the Clinic: with Special Reference to DSG", *Immunological Reviews* 136(1): 99-109.
Turley (1982) "Purification of a hyaluronate-binding protein fraction that modifies cell social behavior.", *Biochem Biophys Res Commun* 108: 1016-1024.
Turley et al. (2002) "Signaling properties of hyaluronan receptors.", *J Biol Chem* 277(7): 4589-4592.
Turley et al. (Jan. 1993) "Expression and Function of a Receptor for Hyaluronan-Mediated Motility on Normal and Malignant B Lymphocytes", *Blood* 81(2): 446-453.
Yang et al. (1993) "Identification of Two Hyaluronan-binding Domains in the Hyaluronan Receptor RHAMM", *The Journal of Biological Chemistry* 268(12): 8617-8623.
Zhang et al. (1998) "The hyaluronan receptor RHAMM regulates extracellular-regulated kinase.", *J Biol Chem* 273:11342-11348.
Ziebell et al. (2004) "Interactions of peptide mimics of hyaluronic acid with the receptor for hyaluronan mediated motility (RHAMM)", *Journal of Computer-Aided Molecular Design* 18(10): 597-614.
Canadian Examination Report dated Aug. 5, 2014 issued in CA 2,670,320.
European Office Action dated Feb. 25, 2015 issued in EP 11 822 599.4.
Assmann et al. (1999) "The intracellular hyaluronan receptor RHAMM/IHABP interacts with microtubules and actin filaments," *Journal of Cell Science* 112: 3943-3954.
Choi et al. (2003) "The Role of Ghrelin and Growth Hormone Secretagogues Receptor on Rat Adipogenesis," *Endocrinology* 144(3): 754-759.
Maxwell et al. (2003) "RHAMM is a Centrosomal Protein That Interacts with Dynein and Maintains Spindle Pole Stability," *Molecular Biology of the Cell* 14: 2262-2276.
Savani et al. (2000) "A Role for Hyaluronan in Macrophage Accumulation and Collagen Deposition after Bleomycin-Induced Lung Injury," *Am. J. Respir. Cell Mol. Biol.* 23: 475-484.
Tschöp et al. (2000) "Ghrelin induces adiposity in rodents," *Nature* 407(6806): 908-913.
U.S. Office Action (Restriction Requirement) dated Mar. 15, 2016 issued in U.S. Appl. No. 14/646,298.
U.S. Appl. No. 14/263,897, filed Apr. 28, 2014, Turley et al.
U.S. Appl. No. 14/646,298, filed May 20, 2015, Turley et al.
U.S. Office Action dated Mar. 31, 2015 issued in U.S. Appl. No. 13/818,641.

(56) References Cited

OTHER PUBLICATIONS

U.S. Preliminary Amendment dated Nov. 2, 2015 in U.S. Appl. No. 14/646,298.
Canadian Examination Report dated Jul. 8, 2015 issued in CA 2,670,320.
European Examination Report dated Jul. 22, 2015 issued in EP 07 874 313.5.
Japanese Office Action dated Aug. 3, 2015 issued in JP2013-527285.
PCT International Preliminary Report on Patentability dated Jun. 4, 2015 issued in PCT/US2013/071719.
U.S. Office Action dated Jun. 9, 2016 in U.S. Appl. No. 14/646,298.
Canadian Examination Report dated Jun. 28, 2016 issued in CA 2,670,320.
European letter to reply dated Aug. 23, 2016 to Communication pursuant to Article 94(3) EPC dated Feb. 23, 2016 in EP 07 874 313.5.
European Office Action dated Jun. 23, 2016 issued in EP 13 802 811.3.
Yang et al. (1994) "Identification of a common hyaluronan binding motif in the hyaluronan binding proteins RHAMM, CD44 and link protein," *The EMBO Journal*, 13(2):286-296.
Yusufoglu et al. (Dec. 2008) "Bioinspired synthesis of self-assembled calcium phosphate nanocomposites using block copolymer-peptide conjugates," *J. Mater. Res.*, 23(12):3196-3212.
U.S. Final Office Action dated Jan. 13, 2017 in U.S. Appl. No. 14/646,298.
European Communication dated Oct. 27, 2016 issued in EP 07 874 313.5.
European response to the communication pursuant to Article 94(3) EPC dated Jun. 23, 2016 in EP 13 802 811.3 dated Dec. 30, 2016.
Chinese Office Action dated Aug. 3, 2017 issued in CN 201380061413.4.
Japanese Office Action dated Aug. 8, 2017 issued in JP 2015-544173.
Assmann et al. (1998) "The human hyaluronan receptor RHAMM is expressed as an intracellular protein in breast cancer cells," *Journal of Cell Science*, 111(12):1685-94.
U.S. Office Action dated Jan. 8, 2018 in U.S. Appl. No. 14/646,298.
U.S. Office Action dated Jan. 2, 2019 in U.S. Appl. No. 15/313,538.
Israel Office Action dated Aug. 15, 2018 issued in IL 239008.
PCT International Search Report and Written Opinion dated Aug. 24, 2015 issued in PCT/US2015/032952.
PCT International Preliminary Report on Patentability dated Nov. 29, 2016 issued in PCT/US2015/032952.
GeneBank Accession No. ARB15206 [Online] (retrieved on Oct. 29, 2018) "hypothetical protein Ccr32_gp288 [Caulobacter phage Ccr32]—Protein—NCBI]", Retrieved from the Internet: https://www.ncbi.nlm.nih.gov/protein/arb15206, 1 Page.
Bost et al. (2005) "The extracellular signal-regulated kinase isoform ERK1 is specifically required for in vitro and in vivo adipogenesis." *Diabetes*, 54(2):402-11.
Ji et al. (2013) "Inhibition of adipogenesis in 3T3-L1 cells and suppression of abdominal fat accumulation in high-fat diet-feeding C57BL/6J mice after downregulation of hyaluronic acid" *Int. J. Obes. (Lond.)*, 1035-1043.
Kang et al. (2013) "Hyaluronan accumulates with high-fat feeding and contributes to insulin resistance." *Diabetes*, 62(6):1888-96.
Kim et al. (2014) "Adipose-derived stem cell-containing hyaluronic acid/alginate hydrogel improves vocal fold wound healing." *Laryngoscope*, 124(3):E64-72.
Lee et al. (2010) "A functional role for the p62-ERK1 axis in the control of energy homeostasis and adipogenesis." *EMBO Rep.*, 11(3):226-32.
Liu et al. (2012) "ANKRD26 and its Interacting Partners TRIO, GPS2, HMMR and DIPA Regulate Adipogenesis in 3T3-L1 Cells" *PloS One*, 7(5):e38130 [10 pages].
Maxwell et al. (2008) "Cell-surface and mitotic-spindle RHAMM: moonlighting or dual oncogenic functions?" *J. Cell. Sci.* 121(Pt 7):925-32.
Piccinno et al. (2013) "Adipose stromal/stem cells assist fat transplantation reducing necrosis and increasing graft performance" Apoptosis, 18(10):1274-89.
Shoham et al. (2013) "The mechanics of hyaluronic acid/adipic acid dihydrazide hydrogel: towards developing a vessel for delivery of preadipocytes to native tissues." *J. Mech. Behav. Biomed. Mater.*, 28:320-31.
Tolg et al. (2010) "RHAMM Promotes Interphase Microtubule Instability and Mitotic Spindle Integrity through MEK1/ERK1/2 Activity" *J. Biol. Chem.*, 285(34):26461-74.
Veiseh et al. (2014) "Cellular heterogeneity profiling by hyaluronan probes reveals an invasive but slow-growing breast tumor subset" *Proc. Natl. Acad. Sci. U S A.*, 111(17):E1731-9.
Wang et al. (2014) "Hyperglycemia Diverts Dividing Osteoblastic Precursor Cells to an Adipogenic Pathway and Induces Synthesis of a Hyaluronan Matrix That is Adhesive for Monocytes" *J. Biol. Chem.*, 289(16):11410-20.
U.S. Office Action dated Nov. 8, 2018 in U.S. Appl. No. 14/646,298.
U.S. Notice of Allowance dated Jul. 17, 2019 in U.S. Appl. No. 14/646,298.
U.S. Final Office Action dated Oct. 9, 2019 in U.S. Appl. No. 15/313,538.
GenBank "hypothetical protein TRFO_31011 [Tritrichomonas foetus]" (Oct. 25, 2016), Retrieved from the Internet: <https://www.ncbi.nlm.nih.gov/protein/OHT01994.1?report=genbank&log$=protalign&blast_rank=1&RID=RZ6WU MN2015 >OHT01994.1, 1 page.
Uni ProtKB—A0A061F9Q4 "TCM_033298 Uncharacterized protein isoform 3" (Sep. 3, 2014), Retrieved from the Internet: <https://www.uniprot.org/uniprot/A0A061F9Q4> AOA061F9Q4; intergrated into UniProt Sep. 3, 2014), 4 pages.
European Examination Report dated Feb. 23, 2016 issued in EP 07 874 313.5.

\* cited by examiner

Peptide B sequence: K L K D E N S Q L K S E V S K (SEQ ID NO:2)
Fragment A: L K S E V S K (SEQ ID NO:42)
Fragment C: S Q L K S E V S K (SEQ ID NO:44)

Peptide 15-1 S T M M S R S H K T R S H H V (SEQ ID NO:1)
Fragment B: S T M M S R S H K (SEQ ID NO:62)

US 10,766,927 B2

PEPTIDES THAT STIMULATE SUBCUTANEOUS ADIPOGENESIS

REFERENCE TO RELATED APPLICATIONS

This application claims the benefit of U.S. Provisional Application Serial Nos. 61/778,084, filed on Mar. 12, 2013, and 61/729,626, filed on Nov. 25, 2012. The entire contents of the above applications are hereby incorporated by reference.

STATEMENT OF GOVERNMENTAL SUPPORT

This invention was made with government support under Agreement No. LB09005060 and Contract No. DE-AC02-05CH11231 awarded by the Department of Energy. The government has certain rights in the invention.

FIELD OF THE INVENTION

The present invention generally relates to peptides for stimulating subcutaneous adipogenesis. The invention also relates to pharmaceutical and cosmetic compositions containing such peptides, and to various methods of using such peptides and compositions to reduce scarring, improve the appearance of skin, improve tissue volume, smooth skin, recruit stem cells to formation of subcutaneous fat, reconstruct tissue, and reduce heel pain.

BACKGROUND

RHAMM is an hyaluronan (HA)-binding protein that is either poorly expressed or not expressed in most normal adult tissues but is highly expressed in aggressive human tumors (Adamia et al. (2005) Curr. Drug Targets Cardiovasc. Haematol. Disord., 5: 3-14; Tammi et al. (2002) J. Biol. Chem. 277: 4581-4584; Toole (2004) Nat. Rev. Cancer, 4: 528-539). RHAMM (gene name HMMR) is the Receptor for Hyaluronic Acid Mediated Motility, also known as CD168. RHAMM is a non-integral cell surface protein (CD168) and an intracellular hyaluronan binding protein. Analyses of animal models suggest roles for RHAMM in tumorigenesis and in other disease processes such as arthritis, consistent with its well-documented in vitro functions in cell migration and proliferation and apoptosis (Turley et al. (2002) J. Biol. Chem., 277: 4589-4592). Although cell migration and proliferation and apoptosis are essential functions for morphogenesis and tissue homeostasis, genetic deletion of RHAMM does not appear to affect embryogenesis or adult homeostasis (Tolg et al. (2003) Oncogene 22: 6873-6882). To date, a primary physiological function for RHAMM has remained elusive.

RHAMM was originally isolated from subconfluent migrating fibroblasts in vitro (Turley (1982) Biochem. Biophys. Res. Commun. 108: 1016-1024) and subsequently cloned from mesenchymal cells (see, e.g., Hardwick et al. (1992) J. Cell Biol., 117: 1343-1350). Since antibodies prepared against a shed form of RHAMM blocked HA-stimulated-fibroblast motility, RHAMM was originally described as a cell surface protein that can transduce motogenic signaling pathways in culture (Turley et al. (2002) J. Biol. Chem. 277: 4589-4592). However, HA-bound RHAMM was later detected in intracellular compartments such as the actin and microtubule cytoskeletons, nucleus and cytoplasm (Adamia et al. (2005) Curr. Drug Targets Cardiovasc. Haematol. Disord., 5: 3-14). More recently, RHAMM has been shown to decorate centrosomes and mitotic spindles. RHAMM appears to be required for mitotic spindle formation in culture and acts on the BRCA1/BARD1 pathway to regulate mitotic spindle integrity (Joukov et al. (2006) Cancer Cell, 127: 539-52). Collectively, these results suggest that RHAMM may have both extracellular and intracellular functions, (Nickel (2005) Traffic 6: 607-614; Samuel et al. (1993) J. Cell Biol., 123: 749-758; Zhang et al. (1998) J. Biol. Chem., 273: 11342-11348) thus resembling a group of proteins including epimorphin/syntaxin-2, and autocrine motility factor/phosphoglucose isomerase that are also found at the cell surface where they transmit signals across the cell membrane even though, like RHAMM, they lack both Golgi-ER export peptides and membrane spanning sequences (Nickel (2005) Traffic 6: 607-614).

Although the intracellular versus extracellular functions of RHAMM have not yet been clearly dissected, accumulating data suggest that both forms may contribute to mesenchymal phenotypes, at least during disease. For example, RHAMM expression in culture is increased in transformed fibroblasts by fibrogenic cytokines such as TGF-β (Samuel et al. (1993) J. Cell Biol., 123: 749-758). Cell surface RHAMM is required for activation through fibrogenic cytokines such as PDGF (Zhang et al. (1998) J. Biol. Chem., 273: 11342-11348). It has also been demonstrated that RHAMM expression is high in clinically aggressive mesenchymal tumors (fibromatoses or desmoid tumors) (see, e.g., Tolg et al. (2003) Oncogene 22: 6873-6882). In a mouse model susceptible to desmoid and upper intestinal tract tumors, genetic deletion of RHAMM strongly reduces desmoid initiation and invasion but not upper intestinal tract tumors. Fibroproliferative processes such as aggressive fibromatosis resemble proliferative/migratory stages of wound healing (Cheon et al. (2002) Proc. Natl. Acad. Sci. USA, 99: 6973-6978). Furthermore, the expression of RHAMM is modulated during wounding (Lovvorn et al. (1998) J. Pediatr. Surg., 33: 1062-1069; discussion 1069-1070).

It has been found that factors that regulate fibroblast function play dual roles in wound repair and tumorigenesis (Bissell (2001) Exp. Mol. Med., 33: 179-190; Park et al. (2000) Mol. Med. Today, 6: 324-329) and mesenchymal stem cell trafficking/differentiation into wound sites has become a topic of study (see, e.g., Fu et al. (2006) Wound Repair Regen., 14: 325-35; Mansilla et al. (2006) Transplant Proc. 38: 967-969; Shumakov (2003) Bull. Exp. Biol. Med., 136: 192-195). Mesenchymal stem cells and resident fibroblasts in wounds have immune-modulatory functions that affect the timing and extent of fibrosis during wound repair (Domaszewska and Oszewski (2006) Ann. Transplnt. 11: 45-52).

Genetic loss of RHAMM or blocking RHAMM function using peptides mimicking its hyaluronan binding sequence or antibodies to this sequence have been shown to promote subcutaneous adipogenesis. One such peptide (STMMSR-SHKTRSHHV (SEQ ID NO: 1), P-1 peptide, also referred to herein as peptide P15-1) isolated from a random phage library has been shown to bind to hyaluronan, is adipogenic and resembles the hyaluronan binding region of RHAMM, a mesenchymal factor involved in wound repair. Another peptide, peptide B (KLKDENSQLKSEVSK (SEQ ID NO: 2)), which contains several key residues required for an interaction of RHAMM with HA, is strongly adipogenic. It was reported in PCT Publication No. WO 2008/140586 that RHAMM displays an effect in modulation of adipose tissue development. In particular, histology analysis of tissue sections through unwounded skin of RHAMM −/− mice showed that the subcutaneous layer of fat was two to three times thicker than in wild-type littermate skin and fibroblasts grown from RHAMM −/− wounds incorporated high levels of fat droplets and reduced smooth muscle actin. Furthermore, RHAMM −/− dermal fibroblasts converted to adipocytes when grown in adipogenic medium. In contrast fibroblasts grown from litter matched wild-type wounds did not exhibit fat droplets, and expressed abundant smooth muscle actin. RHAMM-rescued dermal fibroblasts do not undergo adipogenic conversion when grown in adipogenic medium. Conversely, image analysis of RHAMM −/− mice showed that they have significantly less visceral fat and a lower bone density than wild-type litter mates. These data were said to indicate that RHAMM has a differential effect on visceral vs. subcutaneous adipogenesis.

It is also believed that RHAMM is selective in its regulation of subcutaneous vs. visceral fat, and that this regulation is associated with effects on bone marrow stem cells since bone density provides a measure of stem cell activity. This indicates that RHAMM affects subcutaneous fat deposition through its ability to regulate mesenchymal stem cell differentiation, a conclusion substantiated by the effect of RHAMM loss on another mesenchymal stem cell type, myofibroblasts. Furthermore, hyaluronan/RHAMM interactions play a role in this effect on mesenchymal differentiation since HA binding peptides also promote adipogenesis. In addition to these in vivo effects, RHAMM −/− dermal fibroblasts spontaneously develop into adipocytes when cultures become crowded while wild type dermal fibroblasts do not.

SUMMARY

An aspect of the present invention is directed to a peptide for stimulating subcutaneous adipogenesis, wherein the peptide has a length of 6 to 14 amino acids and comprises a motif having the sequence: $X^1$-$X^2$-$X^3$-$X^4$-$X^5$-$X^6$ wherein at least one of $X^1$ and $X^6$ is a positively charged amino acid; the other of $X^1$ and $X^6$ is a positively charged amino acid, leucine (L), or alanine (A); $X^2$ is serine (S), glutamine (Q), alanine (A), glutamate (E), asparagine (N), proline (P), cysteine (C), lysine (K), aspartate (D), tryptophan (W), methionine (M), or threonine (T); $X^3$ is a negatively charged amino acid, alanine (A), glutamine (Q), serine (S), lysine (K), asparagine (N), or threonine (T); $X^4$ is isoleucine (I), valine (V), leucine (L), asparagine (N), alanine (A), serine (S), proline (P), threonine (T), or glutamine (Q); and $X^5$ is serine (S), aspartate (D), threonine (T), leucine (L), alanine (A), phenylalanine (F), glutamate (E), asparagine (N), glycine (G), arginine (R), glutamine (Q), histidine (H), or isoleucine (I); provided that $X^2$ and $X^5$ are not both glutamine (Q) and provided that when $X^1$ is arginine (R), $X^3$ is not lysine (K). Preferably, the peptide is KSEVSK (SEQ ID NO: 3), KQEVSK (SEQ ID NO: 4), KQEVDK (SEQ ID NO: 5), KQENTK (SEQ ID NO: 6), KSEVLK (SEQ ID NO: 7), KQDVSK (SEQ ID NO: 8), KQELDR (SEQ ID NO: 9), LEEIFK (SEQ ID NO: 10), LSELEK (SEQ ID NO: 11), KSEISK (SEQ ID NO: 12), KNEVSK (SEQ ID NO: 13), KSEVTK (SEQ ID NO: 14), KSEVNK (SEQ ID NO: 15), KSDVSK (SEQ ID NO: 16), KSQVSK (SEQ ID NO: 17), KPEVSK (SEQ ID NO: 18), KSEVGK (SEQ ID NO: 19), KSDSSK (SEQ ID NO: 20), KSSPSK (SEQ ID NO: 21), KSEASK (SEQ ID NO: 22), KSELRK (SEQ ID NO:23), KCEVSK (SEQ ID NO: 24), KSKPSK (SEQ ID NO: 25), KKEVSK (SEQ ID NO: 26), KEEVSK (SEQ ID NO: 27), KSETSK (SEQ ID NO: 28), KSNVSK (SEQ ID NO: 29), KDEVSK (SEQ ID NO: 30), KSEVEK (SEQ ID NO: 31), KSAVSK (SEQ ID NO: 32), KWEVSK (SEQ ID NO: 33), KMEVSK (SEQ ID NO: 34), KSEVQK (SEQ ID NO: 35), KSEVHK (SEQ ID NO: 36), KSSVSK (SEQ ID NO: 37), ASEVSK (SEQ ID NO: 38), KAEVSK (SEQ ID NO: 39), KSEVAK (SEQ ID NO: 40), KSEVSA (SEQ ID NO: 41), LKSEVSK (SEQ ID NO: 42), QLKSEVSK (SEQ ID NO: 43), SQLKSEVSK (SEQ ID NO: 44), NSQLKSEVSK (SEQ ID NO: 45), ENSQLKSEVSK (SEQ ID NO: 46), DENSQLKSEVSK (SEQ ID NO: 47), KDENSQLKSEVSK (SEQ ID NO: 48), or LKDENSQLKSEVSK (SEQ ID NO: 49).

Another aspect of the invention is directed to a peptide for stimulating subcutaneous adipogenesis, wherein the peptide has a length of 5 to 14 amino acids and comprises a motif having the sequence: $X^1$-$X^2$-$X^3$-$X^4$-$X^5$-$X^6$ wherein at least one of $X^1$ and $X^6$ is a positively charged amino acid; the other of $X^1$ and $X^6$ is a positively charged amino acid, leucine (L) or a conservative substitution therefor, alanine (A) or a conservative substitution therefor, or absent; and $X^2$-$X^3$-$X^4$-$X^5$ is an amino acid sequence having at least 50% sequence identity with the amino acid sequence SEVS (SEQ ID NO: 50) and having a length of 4 to 8 amino acids.

Yet another aspect of the invention is directed to a peptide for stimulating subcutaneous adipogenesis, wherein the peptide has a length of 6 to 13 amino acids and comprises a motif having the sequence: $X^1$—$X^2$-$X^3$-$X^4$-$X^5$-$X^6$ wherein $X^1$ is serine (S) or a conservative substitution therefor; $X^2$ is a hydrophobic amino acid; $X^3$ is any amino acid; $X^4$ is a hydrophobic amino acid; $X^5$ is serine (S), arginine (R), or a conservative substitution therefor; and $X^6$ is a charged amino acid; provided that $X^1$, $X^2$ and $X^4$ are not all glycine (G) and provided that $X^1$ is not glutamine (Q).

Preferably, the peptide is STMMSR (SEQ ID NO: 51), SIMMSR (SEQ ID NO: 52), STLMSR (SEQ ID NO: 53), STVMSR (SEQ ID NO: 54), STGLSR (SEQ ID NO: 55), STTMSR (SEQ ID NO: 56), STRMSR (SEQ ID NO: 57), STLMRR (SEQ ID NO: 58), STPVSR (SEQ ID NO: 59), STMMSRS (SEQ ID NO: 60), STMMSRSH (SEQ ID NO: 61), STMMSRSHK (SEQ ID NO: 62), STMMSRSHKT (SEQ ID NO: 63), STMMSRSHKTR (SEQ ID NO: 64), STMMSRSHKTRS (SEQ ID NO: 65), or STMMSRSHK-TRSH (SEQ ID NO: 66).

Another aspect of the present invention is directed to a peptide for stimulating subcutaneous adipogenesis, wherein the peptide has a length of 6 to 13 amino acids and comprises a motif having the sequence: $X^1$-$X^2$-$X^3$-$X^4$-$X^5$-$X^6$-$X^5$-$X^6$ wherein $X^1$ is serine (S) or a conservative substitution therefor; $X^6$ is a charged amino acid; and $X^2$-$X^3$-$X^4$-$X^5$ is an amino acid sequence having at least 50% sequence identity with the amino acid sequence TMMS (SEQ ID NO: 67) and having a length of 2 to 8 amino acids.

A further aspect of the invention is directed to a pharmaceutical or cosmetic composition comprising any one or more of the above peptides and a pharmaceutically or cosmetically acceptable carrier.

Yet another aspect of the invention is directed to a method of reducing scarring comprising administering any one or more of the above peptides or the composition to a subject in an amount sufficient to reduce the area of scarring or improve the appearance of a scarred area.

An aspect of the invention is directed to a method of improving the appearance of skin comprising administering any one or more of the above peptides or the composition to a subject in an amount sufficient to improve the appearance of skin in an area of a subject.

Another aspect of the invention is directed to a method of improving tissue volume in an area of a subject, said method comprising administering any one or more of the above peptides or the composition to the subject in an amount sufficient to increase the tissue volume in the area.

Yet another aspect of the invention is directed to a method of smoothing skin in an area of a subject comprising administering any one or more of the above peptides or the composition to the subject in an amount sufficient to smooth skin in the area.

A further aspect of the invention is directed to a method of recruiting stem cells to formation of subcutaneous fat in a subject, the method comprising administering any one or more of the above peptides or the composition to the subject in an amount sufficient to recruit stem cells to the formation of subcutaneous fat in the subject.

Another aspect of the invention is directed to a method of reconstructing tissue of a subject comprising administering any one or more of the above peptides or the composition to the tissue of the subject in an amount sufficient to increase the volume of the tissue during or after a tissue reconstruction procedure.

Yet another aspect of the invention is directed to a method of reducing heel pain in a subject comprising administering any one or more of the above peptides or the composition to the subject in an amount sufficient to reduce heel pain in the subject during walking.

Definitions

The term "peptide" as used herein refers to a polymer of amino acid residues typically ranging in length from about 5 to about 14 amino acids. The amino acid residues of the peptide can be "L-form" amino acid residues, "D" amino acid residues, or a combination thereof. L-, D-, or β-amino acid versions of the peptide sequence as well as retro, inverso, and retro-inverso isoforms are included. "β-peptides" are comprised of "β amino acids", which have their amino group bonded to the β carbon rather than the α-carbon as in the 20 standard biological amino acids.

The terms "standard" and "natural" as applied to peptides herein refer to peptides constructed only from the standard naturally-occurring amino acids: alanine (Ala, A), cysteine (Cys, C), aspartate (Asp, D), glutamate (Glu, E), phenylalanine (Phe, F), glycine (Gly, G), histidine (His, H), isoleucine (Ile, I), lysine (Lys, K), leucine (Leu, L), methionine (Met, M), asparagine (Asn, N), proline (Pro, P), glutamine (Gln, Q), arginine (Arg, R), serine (Ser, S), threonine (Thr, T), valine (Val, V), tryptophan (Trp, W), and tyrosine (Tyr, Y). A peptide of the invention "corresponds" to a natural peptide if it elicits a biological activity (e.g., adipogenic activity) related to the biological activity and/or specificity of the naturally occurring peptide. The elicited activity may be the same as, greater than or less than that of the natural peptide.

The terms "non-standard," and "non-natural," and "analogue" as applied to peptides herein refer to peptides which contain one or more amino acids which are not standard amino acids and/or which are not naturally-occurring amino acids. A skilled artisan would be familiar such non-standard and non-naturally occurring amino acids and would be able to select suitable non-standard and non-naturally occurring amino acids for use in the peptides of the present invention. Amino acid analogues include amino acids that occur in nature but which are non-standard (e.g., norvaline, norleucine), as well as synthetic amino acids that do not occur in nature. For example, various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, and the like. These modified amino acids are illustrative and not intended to be limiting.

The term "conservative substitution" is used to refer to an amino acid substitution that does not substantially alter the activity (e.g., adipogenic activity and/or specificity) of the peptide. Conventional conservative amino acid substitutions involve substituting one amino acid for another amino acid with similar structure and chemical properties (e.g., charge or hydrophobicity). Such conventional substitutions include, but are not limited to, the following: 1) glycine (G)/alanine (A), 2) arginine (R)/lysine (K), 3) serine (S)/threonine (T)/tyrosine (Y), 4) leucine (L)/isoleucine (I)/valine (V), 5) aspartic acid (D)/glutamic acid (E), 6) glutamine (Q)/asparagine (N), and 7) phenylalanine (F)/tyrosine (Y)/tryptophan (W). Other functional conservative substitutions include, but are not limited to 8) glycine (G)/alanine (A)/proline (P), 9) tyrosine (Y)/histidine (H), 10) arginine (R)/lysine (K)/histidine (H), 11) serine (S)/threonine (T)/cysteine (C), 12) leucine (L)/isoleucine (I)/valine (V)/methionine (M), 13) alanine (A)/serine (S)/threonine (T)/methionine (M)/glycine (G), and 14) methionine (M)/lysine (K) (under hydrophobic conditions). Conservative substitutions also include "analog substitutions" where a standard amino acid is replaced by a non-standard (e.g., rare, synthetic, etc.) amino acid differing minimally from the standard amino acid. Such analog substitutions can be derived synthetically from the standard amino acids, are isomers, or are metabolite precursors. Examples of such "analog substitutions" include, but are not limited to, 1) Lys→ornithine (Orn), 2) Leu→Norleucine, 3) Lys→Lys[TFA], 4) Phe→phenylglycine, and 5) δ-amino butylglycine→δ-amino hexylglycine, where [TFA] refers to trifluoroacetyl. Conservative substitutions also include a replacement of an amino acid with another amino acid having shared properties as shown in FIG. 1. Such substitutions include substitutions of one amino acid in one of the following groups with another amino acid in the same group: 1) aromatic amino acids: phenylalanine (F)/tyrosine (Y)/histidine (H)/tryptophan (W); 2) aliphatic amino acids: isoleucine (I)/valine (V)/leucine(L)/alanine (A)/glycine (G); 3) positively charged amino acids: histidine (H)/lysine (K)/ arginine (R); 4) negatively charged amino acids: aspartate (D)/glutamate (E); and 5) tiny amino acids: cysteine (C)/ alanine (A)/glycine (G)/serine (S). Conservative substitutions also include substitutions of amino acids having uncharged polar side chains, i.e., serine (S)/threonine (T)/ asparagine (N)/glutamine (Q)/tyrosine (Y)/cysteine(S). Where amino acid sequences are disclosed herein, amino acid sequences comprising one or more of the above-identified conservative substitutions are also contemplated.

The term percent "identity" refers to two or more sequences that have a specified percentage of amino acid residues that are the same, when compared and aligned for maximum correspondence, as measured using standard sequence comparison algorithms or by visual inspection. For sequence comparison, typically one sequence acts as a reference sequence, to which test sequences are compared. By a peptide having an amino acid sequence with at least, for example, 50% identity to a reference amino acid sequence, it is intended that up to 50% of the amino acid residues in the test sequence may be inserted, deleted, or substituted with another amino acid. These alterations of the test sequence may occur at the amino or carboxy terminal positions of the reference amino acid sequence or anywhere between those terminal positions, interspersed either individually among residues in the reference sequence or in one or more contiguous groups within the reference sequence. Sequence identity of a test sequence is determined over the full length of the reference peptide or over a specified portion of the reference peptide. For example, in considering the amino acid sequence TMMS (SEQ ID NO: 67) as the reference sequence of the full sequence STMMSR (SEQ ID NO: 51), some test sequences with amino acid substitutions (e.g., TMAQ (SEQ ID NO: 68), TRMW (SEQ ID NO: 69), TVLS (SEQ ID NO: 70), IGMS (SEQ ID NO: 71), and KMTS (SEQ ID NO: 72)) have 50% sequence identity with the reference sequence, as do some test sequences with amino acid deletions (e.g., MM, MS, TM, TS), and some test sequences with amino acid insertions (e.g., TMMAAAAS (SEQ ID NO: 73), TAAMMSAA(SEQ ID NO: 74), TMAAAMAS (SEQ ID NO: 75)). Some test sequences with insertions, deletions, and/or substitutions will also have 50% sequence identity with the reference sequence. For example, again considering the amino acid sequence TMMS (SEQ ID NO: 67) as the reference sequence, sequences such as TCS or AMS (having one deletion and one substitution as compared to the reference sequence), or TLLMMT (SEQ ID NO: 76) or AMLIMS (SEQ ID NO: 77) (having two insertions and one substitution as compared to the reference sequence), have 50% identity with the reference sequence, as can be seen from the following sequence alignments:

```
TMMS

T-CS

TMMS

-AMS

T--MMS

TLLMMT

TM--MS

AMLIMS
```

By contrast, sequences such as TAAM (SEQ ID NO: 78) or FTMA (SEQ ID NO: 79) (having one substitution, one insertion, and one deletion as compared to the reference sequence), TCCRS (SEQ ID NO: 80) (having one insertion and two substitutions as compared to the reference sequence), or TLALM (SEQ ID NO: 81) (having two insertions, one substitution, and one deletion as compared to the reference sequence) have less than 50% sequence identity with the reference sequence TMMS (SEQ ID NO: 67), as can be seen in the following sequence alignments:

```
TM-MS

TAAM-
(40% sequence identity)

-TMMS
```

```
FTMA-
(40% sequence identity)

TMM-S

TCCRS
(40% sequence identity)

T-M-MS

TLALM-
(33% sequence identity)
```

When using a sequence comparison algorithm, test and reference sequences are entered into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, for example, by the local homology algorithm of Smith & Waterman (1981) *Adv. Appl. Math.* 2: 482, by the homology alignment algorithm of Needleman & Wunsch (1970) *J. Mol. Biol.* 48: 443, by the search for similarity method of Pearson & Lipman (1988) *Proc. Natl. Acad. Sci.*, USA, 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One illustrative but non-limiting method for determining a global sequence alignment is through use of the FASTDB computer program based on the algorithm of Brutlag et al. (1990) *Comp. App. Biosci.* 6: 237-245. Use of such alignment algorithms is known to one of ordinary skill in the art. If the test sequence is shorter than the reference sequence due to N- or C-terminal deletions, not because of internal deletions, a manual correction is typically made to the results. This is because the FASTDB program does not account for N- and C-terminal truncations of the test sequence when calculating global percent identity. For test sequences truncated at the N- and C-termini, relative to the reference sequence, the percent identity is corrected by calculating the number of residues of the reference sequence that are N- and C-terminal of the test sequence, which are not matched/aligned with a corresponding test residue, as a percent of the total bases of the reference sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the test sequence, that are not matched/aligned with the reference sequence, are typically considered for the purposes of manually adjusting the percent identity score. That is, only reference residue positions outside the farthest N- and C-terminal residues of the test sequence. For example, a 3-amino acid residue test sequence is aligned with a 4-residue reference sequence to determine percent identity. The deletion occurs at the N-terminus of the test sequence and therefore, the FASTDB alignment does not show a matching/alignment of the first residue at the N-terminus. The unpaired residue represents 25% of the sequence (number of residues at the N and C-termini not matched/total number of residues in the reference sequence) so 25% is subtracted from the percent identity score calculated by the FASTDB program. If the remaining 3 residues were perfectly matched the final percent identity would be 75%. In another example, a 3 residue test sequence is compared with a 4 residue reference sequence. This time the deletions are internal deletions so there are no residues at the N- or C-termini of the test sequence which are not matched/aligned with the reference. In this case the percent identity calculated by FASTDB is not manually corrected. Once again, only residue positions outside the N- and C-terminal ends of the test sequence, as displayed in the FASTDB alignment, which are not matched/aligned with the reference sequence, are manually corrected for. No other manual corrections are typically made or necessary.

The term "variant" refers to a peptide differing from a peptide of the invention, but retaining essential properties thereof (e.g., the ability to inhibit RHAMM activity). Generally, variants are overall closely similar, and may be identical, in many regions, to a peptide sequence of the invention. Besides conservative amino acid substitution, a variant peptide can include (i) substitutions with one or more of non-conserved amino acid residues, where the substituted amino acid residues may or may not be a standard amino acid and may or may not be a naturally occurring amino acid, or (ii) conservative substitutions with one or more non-standard or non-naturally occurring amino acid residues, or (iii) fusion of the peptide with another compound, such as a compound to increase the stability and/or solubility of the peptide (for example, polyethylene glycol), or (iv) fusion of the peptide with additional amino acids, such as, for example, an IgG Fc fusion region peptide, or leader or secretory sequence, or a sequence facilitating purification. Methods of making such variant peptides are within the skill of one of ordinary skill in the art. For example, peptide variants containing amino acid substitutions of charged amino acids with other charged or neutral amino acids may produce peptides with improved characteristics, such as less aggregation. Aggregation of pharmaceutical formulations both reduces activity and increases clearance due to the aggregate's immunogenic activity (see, e.g., Pinckard et al. (1967) *Clin. Exp. Immunol.* 2: 331340; Robbins et al. (1987) *Diabetes* 36: 838-845; Cleland et al. (1993) *Crit. Rev. Therapeutic Drug Carrier Systems,* 10: 307-377).

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). The subject can be a human (e.g., adult male, adult female, adolescent male, adolescent female, male child, female child) under the care of a physician or other health worker in a hospital, as an outpatient, or other clinical context. Alternatively, the subject may not be under the care or prescription of a physician or other health worker.

DETAILED DESCRIPTION

Figure 1:
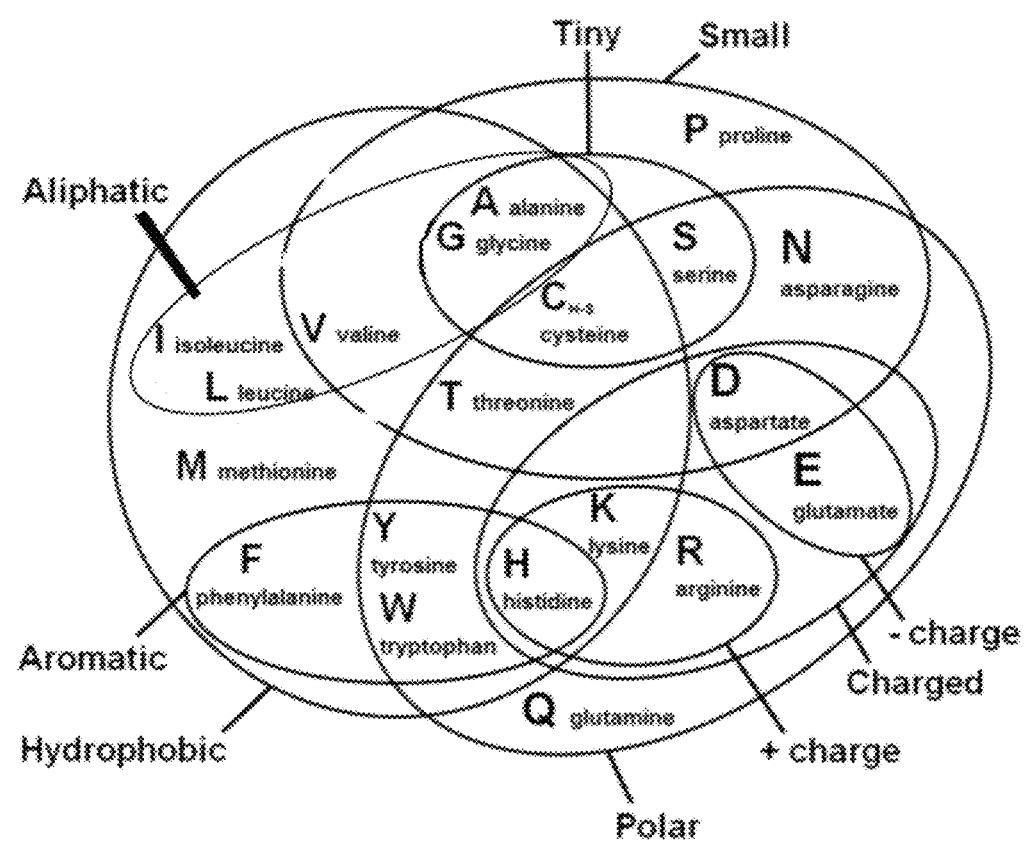
FIG. 1 illustrates the classification used herein for various naturally-occurring standard amino acids. It will be recognized that non-standard and/or non-naturally occurring amino acids can also fall into this classification.

Peptides and mimetics are identified that promote subcutaneous adipogenesis without inducing undesired visceral adipogenesis. These peptides are useful in a variety of cosmetic and therapeutic applications. Without being bound to a particular theory, it is believed that the peptides described herein achieve the adipogenic activity by inhibiting (fully or partially) RHAMM binding to hyaluronan and/or RHAMM biological activity (e.g., binding to CD44). The peptides of the invention are short in length having only about 5 to 14 amino acids as compared to other peptides known in the art to have adipogenic activity, such as the P-1 Peptide (peptide P15-1; SEQ ID NO: 1). The "short" peptides offer certain advantages such as reduced cost of production, reduced immunogenicity, increased activity, and increased penetration into skin when applied topically.

Peptide P15-1 (SEQ ID NO: 1) was isolated by screening a random phage library for peptides having the ability to bind to hyaluronan (HA). Alignments were performed to assess the similarity of the P15-1 (SEQ ID NO: 1) peptide to peptide B (SEQ ID NO: 2), a peptide derived from the HA-binding region of RHAMM. Since these peptides bind to hyaluronan and resemble a RHAMM sequence and have been shown to be adipogenic, it was possible to identify conserved motifs that are believed to be responsible for the adipogenic properties of the peptides.

It is also believed that the use of RHAMM-inhibiting peptides described herein provides signals that force differentiation into adipocytes. In addition, RHAMM −/− dermal fibroblasts express very low levels of smooth muscle actin indicating that RHAMM also regulates development of this mesenchymal stem cell lineage.

With respect to mesenchymal and other skin stem cells, a unique advantage of using the RHAMM-inhibiting peptides described herein for increasing subcutaneous fat is that its effects are selective. Thus, visceral fat, whose increased accumulation on body organs is associated with disease is decreased while subcutaneous fat is increased. This is an unusual effect and differentiates RHAMM's effects from other adipocyte promoting factors such as leptin that affect accumulation of both types of adipocytes. Accordingly, it is believed the peptides described herein will not increase visceral fat.

Another property of RHAMM is related to its very restricted expression in the adult human tissues. RHAMM is poorly expressed or not expressed physiologically but is increased following tissue injury or transformation to the neoplastic state. Therefore, the RHAMM-inhibitory peptides described herein should have low toxicity. In fact, it is believed that blocking RHAMM function can be beneficial to those with a tumor load or with inflammation-based diseases such as arthritis since RHAMM has pro-oncogenic, pro-inflammatory functions.

RHAMM Inhibiting Peptides.

Peptides are provided that inhibit RHAMM biological activity and thereby induce or stimulate subcutaneous adipogenesis. In one aspect of the invention, the peptide that stimulates subcutaneous adipogenesis has a length of 6 to 14 amino acids and comprises a motif having the sequence:

$X^1$-$X^2$-$X^3$-$X^4$-$X^5$-$X^6$ wherein at least one of $X^1$ and $X^6$ is a positively charged amino acid and the other of $X^1$ and $X^6$ is a positively charged amino acid, leucine (L), or alanine (A). $X^2$ is serine (S), glutamine (Q), alanine (A), glutamate (E), asparagine (N), proline (P), cysteine (C), lysine (K), aspartate (D), tryptophan (W), methionine (M), or threonine (T). $X^3$ is a negatively charged amino acid, alanine (A), glutamine (Q), serine (S), lysine (K), asparagine (N), or threonine (T). $X^4$ is isoleucine (I), valine (V), leucine (L), asparagine (N), alanine (A), serine (S), proline (P), threonine (T), or glutamine (Q); and $X^5$ is serine (S), aspartate (D), threonine (T), leucine (L), alanine (A), phenylalanine (F), glutamate (E), asparagine (N), glycine (G), arginine (R), glutamine (Q), histidine (H), or isoleucine (I); provided that $X^2$ and $X^5$ are not both glutamine (Q) and provided that when $X^1$ is arginine (R), $X^3$ is not lysine (K).

The length of the peptide can be, for example, 13 amino acids, 12 amino acids, 11 amino acids, 10 amino acids, 9 amino acids, 8 amino acids, 7 amino acids, or 6 amino acids.

In certain aspects of the invention, both $X^1$ and $X^6$ are positively charged amino acids.

$X^1$ is preferably lysine (K).

$X^6$ is preferably lysine (K) or arginine (R), and is more preferably lysine (K).

In some aspects of the invention, $X^2$ is serine (S), glutamine (Q), alanine (A), glutamate (E), asparagine (N), proline (P), cysteine (C), lysine (K), aspartate (D), tryptophan (W), or methionine (M). $X^2$ is preferably serine (S) or glutamine (Q). More preferably, $X^2$ is serine (S).

$X^3$ can be a negatively charged amino acid, alanine (A), glutamine (Q), serine (S), lysine (K), or asparagine (N). For example, $X^3$ can be a negatively charged amino acid (e.g., glutamate (E), aspartate (D)). $X^3$ is preferably glutamate (E).

$X^4$ can be isoleucine (I), valine (V), leucine (L), asparagine (N), alanine (A), serine (S), proline (P), or threonine (T). For example, $X^4$ can be isoleucine (I), valine (V), or leucine (L). $X^4$ is preferably valine.

$X^5$ can be serine (S), aspartate (D), threonine (T), leucine (L), alanine (A), phenylalanine (F), glutamate (E), asparagine (N), glycine (G), arginine (R), glutamine (Q), or histidine (H). For example, $X^5$ can be serine (S), aspartate (D), threonine (T), or glutamate (E). $X^5$ is preferably serine (S).

For example, in certain peptides of the present invention, $X^1$ is lysine (K), $X^2$ is serine (S), $X^3$ is glutamate (E), $X^4$ is valine (V), $X^5$ is serine (S), and $X^6$ is lysine (K).

In certain peptides of the invention, the motif is KSEVSK (SEQ ID NO: 3), KQEVSK (SEQ ID NO: 4), KQEVDK (SEQ ID NO: 5), KQENTK (SEQ ID NO: 6), KSEVLK (SEQ ID NO: 7), KQDVSK (SEQ ID NO: 8), KQELDR (SEQ ID NO: 9), LEEIFK (SEQ ID NO: 10), LSELEK (SEQ ID NO: 11), KSEISK (SEQ ID NO: 12), KNEVSK (SEQ ID NO: 13), KSEVTK (SEQ ID NO: 14), KSEVNK (SEQ ID NO: 15), KSDVSK (SEQ ID NO: 16), KSQVSK (SEQ ID NO: 17), KPEVSK (SEQ ID NO: 18), KSEVGK (SEQ ID NO: 19), KSDSSK (SEQ ID NO: 20), KSSPSK (SEQ ID NO: 21), KSEASK (SEQ ID NO: 22), KSELRK (SEQ ID NO:23), KCEVSK (SEQ ID NO: 24), KSKPSK (SEQ ID NO: 25), KKEVSK (SEQ ID NO: 26), KEEVSK (SEQ ID NO: 27), KSETSK (SEQ ID NO: 28), KSNVSK (SEQ ID NO: 29), KDEVSK (SEQ ID NO: 30), KSEVEK (SEQ ID NO: 31), KSAVSK (SEQ ID NO: 32), KWEVSK (SEQ ID NO: 33), KMEVSK (SEQ ID NO: 34), KSEVQK (SEQ ID NO: 35), KSEVHK (SEQ ID NO: 36), KSSVSK (SEQ ID NO: 37), ASEVSK (SEQ ID NO: 38), KAEVSK (SEQ ID NO: 39), KSEVAK (SEQ ID NO: 40), or KSEVSA (SEQ ID NO: 41). For example, the motif can be KSEVSK (SEQ ID NO: 3).

In some aspects of the invention, the peptide for stimulating subcutaneous adipogenesis is KSEVSK (SEQ ID NO: 3), KQEVSK (SEQ ID NO: 4), KQEVDK (SEQ ID NO: 5), KQENTK (SEQ ID NO: 6), KSEVLK (SEQ ID NO: 7), KQDVSK (SEQ ID NO: 8), KQELDR (SEQ ID NO: 9), LEEIFK (SEQ ID NO: 10), LSELEK (SEQ ID NO: 11), KSEISK (SEQ ID NO: 12), KNEVSK (SEQ ID NO: 13), KSEVTK (SEQ ID NO: 14), KSEVNK (SEQ ID NO: 15), KSDVSK (SEQ ID NO: 16), KSQVSK (SEQ ID NO: 17), KPEVSK (SEQ ID NO: 18), KSEVGK (SEQ ID NO: 19), KSDSSK (SEQ ID NO: 20), KSSPSK (SEQ ID NO: 21), KSEASK (SEQ ID NO: 22), KSELRK (SEQ ID NO:23), KCEVSK (SEQ ID NO: 24), KSKPSK (SEQ ID NO: 25), KKEVSK (SEQ ID NO: 26), KEEVSK (SEQ ID NO: 27), KSETSK (SEQ ID NO: 28), KSNVSK (SEQ ID NO: 29), KDEVSK (SEQ ID NO: 30), KSEVEK (SEQ ID NO: 31), KSAVSK (SEQ ID NO: 32), KWEVSK (SEQ ID NO: 33), KMEVSK (SEQ ID NO: 34), KSEVQK (SEQ ID NO: 35), KSEVHK (SEQ ID NO: 36), KSSVSK (SEQ ID NO: 37), ASEVSK (SEQ ID NO: 38), KAEVSK (SEQ ID NO: 39), KSEVAK (SEQ ID NO: 40), KSEVSA (SEQ ID NO: 41), LKSEVSK (SEQ ID NO: 42), QLKSEVSK (SEQ ID NO: 43), SQLKSEVSK (SEQ ID NO: 44), NSQLKSEVSK (SEQ ID NO: 45), ENSQLKSEVSK (SEQ ID NO: 46), DENSQLKSEVSK (SEQ ID NO: 47), KDENSQLKSEVSK (SEQ ID NO: 48), or LKDENSQLKSEVSK (SEQ ID NO: 49). For example, the peptide can be KSEVSK (SEQ ID NO: 3), LKSEVSK (SEQ ID NO: 42), QLKSEVSK (SEQ ID NO: 43), or SQLKSEVSK (SEQ ID NO: 44). Preferred peptides include KSEVSK (SEQ ID NO: 3), LKSEVSK (SEQ ID NO: 42), or SQLKSEVSK (SEQ ID NO: 44). KSEVSK (SEQ ID NO: 3) is a more preferred peptide.

In certain aspects of the invention, the motif is not RQKVLK (SEQ ID NO: 84) or LQATQK (SEQ ID NO: 85).

Another aspect of the present invention relates to peptides for stimulating subcutaneous adipogenesis. The peptide has a length of 5 to 14 amino acids and comprises a motif having the sequence $X^1$-$X^2$-$X^3$-$X^4$-$X^5$-$X^6$ wherein at least one of $X^1$ and $X^6$ is a positively charged amino acid, and the other of $X^1$ and $X^6$ is a positively charged amino acid, leucine (L) or a conservative substitution therefor, alanine (A) or a conservative substitution therefor, or absent. In such peptides, $X^2$—$X^3$-$X^4$-$X^5$ is an amino acid sequence having at least 50% sequence identity with the amino acid sequence SEVS (SEQ ID NO: 50) and having a length of 4 to 8 amino acids.

The length of the peptide can be 6 to 14 amino acids. For example, the length of the peptide can be 13 amino acids, 12 amino acids, 11 amino acids, 10 amino acids, 9 amino acids, 8 amino acids, 7 amino acids, or 6 amino acids.

In some aspects of the invention, the length of $X^2$-$X^3$-$X^4$-$X^5$ is 4 to 6 amino acids, or 4 amino acids.

$X^2$-$X^3$-$X^4$-$X^5$ can have at least about 75% sequence identity with the amino acid sequence SEVS (SEQ ID NO: 50).

In certain aspects, both $X^1$ and $X^6$ are positively charged amino acids.

$X^1$ is preferably lysine (K).

$X^6$ is preferably lysine (K) or arginine (R), and is more preferably lysine (K).

Yet another aspect of the present invention relates to peptides for stimulating subcutaneous adipogenesis, wherein the peptide has a length of 6 to 13 amino acids and comprises a motif having the sequence:

$X^1$-$X^2$-$X^3$-$X^4$-$X^5$-$X^6$ wherein $X^1$ is serine (S) or a conservative substitution therefor; $X^2$ is a hydrophobic amino acid; $X^3$ is any amino acid; $X^4$ is a hydrophobic amino acid; $X^5$ is serine (S), arginine (R), or a conservative substitution therefor; and $X^6$ is a charged amino acid; provided that $X^1$, $X^2$ and $X^4$ are not all glycine (G) and provided that $X^1$ is not glutamine (Q).

The length of the peptide can be, for example, 13 amino acids, 12 amino acids, 11 amino acids, 10 amino acids, 9 amino acids, 8 amino acids, 7 amino acids, or 6 amino acids.

In certain aspects of the invention, $X^1$ is serine (S), cysteine (C), alanine (A), glycine (G), threonine (T), tyrosine (Y), or methionine (M). $X^1$ is preferably serine (S).

$X^2$ can be a hydrophobic nonaromatic amino acid. For example, $X^2$ can be threonine (T), isoleucine (I), valine (V), leucine (L), alanine (A), glycine (G), cysteine (C), or methionine (M). $X^2$ is preferably threonine (T) or isoleucine (I), and is more preferably threonine (T).

$X^3$ can be a hydrophobic nonaromatic amino acid, a hydrophobic polar amino acid, a positively charged amino acid, or proline (P). For example, $X^3$ can be methionine (M), valine (V), glycine (G), threonine (T), arginine (R), leucine (L), proline (P), or a conservative substitution therefor. $X^3$ is preferably methionine (M), valine (V), glycine (G), threonine (T), arginine (R), leucine (L), or proline (P). $X^3$ is more preferably methionine (M), leucine (L), or a conservative substitution therefor, and is even more preferably methionine (M).

$X^4$ can be a hydrophobic nonaromatic amino acid or a hydrophobic nonpolar amino acid. In some aspects of the invention, $X^4$ is methionine (M), leucine (L), valine (V), or a conservative substitution therefor. $X^4$ is preferably methionine (M), leucine (L), or valine (V), and is more preferably methionine (M).

$X^5$ can be arginine (R) or a conservative substitution therefor. Alternatively, $X^5$ can be serine (S) or a conservative substitution therefor. $X^5$ is preferably serine (S).

$X^6$ can be arginine (R) or a conservative substitution therefor. $X^6$ is preferably arginine (R).

In certain of the peptides for stimulating subcutaneous adipogenesis, the motif is STMMSR (SEQ ID NO: 51), SIMMSR (SEQ ID NO: 52), STLMSR (SEQ ID NO: 53), STVMSR (SEQ ID NO: 54), STGLSR (SEQ ID NO: 55), STTMSR (SEQ ID NO: 56), STRMSR (SEQ ID NO: 57), STLMRR (SEQ ID NO: 58), or STPVSR (SEQ ID NO: 59). For example, the motif can be STMMSR (SEQ ID NO: 51).

For example, the peptide is STMMSR (SEQ ID NO: 51), SIMMSR (SEQ ID NO: 52), STLMSR (SEQ ID NO: 53), STVMSR (SEQ ID NO: 54), STGLSR (SEQ ID NO: 55), STTMSR (SEQ ID NO: 56), STRMSR (SEQ ID NO: 57), STLMRR (SEQ ID NO: 58), STPVSR (SEQ ID NO: 59), STMMSRS (SEQ ID NO: 60), STMMSRSH (SEQ ID NO: 61), STMMSRSHK (SEQ ID NO: 62), STMMSRSHKT (SEQ ID NO: 63), STMMSRSHKTR (SEQ ID NO: 64), STMMSRSHKTRS (SEQ ID NO: 65), or STMMSRSHK-TRSH (SEQ ID NO: 66). For example, the peptide can be STMMSR (SEQ ID NO: 51) or STMMSRSHK (SEQ ID NO: 62).

In certain aspects of the invention, the motif is not QLVKRK (SEQ ID NO: 86), QKVLKR (SEQ ID NO: 87), GGRGRR (SEQ ID NO: 88), GGRGGR (SEQ ID NO: 89), or GGGGGR (SEQ ID NO: 90).

Still another aspect of the present invention relates to peptides for stimulating subcutaneous adipogenesis, wherein the peptide has a length of 6 to 13 amino acids and comprises a motif having the sequence $X^1$-$X^2$-$X^3$-$X^4$-$X^5$-$X^6$ wherein $X^1$ is serine (S) or a conservative substitution therefor and $X^6$ is a charged amino acid. $X^2$-$X^3$-$X^4$-$X^5$ is an amino acid sequence having at least 50% sequence identity with the amino acid sequence TMMS (SEQ ID NO: 67) and having a length of 2 to 8 amino acids.

The length of the peptide can be, for example, 12 amino acids, 11 amino acids, 10 amino acids, 9 amino acids, 8 amino acids, 7 amino acids, or 6 amino acids.

In some aspects, the length of $X^2$-$X^3$-$X^4$-$X^5$ is 3 to 7 amino acids, 3 to 6 amino acids, or 4 amino acids.

$X^1$ is preferably serine (S).

$X^6$ is preferably a positively charged amino acid, for example arginine (R), lysine (K), histidine (H), or a conservative substitution therefor. $X^6$ is more preferably arginine (R) or a conservative substitution therefor, and is even more preferably arginine (R).

$X^2$-$X^3$-$X^4$-$X^5$ can have at least about 75% sequence identity with the amino acid sequence SEVS (SEQ ID NO: 50).

In any of the above-described peptides, the peptide can have a substantially alpha-helical conformation.

Any of the above-described peptides can be a beta-peptide.

Any of the above-described peptides can be in the retro form, the inverso form, or the retro-inverso form.

In any of the above-described peptides, all of the amino acids in the peptide can be L amino acids. Alternatively, the peptide can comprise one or more D amino acids, or all of the amino acids in the peptide can be D amino acids. Thus, the peptide can comprise a mixture of L amino acids and D amino acids.

Peptide Variants

The peptides described herein can be composed of amino acids joined to each other by peptide bonds or modified peptide bonds, i.e., peptide isosteres, and may contain amino acids other than the 20 gene-encoded standard amino acids. The peptides may be modified by either natural processes, such as posttranslational processing, or by chemical modification techniques that are well known in the art. Modifications can occur anywhere in a peptide, including the peptide backbone, the amino acid side-chains and the amino or carboxyl termini. The same type of modification may be present in the same or varying degrees at several sites in a peptide. Also, a peptide may contain many types of modifications.

In certain aspects of the invention, peptides may be branched, for example, as a result of ubiquitination, and they may be cyclic, with or without branching. Cyclic, branched, and branched cyclic peptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine-cysteine disulfide bonds, formation of pyroglutamate, formylation, gamma-carboxylation, glycosylation, GPI anchor formation, hydroxylation, iodination, methylation, myristoylation, oxidation, PEGylation, proteolytic processing, phosphorylation, prenylation, palmitoylation, racemization, selenoylation, sulfation, transfer-RNA mediated addition of amino acids to proteins such as arginylation, and ubiquitination. (see, e.g., Creighton et al. (1993) *Proteins—Structure and Molecular Properties,* 2nd Ed., T. E. Creighton, W. H. Freeman and Company, New York; Johnson, ed. (1983) *Posttranslational Covalent Modification Of Proteins,* Academic Press, New York; Seifter et al. (1990) Meth. Enzymol., 182: 626-646; Rattan et al. (1992) Ann. N.Y. Acad. Sci., 663: 48-62; and the like).

Using known methods of protein engineering and recombinant DNA technology, variants may be generated to improve or alter the characteristics of the peptides described herein. Such variants include deletions, insertions, inversions, repeats, and substitutions (e.g., conservative substitutions) selected according to general rules well known in the art so as have little effect on activity.

Peptoids are also contemplated wherein the peptoid has an essentially corresponding monomer sequence, where a natural amino acid is replaced by an N-substituted glycine derivative, if the N-substituted glycine derivative resembles the original amino acid in hydrophilicity, hydrophobicity, polarity, etc. The following are illustrative, but non-limiting N-substituted glycine replacements: N-(1-methylprop-1-yl) glycine→isoleucine (I), N-(prop-2-yl)glycine→valine (V), N-benzylglycine→phenylalanine (F), N-(2-hydroxyethyl) glycine→serine (S), and the like. In certain aspects of the invention, substitutions need not be "exact". Thus for example, in certain aspects of the invention, N-(2-hydroxyethyl)glycine may substitute for S, T, C, and/or M; N-(2-methylprop-1-yl)glycine may substitute for V, L, and/or I; N-(2-hydroxyethyl)glycine can be used to substitute for T or S. In general, one may use an N-hydroxyalkyl-substituted glycine to substitute for any polar amino acid, an N-benzyl- or N-aralkyl-substituted glycine to replace any aromatic amino acid, an N-alkyl-substituted glycine such as N-butyl-glycine to replace any nonpolar amino acid (e.g., L, V, I, etc.), and an N-(aminoalkyl)glycine to replace any basic polar amino acid (e.g., L and R).

Functionalization and Protecting Groups.

While the various peptides described herein are shown without protecting groups, they can bear one or more protecting groups. The protecting groups can be coupled to the C- and/or N-terminus of the peptide and/or to one or more internal residues of the peptide. Thus, for example, any of the peptides described herein can bear, e.g., an acyl group protecting the amino terminus and/or an amide group protecting the carboxyl terminus. These blocking groups enhance the helix-forming tendencies of the peptides.

Without being bound by a particular theory, it is believed that blockage, particularly of the amino and/or carboxyl termini of the peptide can improve stability and/or skin penetration when administered topically.

Suitable protecting groups include, but are not limited to, acetyl, amide, and alkyl groups with acetyl and alkyl groups being particularly preferred for N-terminal protection and amide groups being preferred for carboxyl terminal protection. Alkyl protecting groups include, but are not limited to, alkyl chains as in fatty acids such as propionyl, formyl, and others. For example, the alkyl can be 3- to 20-carbon alkyl. Carboxyl protecting groups include amides, esters, and ether-forming protecting groups. Such blocking groups include alkyl groups of various lengths, e.g., groups having the formula: $CH_3—(CH_2)_n—CO—$ where n ranges from about 1 to about 20, preferably from about 1 to about 16 or 18, more preferably from about 3 to about 13, and most preferably from about 3 to about 10.

Other suitable protecting groups include, but are not limited to, fluorenylmethyloxycarbonyl (FMOC), t-butoxycarbonyl (t-BOC), 9-fluoreneacetyl, 1-fluorenecarboxylic, 9-florenecarboxylic, 9-fluorenone-1-carboxylic, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), cyclohexyloxy (cHxO), t-butoxymethyl (Bum), t-butoxy (tBuO), t-Butyl (tBu), acetyl (Ac), and trifluoroacetyl (TFA).

Protecting/blocking groups are well known to those of skill as are methods of coupling such groups to the appropriate residue of the peptide (see, e.g., Greene et al., (1991) *Protective Groups in Organic Synthesis, 2nd ed.,* John Wiley & Sons, Inc. Somerset, N.J.). For example, acetylation can be accomplished during synthesis when the peptide is on the resin using acetic anhydride. Amide protection can be achieved by the selection of a proper resin for the synthesis. During the synthesis of the peptide, rink amide resin can used. After the completion of the synthesis, the semipermanent protecting groups on acidic bifunctional amino acids such as Asp and Glu, the basic amino acid Lys, and the hydroxyl of Tyr are all simultaneously removed. The peptides released from such a resin using acidic treatment have the N-terminus protected with acetyl and the carboxy-terminus protected with $NH_2$ with the simultaneous removal of all of the other protecting groups.

The peptides may comprise one or more D-amino acids (dextro rather than levo). Every other, or even every amino acid (e.g., every enantiomeric amino acid) of the peptide can be a D-amino acid. For example, at least 50%, at least 80%, at least 90% or even all of the enantiomeric amino acids can be D-amino acids.

The peptides can also be functionalized with a polymer (e.g., polyethylene glycol and/or a cellulose or modified cellulose) to increase bioavailability.

Peptide Mimetics.

Peptide analogs are commonly used in the pharmaceutical industry as non-peptide drugs with properties analogous to those of the template peptide. These types of non-peptide compounds are termed "peptide mimetics" or "peptidomimetics" (Fauchere (1986) *Adv. Drug Res.* 15: 29; Veber and Freidinger (1985) TINS p.392; and Evans et al. (1987) *J. Med. Chem.* 30: 1229) and are usually developed with the aid of computerized molecular modeling. Peptide mimetics that are structurally similar to peptides of the invention may be used to produce an equivalent therapeutic or prophylactic effect.

Peptidomimetics are structurally similar to a peptide (e.g., KSEVSK (SEQ ID NO: 3)), but have one or more peptide linkages optionally replaced by a linkage such as $-CH_2NH-$, $-CH_2S-$, $-CH_2-CH_2-$, $-CH=CH-$ (cis and trans), $-COCH_2-$, $-CH(OH)CH_2-$, or $-CH_2SO-$ by methods known in the art and further described in the following references: Spatola (1983) p. 267 in *Chemistry and Biochemistry of Amino Acids, Peptides, and Proteins*, B. Weinstein, eds., Marcel Dekker, New York; Spatola (1983) *Vega Data* 1(3) *Peptide Backbone Modifications*. (general review); Morley (1980) *Trends Pharm Sci* pp. 463-468 (general review); Hudson et al. (1979) *Int J Pept Prot Res* 14:177-185 ($-CH_2NH-$, $-CH_2-CH_2-$); Spatola et al. (1986) *Life Sci* 38:1243-1249 ($-CH_2-S-$); Hann, (1982) *J Chem Soc Perkin Trans I* 307-314 ($-CH=CH-$, cis and trans); Almquist et al. (1980) *J Med Chem.* 23: 1392-1398 ($-COCH_2-$); Jennings-White et al. (1982) *Tetrahedron Lett.* 23: 2533 ($-COCH_2-$); Szelke et al. (1982) European Appln. EP 45665 ($-CH(OH)CH_2-$); Holladay et al. (1983) *Tetrahedron Lett* 24:4401-4404 ($-C(OH)CH_2-$); and Hruby (1982) *Life Sci.*, 31:189-199 ($-CH_2-S-$)).

A particularly useful non-peptide linkage is $-CH_2NH-$. Such peptide mimetics may have significant advantages over peptides, such as more economical production, greater chemical stability, enhanced pharmacological properties (half-life, absorption, potency, efficacy, etc.), and/or reduced antigenicity.

Circular permutations of the peptides described herein or constrained peptides (including cyclized peptides) comprising the motifs described herein or a substantially identical motif can be generated by methods known in the art (Rizo and Gierasch (1992) *Ann. Rev. Biochem.* 61: 387), for example, by adding internal cysteine residues capable of forming intramolecular disulfide bridges which cyclize the peptide.

Peptide Preparation.

In various aspects of the invention, the peptides described herein can be chemically synthesized using standard chemical peptide synthesis techniques or, particularly where the peptide does not comprise D-amino acid residues, the peptide can be recombinantly expressed. Where polypeptides containing one or more D-amino acids are to be recombinantly expressed, a host organism (e.g. bacteria, plant, fungal cells, etc.) can be cultured in an environment where one or more of the amino acids is provided to the organism exclusively in a D-form. Recombinantly expressed peptides in such a system then incorporate those D-amino acids. Also, D-amino acids can be incorporated in recombinantly expressed peptides using modified amino acyl-tRNA synthetases that recognize D-amino acids.

The peptides (containing D- and/or L-amino acids) can be chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of the invention. Techniques for solid phase synthesis are well known to those of skill in the art and are described, for example, by Barany and Merrifield (1963) *Solid-Phase Peptide Synthesis*; pp. 3-284 in *The Peptides: Analysis, Synthesis, Biology. Vol.* 2*: Special Methods in Peptide Synthesis, Part A*.; Merrifield et al. (1963) *J. Am. Chem. Soc.*, 85: 2149-2156, and Stewart et al. (1984) *Solid Phase Peptide Synthesis*, 2nd ed. Pierce Chem. Co., Rockford, Ill.

The peptides can be synthesized by the solid phase peptide synthesis procedure using a benzhydrylamine resin (Beckman Bioproducts, 0.59 mmol of $NH_2$/g of resin) as the solid support. The carboxy terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor can be used for this purpose.

It is noted that in the chemical synthesis of peptides, particularly peptides comprising D-amino acids, the synthesis usually produces a number of truncated peptides in addition to the desired full-length product. Thus, the peptides are typically purified using, e.g., HPLC.

D-amino acids, beta amino acids, non-natural amino acids, non-standard amino acids, and the like can be incorporated at one or more positions in the peptide simply by using the appropriately derivatized amino acid residue in the chemical synthesis. Modified residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form and/or otherwise modified amino acids can be completely omitted or incorporated at any position in the peptide as desired.

When the peptides are synthesized using recombinant expression systems, a DNA sequence that encodes the desired peptide is typically created, and placed in an expression cassette under the control of a promoter to express the peptide in a host cell. The expressed peptide is isolated and, if required, renatured. DNA encoding a peptide of the invention can be prepared by any suitable method, including, for example, cloning and restriction of appropriate sequences or direct chemical synthesis. This nucleic acid can be easily ligated into an appropriate vector containing appropriate expression control sequences (e.g. promoter, enhancer, etc.), and, optionally, containing one or more selectable markers (e.g. antibiotic resistance genes).

A nucleic acid sequence encoding a peptide described herein can be expressed in a variety of host cells, including, but not limited to, *E. coli*, other bacterial hosts, yeast, fungus, and various higher eukaryotic cells such as insect cells (e.g. SF3), the COS, CHO and HeLa cells lines and myeloma cell lines. The recombinant protein gene will typically be operably linked to appropriate expression control sequences for each host. For *E. coli* this can include a promoter such as the T7, trp, or lambda promoters, a ribosome binding site and preferably a transcription termination signal. For eukaryotic cells, illustrative control sequences can include a promoter and often an enhancer (e.g., an enhancer derived from immunoglobulin genes, SV40, cytomegalovirus, etc.), and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant peptide(s) can be purified according to standard procedures of the art, including, but not limited to, ammonium sulfate precipitation, affinity columns, column chromatography, and gel electrophoresis (see, generally, R. Scopes, (1982) *Protein Purification*, Springer-Verlag, N.Y.; Deutscher (1990) *Methods in Enzymology Vol.* 182: *Guide to Protein Purification*., Academic Press, Inc. N.Y.). Substantially pure compositions of at least about 90 to 95% homogeneity are preferred, and 98 to 99% or more homogeneity are most preferred.

One of skill in the art would recognize that after chemical synthesis, biological expression, or purification, the peptide may possess a conformation substantially different than desired native conformation. In this case, it may be necessary to denature and reduce the peptide and then to cause the molecule to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski et al., for example, describes the denaturation and reduction of inclusion body proteins in guanidine-DTE. The protein is then refolded in a redox buffer containing oxidized glutathione and L-arginine.

One of skill would recognize that modifications can be made to the peptides of the invention without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Pharmaceutical and Cosmetic Formulations

The peptide(s) described herein are administered to a subject (e.g., a mammal) in need thereof, e.g., to induce or potentiate subcutaneous adipocyte recruitment or formation (e.g., to induce subcutaneous adipogenesis).

These peptide(s) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the peptide(s) can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, the disulfide salts of a number of delivery agents are described in PCT Publication WO 2000/059863. Similarly, acid salts of therapeutic peptides, peptoids, or other mimetics, and can be prepared from the free base using conventional methodology that typically involves reaction with a suitable acid. Generally, the base form of the peptide is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to, both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, or salicylic acid, as well as inorganic acids, e.g., hydrochloric acid, hydrobromic acid, sulfuric acid, nitric acid, or phosphoric acid. An acid addition salt can be reconverted to the free base by treatment with a suitable base. Certain particularly preferred acid addition salts of the peptides described herein include halide salts, such as may be prepared using hydrochloric or hydrobromic acids. Conversely, preparation of basic salts of the peptides s described herein are prepared in a similar manner using a pharmaceutically acceptable base such as sodium hydroxide, potassium hydroxide, ammonium hydroxide, calcium hydroxide, or trimethylamine. Basic salts include alkali metal salts, e.g., the sodium salt, and copper salts.

For the preparation of salt forms of a peptide, the pKa of the counterion is preferably at least about 2 pH lower than the pKa of the agent. Similarly, for the preparation of salt forms of acidic agent, the pKa of the counterion is preferably at least about 2 pH greater than the pKa of the agent. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of peptide and counterion) in an aqueous environment.

Typically, the counterion is a pharmaceutically acceptable counterion. Suitable anionic salt forms include, but are not limited to, acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of peptide esters typically involves functionalization of hydroxyl and/or carboxyl groups that are present within the molecular structure of the peptide. For example, the esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides of the peptides can also be prepared using techniques known to those skilled in the art. For example, amides can be prepared from esters, using suitable amine reactants, or they can be prepared from an anhydride or an acid chloride by reaction with ammonia or a lower alkyl amine.

The peptides can be formulated for subcutaneous, parenteral, topical, oral, nasal (or otherwise inhaled), rectal, or local administration, such as by aerosol or transdermally. The compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

The peptides described herein can also be combined with a pharmaceutically or cosmetically acceptable carrier (excipient) to form a pharmacological or cosmetic composition. Pharmaceutically acceptable carriers include those approved by a regulatory agency of the Federal or a state government or listed in the U.S. Pharmacopeia or other generally recognized pharmacopeia for use in or on animals, and more particularly humans. A "carrier" refers to, for example, a diluent, adjuvant, excipient, auxiliary agent or vehicle with which one or more of the peptides described herein is administered.

Pharmaceutically acceptable carriers can contain one or more physiologically acceptable compounds that act, for example, to stabilize the composition or to increase or decrease the absorption of the peptide. Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compounds that reduce the clearance or hydrolysis of the peptides, or other excipients, stabilizers and/or buffers.

Other physiologically acceptable compounds, particularly of use in the preparation of tablets, capsules, gel caps, and the like include, but are not limited to binders, diluent/fillers, disentegrants, lubricants, and suspending agents.

To manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the peptide and the resulting composition is compressed. Where necessary, the compressed product is coated using known methods for masking taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and EUDRAGIT (Rohm & Haas, Germany; methacrylic-acrylic copolymer).

Other physiologically acceptable compounds that can be formulated with the peptides include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier depends, for example, on the route of administration of the peptide and on the particular physiochemical characteristics of the peptide.

Preferably, the excipients are sterile and generally free of contaminants. These compositions can be sterilized by conventional, well-known sterilization techniques. For various oral dosage form excipients, such as tablets and capsules, sterility is not required; the USP/NF standard is usually sufficient.

Nanoemulsion Formulations.

The peptides described herein can be formulated in a nanoemulsion. Nanoemulsions include, but are not limited to, oil-in-water (O/W) nanoemulsions, and water-in-oil (W/O) nanoemulsions. Nanoemulsions can be defined as emulsions with mean droplet diameters ranging from about 20 to about 1000 nm. Usually, the average droplet size is between about 20 nm or 50 nm and about 500 nm. The terms sub-micron emulsion (SME) and mini-emulsion are used as synonyms.

Illustrative oil-in-water (O/W) nanoemulsions include, but are not limited to: (1) surfactant micelles, which are micelles composed of small molecules, surfactants or detergents (e.g., SDS/PBS/2-propanol) which are suitable for predominantly hydrophobic peptides; (2) polymer micelles, which are micelles composed of polymer, copolymer, or block copolymer surfactants (e.g., Pluronic L64/PBS/2-propanol) which are suitable for predominantly hydrophobic peptides; (3) blended micelles, which are micelles in which there is more than one surfactant component or in which one of the liquid phases (generally an alcohol (e.g., ethanol) or fatty acid compound) participates in the formation of the micelle (e.g., octanoic acid/PBS/EtOH) which are suitable for predominantly hydrophobic peptides; (4) integral peptide micelles, which are blended micelles in which the peptide serves as an auxiliary surfactant, forming an integral part of the micelle (e.g., amphipathic peptide/PBS/mineral oil) which are suitable for amphipathic peptides; and (5) pickering (solid phase) emulsions, which are emulsions in which the peptides are associated with the exterior of a solid nanoparticle (e.g., polystyrene nanoparticles/PBS/no oil phase) which are suitable for amphipathic peptides.

Illustrative water-in-oil (W/O) nanoemulsions include, but are not limited to: (1) surfactant micelles, which are micelles composed of small molecules surfactants or detergents (e.g., dioctyl sulfosuccinate/PBS/2-propanol, isopropylmyristate/PBS/2-propanol, etc.) which are suitable for predominantly hydrophilic peptides; (2) polymer micelles, which are micelles composed of polymer, copolymer, or block copolymer surfactants (e.g., PLURONIC® L121/PBS/2-propanol), which are suitable for predominantly hydrophilic peptides; (3) blended micelles, which are micelles in which there is more than one surfactant component or in which one of the liquid phases (generally an alcohol (e.g., ethanol) or fatty acid compound) participates in the formation of the micelle (e.g., capric/caprylic diglyceride/PBS/EtOH) which are suitable for predominantly hydrophilic peptides; (4) integral peptide micelles, which are blended micelles in which the peptide serves as an auxiliary surfactant, forming an integral part of the micelle (e.g., amphipathic peptide/PBS/polypropylene glycol) which are suitable for amphipathic peptides; and (5) pickering (solid phase) emulsions, which are emulsions in which the peptides are associated with the exterior of a solid nanoparticle (e.g., chitosan nanoparticles/no aqueous phase/mineral oil) which are suitable for amphipathic peptides.

As indicated above, the nanoemulsions can comprise one or more surfactants or detergents. For example, the surfactant can be a non-anionic detergent (e.g., a polysorbate surfactant or a polyoxyethylene ether). Surfactants that find use in the present invention include, but are not limited to, surfactants such as the TWEEN®, TRITON®, and TYLOXAPOL® families of compounds. Preferably, the surfactant is a polysorbate surfactant (e.g., TWEEN 20®, TWEEN 40®, TWEEN 60®, and TWEEN 80®, a phenoxypolyethoxyethanol (e.g., TRITON® X-100, X-301, X-165, X-102, and X-200, and TYLOXAPOL®), or sodium dodecyl sulfate.

The nanoemulsion can further comprise an emulsifying agent to aid in the formation of the emulsion. Emulsifying agents include compounds that aggregate at the oil/water interface to form a kind of continuous membrane that prevents direct contact between two adjacent droplets. Some oil-in-water emulsion compositions can readily be diluted with water to a desired concentration without impairing their anti-pathogenic properties.

In addition to discrete oil droplets dispersed in an aqueous phase, oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water). These lipid structures are formed as a result of hydrophobic forces that drive apolar residues (e.g., long hydrocarbon chains) away from water. The lipid preparations can generally be described as surfactant lipid preparations (SLPs). SLPs are minimally toxic to mucous membranes and are believed to be metabolized within the small intestine (see e.g., Hamouda et al., (1998) *J. Infect. Disease* 180: 1939).

The emulsion can comprise a discontinuous oil phase distributed in an aqueous phase, a first component comprising an alcohol (e.g., ethanol) and/or glycerol, and a second component comprising a surfactant or a halogen-containing compound. The aqueous phase can comprise any type of aqueous phase including, but not limited to, water (e.g., deionized water, distilled water, water-for-injection, tap water) and solutions (e.g., phosphate buffered saline solution, or other buffer systems). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, or mineral oil. Generally, the oil phase comprises about 30 to about 90 volume % of the oil-in-water emulsion (i.e., constitutes 30-90% of the total volume of the final emulsion), more preferably from about 50 to about 80 volume % of the emulsion.

The emulsion can also include a halogen-containing compound such as a chloride salt (e.g., NaCl, KCl, etc.), a cetylpyridinium halide, a cetyltrimethylammonium halide, a cetyldimethylethylammonium halide, a cetyldimethylbenzylammonium halide, a cetyltributylphosphonium halide, a dodecyltrimethylammonium halide, a tetradecyltrimethylammonium halide, cetylpyridinium chloride, cetyltrimethylammonium chloride, cetylbenzyldimethylammonium chloride, cetylpyridinium bromide, cetyltrimethylammonium bromide, cetyldimethylethylammonium bromide, cetyltributylphosphonium bromide, dodecyltrimethylammonium bromide, or tetradecyltrimethylammonium bromide.

The emulsion can also include a quaternary ammonium compound such as N-alkyldimethyl benzyl ammonium saccharinate; 1,3,5-Triazine-1,3,5(2H,4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy)ethyl dimethyl benzyl ammonium chloride; alkyl-1- or 3-benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-tris(2-hydroxyethyl)-s-triazine; myristalkonium chloride and/or quaternium-14; N,N-dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; or n-octadecyl dimethyl benzyl ammonium chloride.

Nanoemulsion formulations and methods of making such are well known to those of skill in the art and described for example in U.S. Pat. Nos. 7,476,393, 7,468,402, 7,314,624, 6,998,426, 6,902,737, 6,689,371, 6,541,018, 6,464,990, 6,461,625, 6,419,946, 6,413,527, 6,375,960, 6,335,022, 6,274,150, 6,120,778, 6,039,936, 5,925,341, 5,753,241, 5,698,219, an d5,152,923 and in Fanun et al. (2009) *Microemulsions: Properties and Applications (Surfactant Science)*, CRC Press, Boca Raton Fl.

Cosmetic Formulations.

One or more of the peptides described herein can be incorporated into formulations for cosmetic use. Such cosmetic formulations can be for topical application and can be formulated as skin creams (e.g., face creams) or body lotions, wrinkle-removing creams, or incorporated into cosmetics, sunscreens, or moisturizers.

The peptides can be incorporated into formulations that optionally further include fillers, moisturizers, vitamins (e.g., vitamin E), and/or colorants/tints.

Suitable injectable cosmetic formulations include, but are not limited to, formulations incorporating one or more of the peptides in combination with one or more filler materials. Illustrative materials usable as injectable cosmetic wrinkle fillers include, but are not limited to, temporary (absorbable) fillers such as collagen (e.g., synthetic collagen, bovine collagen, porcine collagen, human collagen, etc.), hyaluronic acid gel, calcium hydroxylapatite (typically implanted in the form of a gel), or poly-L-lactic acid (PLLA). The peptides can also be incorporated into injectable cosmetic formulations containing permanent (non-absorbable) fillers. Illustrative "permanent" fillers include, but are not limited to, polymethylmethacrylate beads (PMMA microspheres).

The peptides described herein can be incorporated into or administered in conjunction with commercial dermal fillers (e.g., RADIESSE® volumizing filler (about 30% by volume calcium hydroxylapatite (CaHA) microspheres (diameter of 25 μm to 45 μm) suspended in a sodium carboxymethylcellulose gel carrier)), JUVEDERM® injectable gel (a cross-linked hyaluronic acid produced by *Streptococcus equi* bacteria, formulated to a concentration of 24 mg/mL, optionally with 0.3% w/w lidocaine, in a physiologic buffer), RESTYLANE® dermal filler (a gel of 20 mg/mL hyaluronic acid generated by *Streptococcus* species of bacteria, chemically crosslinked with BDDE, and suspended in phosphate buffered saline), SCULPTRA® Aesthetic injectable implant (suspension containing microparticles of poly-L-lactic acid (PLLA), carboxymethylcellulose, non-pyrogenic mannitol and sterile water for injection).

Such injectable formulations can additionally include an anesthetic (e.g., lidocaine or an analog thereof).

The injectable formulations are substantially sterile or sterile and/or meet regulatory agency guidelines for subcutaneous injectable fillers Dose/Administration The peptides described herein can be administered to a subject using any route known in the art, including e.g., by injection (e.g., intravenous, intraperitoneal, subcutaneous, intramuscular, or intradermal), inhalation, transdermal application, rectal administration, vaginal administration, or oral administration. Preferred routes of administration include subcutaneous, transdermal, or topical application.

An effective amount of the peptides can be administered via local (i.e., non-systemic) administration, such as by peripheral administration which includes, but is not limited to, peripheral intramuscular, intraglandular, and subcutaneous administration.

Administration of the peptide(s) can be in any convenient manner, e.g., by injection, intravenous and arterial stents (including eluting stents), catheter, oral administration, inhalation, transdermal application, rectal administration, and the like.

The peptides can be formulated with a pharmaceutically acceptable carrier, e.g., as described above, prior to administration. Pharmaceutically acceptable carriers are determined in part by the particular composition being administered, as well as by the particular method used to administer the composition. Accordingly, there are a wide variety of suitable formulations for the peptides described herein (see, e.g., *Remington's Pharmaceutical Sciences,* 17th ed., 1989).

The dose administered to a subject, in the context of the methods described herein should be sufficient to effect a beneficial therapeutic response (e.g., increased subcutaneous adipogenesis) in the subject over time. The dose will be determined by the efficacy of the particular vehicle/delivery method employed, the site of administration, the route of administration, and the condition of the subject, as well as the body weight or surface area of the subject to be treated. The size of the dose also will be determined by the existence, nature, and extent of any adverse side-effects that accompany the administration of a particular peptide in a particular subject.

The terms "effective amount" or "amount effective to" or "therapeutically effective amount" refers to an amount sufficient to induce a detectable therapeutic (or cosmetic) response in the subject (e.g. an amount sufficient to induce or to potentiate adipogenesis). In determining the effective amount of peptide to be administered, the attending physician will decide the dosage with which to treat each individual patient, taking into consideration a variety of factors, such as age, body weight, general health, diet, sex, peptide and formulation to be administered, route of administration, the severity of the condition being treated and the response of the subject and any adverse effects (e.g., irritation or allergies). The peptides described herein can also be administered at a rate determined by the $LD_{50}$ of the peptide and/or the therapeutic efficacy/activity of the peptide, and the side-effects of the peptide at various concentrations, as applied to the mass and overall health of the subject.

The dose of peptide can vary widely, and will be selected primarily based on activity of the active ingredient, and body weight in accordance with the particular mode of administration selected and the subject's needs. Concentrations, however, will typically be selected to provide dosages ranging from about 0.1 to about 50 mg/kg/day or more. Typical dosages range from about 1 mg/kg/day to about 50 mg/kg/day, about 2 mg/kg/day to about 30 mg/kg/day, or about 3 mg/kg/day to about 20 mg/kg/day, such as about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, or most preferably from about 11.0 mg/kg/day to about 15.0 mg/kg/day. Dosages of peptides can range from about 10 mg/kg/day to about 50 mg/kg/day. Alternatively, the dosages can range from about 20 mg to about 50 mg given twice daily. It will be appreciated that such dosages may be varied to optimize a therapeutic and/or cosmetic regimen in a particular subject or group of subjects.

Administration can be accomplished via single or divided doses, e.g., doses administered on a regular basis (e.g., once daily or twice daily) for a period of time (e.g., 2, 3, 4, 5, or 6 days or 1-3 weeks or more).

The peptides described herein can be administered systemically (e.g., orally, or as an injectable) in accordance with standard methods well known to those of skill in the art. Peptides can be administered to the oral cavity in various forms such as lozenges, aerosol sprays, mouthwash, coated swabs, and the like. Various buccal, and sublingual formulations are also contemplated. The peptides can be administered in a depot formulation when formulated as an injectable to provide treatment over a period of time.

The peptides can be administered topically, e.g., to the skin surface, to a topical lesion or wound, to a surgical site, and the like.

The peptides can also be delivered through the skin using conventional transdermal drug delivery systems, i.e., transdermal "patches" wherein the peptides are typically contained within a laminated structure that serves as a drug delivery device to be affixed to the skin. In such a structure, the drug composition is typically contained in a layer, or "reservoir," underlying an upper backing layer. The term "reservoir" in this context refers to a quantity of active ingredient that is ultimately available for delivery to the surface of the skin. Thus, for example, the "reservoir" may include the active ingredient peptide in an adhesive on a backing layer of the patch, or in any of a variety of different matrix formulations known to those of skill in the art. The patch may contain a single reservoir, or it may contain multiple reservoirs. For example, the reservoir can comprise a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, for example, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the peptides and any other materials that are present.

Other formulations for topical delivery include, but are not limited to, ointments, gels, sprays, fluids, and creams. Ointments are semisolid preparations that are typically based on petrolatum or other petroleum derivatives. As with other carriers or vehicles, an ointment base should be inert, stable, nonirritating and nonsensitizing. Creams containing the selected peptide are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery.

One or more peptides described herein can be provided as a "concentrate", e.g., in a storage container (e.g., in a premeasured volume) ready for dilution, or in a soluble capsule ready for addition to a volume of water, alcohol, hydrogen peroxide, or other diluent. For example, the peptides can be lyophilized for later reconstitution.

Illustrative Uses

The adipogenic peptides (or mimetics thereof) described herein find use in a number of applications. For example, enhancing the formation of subcutaneous fat has use in plastic surgery procedures since subcutaneous fat provides plumpness and firmness to skin. Aging skin contains less subcutaneous fat. Therefore administering one or more peptides described herein to the desired area to promote subcutaneous fat formation results in plumper and more youthful appearing skin. This approach can replace current methods for transplanting adipocytes from other areas of the body (e.g., the thigh or buttocks), a procedure that often exhibits a low success rate.

The peptides described herein can be administered to selectively enhance subcutaneous adipose tissue (e.g., to enhance subcutaneous adipose tissue without substantially increasing visceral adipose and/or other adipose tissue). In response to administration of the peptides, adipocyte formation occurs in dermal fibroblasts and volume is added in a selected subcutaneous area in the subject.

The peptides described herein can be used to reducing scarring. This can be accomplished by administering one or more of the peptides in an amount sufficient to reduce the area of scarring, and/or to improve the appearance of a scarred area. The scarring, for example, can be scarring produced by a burn, scarring produced by surgery, scarring produced by acne, scarring produced by a biopsy, or scarring produced by an injury.

The peptides described herein can be used, e.g., in various cosmetic procedures, to improve the appearance of skin. This can be accomplished by administering one or more of the peptides in an amount sufficient to improve the appearance of skin in an area of a subject. Such administering can include subcutaneously administration to a region such as lips, eye lids, cheeks, forehead, chin, neck, and the like. The peptides can be used in these methods, or others to reduce wrinkles, reduce sagging skin, improve the surface texture of skin, diminish, remove or fill-in wrinkles, remove or diminish age spots, and/or remove dark circles under the eyes. These cosmetic applications are illustrative and not intended to be limiting. In view of the teachings provided herein, other cosmetic applications will be recognized by and available to one of skill in the art.

The peptides described herein can be used to improve tissue volume in an area of a subject. This can be accomplished by administering one or more of the peptides described herein in an amount sufficient to increase tissue volume in an area of a subject. For example, the increase of tissue volume can involve firming or augmenting breast tissue and/or firming or augmenting tissue in the buttocks or other regions of the body or face.

The peptides can also be used to smooth skin in an area of a subject. This can be accomplished by administering one or more of the peptides described herein in an amount sufficient to smooth skin in the desired area. The smoothing can include smoothing skin scarred by acne, smoothing areas of cellulite, smoothing or reducing stretch marks, and/or smoothing out wrinkles.

The peptides described herein can be used to recruit stem cells to the formation of subcutaneous fat in a subject. This can be accomplished by administering one or more of the peptides described herein in an amount sufficient to recruit stem cells to the formation of subcutaneous fat. This has utility, for example, in various reconstructive surgical procedures and the like.

The peptides described herein can be used to reconstructing tissue in a subject. Such reconstruction can include, for example, breast reconstruction (e.g. after surgery to remove tumors), or face or limb reconstruction (e.g. after car accident or burning). This can be accomplished by administering one or more of the peptides described herein in an amount to increase the volume of the tissue during or after a tissue reconstruction procedure. The peptides are optionally used in conjunction with tissue grafting material or other procedures that enhance youthful skin or repair of damaged tissues.

The peptides can also be used to reduce heel pain in a subject by administering one or more of the peptides described herein in an amount sufficient to reduce heel pain experienced by the subject when walking.

The peptides described herein can be administered for augmentation of subcutaneous fat to improve thermo regulation and/or improve immune function. The subject can be treated with the peptides to prevent disease or to treat ongoing disease associated with increased organ fat including but not limited to cardiovascular disease, and other obesity associated diseases.

The administration in any of these methods can be local or systemic, and can be by any route described herein, such as topical, subcutaneous, transdermal, oral, nasal, vaginal, and/or rectal administration. Preferably, the peptides are administered by subcutaneous injection. Alternatively, the peptides are preferably administered topically in the form of a skin cream such as a face cream, or transdermally via a transdermal patch.

While the uses and methods are described with respect to use in humans, they are also suitable for animal, e.g., veterinary use. Thus certain preferred organisms include, but are not limited to humans, non-human primates, canines, equines, felines, porcines, ungulates, largomorphs, and the like.

Having described the invention in detail, it will be apparent that modifications and variations are possible without departing from the scope of the invention defined in the appended claims.

EXAMPLES

The following examples are offered to illustrate, but not to limit the claimed invention.

Example 1: Assays to Measure Adipogenesis

The following assays were used to assess adipogenic activity of the peptides in the experiments described below in Example 2.

Assay 1

Reagents: (1) 3-isobutyl-1-methylxanthine (IBMX) solution: 0.5M in DMSO; (2) Insulin solution: 10 mg/mL recombinant human insulin; (3) Dexamethasone solution in 10 mM in ethanol; (4) Oil Red 0 (0.36% in 60% isopropanol) or BODIPY dye (BODIPY 493/503 (4,4-difluoro-1,3,5,7-tetramethyl-4-bora-3a,4a-diaza-s-indacene-8-propionic acid, succinimidyl ester) from Invitrogen at 4-10 µM).

Preparation of Media:

Adipogenesis Initiation Media: mesenchymal stem cell expansion media/0.5 mM IBMX/1 µM dexamethasone. Mesenchymal stem cell expansion media is commercially available from Millipore. The IBMX Solution was diluted 1:1000 and the Dexamethasone Solution was diluted 1:10,000 in expansion media containing antibiotics and antimycotics. The prepared media was stored at 4° C.

Adipogenesis Progression Media for positive control: mesenchymal stem cell expansion media/10 µg/mL insulin. The Insulin Solution was diluted 1:1000 in the expansion media and stored at 4° C.

Experimental Adipogenesis Progression Media: mesenchymal stem cell expansion media/1-100 µg/mL RHAMM antagonist peptides.

Adipogenesis Maintenance Media: mesenchymal stem cell expansion media containing antibiotics and antimycotics.

Negative Control Media: DMEM/10% normal calf serum.

Assay Method:

Pre-adipocyte stem cells including bone marrow mesenchymal stem cells and fibroblasts including reticular and papillary dermal fibroblasts were propagated using standard tissue culture methods. Cells were trypsinized to remove the cells from the substratum. The trypsin was neutralized and cells were counted using a hemocytometer. Cells were resuspended at 30,000 cells/mL in expansion media. 1 mL of cell suspension was plated per well of 24-well plate, with several wells left empty for blank well staining.

Cells were incubated for 1-2 days until they reached confluency. Approximately 1.8 mL of media was removed from each well and replaced with 2 mL Adipogenesis Initiation Media. For negative control wells, expansion media only was used at this step and for subsequent media changes. For all media changes, media was replaced as gently as possible to avoid disturbing the monolayer.

Cells were incubated for 48 hours at 37° C., 5% $CO_2$. 2 mL media was removed from each well, and replaced with 2 mL either positive control or experimental Adipogenesis Progression Media per well. Cells were again incubated for 48 hours at 37° C., 5% $CO_2$. 2 mL of media was removed from each well and replaced with 2 mL Adipogenesis Maintenance Media per well. In addition, media was added to the empty wells reserved for blank well staining Cells were incubated for at least 48 hours at 37° C., 5% $CO_2$. Media was replaced every 48-72 hours. Accumulation of intracellular lipid droplets continued for at least 5 days.

Quantification of Adipogenesis:

Oil Red O Staining

For quantification of Oil Red 0 staining, media was removed and cells were washed twice with PBS, using care to gently add the PBS. 0.5 mL Oil Red 0 solution was added per well of 24-well plate, including to the wells lacking cells, but containing media. Cells were incubated for 15 minutes at room temperature. The staining solution was then removed and wells were washed three times with 1 mL of phosphate buffered saline (PBS). In some experiments, following removal of the last wash, stained plates were scanned or photographed.

Adipogenesis was quantified using a spectrophotometer or fluorometer. 0.25 mL Dye Extraction Solution (isopropyl alcohol) was added per well, and the plate was set on an orbital shaker or platform rocker for 15-30 minutes. Extracted dye was transferred into a cuvette and absorbance was read in a spectrophotometer at visible range for oil red 0 or transferred to a 96-well plate and quantified in a plate reader.

BODIPY Staining

For quantification of BODIPY dye uptake, media was removed and cells were washed twice with PBS, using care to gently add the PBS. Cells were then fixed in 3% paraformaldehyde, washed in PBS then incubated for 1 hour in the dark with the BODIPY solution, prepared in PBS. Monolayers were washed and then extracted for measurement of dye in a fluorometer or mounted on slides and examined in a confocal fluorescent microscope.

Blank Well Staining

The stain extracted from wells lacking cells represents non-specific binding of the dye to the plate. This value was subtracted from the absorbances of experimental wells to obtain a more accurate assessment of specific staining Assay 2

Reagents:

The dexamethasone, insulin, and Oil Red 0 solutions were the same as described above for assay 1. Indomethacin Solution contained 10 mM indomethacin in methanol. The BODIPY 493/503 dye was used at a concentration of 4 µM.

Preparation of Media:

Adipogenesis Maintenance Media was prepared as described above.

Adipogenesis Induction Media: To prepare 501 mL of Adipogenesis Induction Media, 50 µL of the 10 mM stock solution of dexamethasone, 500 µL of the 10 mg/ml stock solution of insulin, 5 ml of a 10 mM stock solution of indomethacin, and 5 mL of a 100× stock solution of penicillin and streptomycin were added to 490 mL of mesenchymal stem cell expansion media.

Assay Method:

Pre-adipocyte stem cells, bone marrow mesenchymal stem cells and fibroblasts such as dermal reticular and papillary fibroblasts were propagated using standard tissue culture methods. Cells were trypsinized to remove cells from the substratum, the trypsin was neutralized, and cells were counted using a hemocytometer. Cells were resuspended at 60,000 cells/ml in low glucose DMEM containing 10% calf serum. 1 mL of cell suspension per well was plated in a 24-well plate, with several wells left empty for blank well staining.

Cells were incubated overnight and had reached confluency at this point. Approximately 1.8 ml of media was removed from each well and replaced with 2 ml Adipogenesis Induction Media. For negative control wells, expansion medium only was used at this step and for subsequent media changes. For all media changes, media was replaced as gently as possible to avoid disturbing the monolayer.

Cells were incubated for 3 days at 37° C., 5% $CO_2$, media was replaced with fresh Adipogenesis Induction Media, and cells were incubated for an additional three days, at which point adipogenesis could be observed in about 5-10% of cells. Media was removed and replaced with 2 ml of maintenance medium containing either RHAMM antagonist peptides (experimental group) or insulin (concentration as in the induction medium used as positive control). Cells were incubated for 3 days at 37° C., 5% $CO_2$.

Media was removed and BODIPY or Oil Red O staining was performed as described above for assay 1.

Example 2: Identification and Testing of Adipogenic Peptides

We previously showed that ablation of RHAMM expression promoted adipogenesis (Tolg et al., 2006, J Cell Biol). We produced a RHAMM carboxy-terminal sequence [$^{AA681}$LDAFEAEKQA LLNEHGATQE QLNKIRDSYA QLLGHQNLKQ KIKHVVKLKD ENSQLKSEVS KLRSQLVKRK QNELRLQGEL DKALGIRHFD PSKAFCHASK ENFTPLKEGN PNCC$^{aa794}$ (SEQ ID NO: 91)] as a recombinant protein, prepared antibodies to this protein fragment, and showed that both the protein fragment and the antibody promoted adipogenesis using a commercially available mesenchymal stem cell kit. The results indicated that this 114 amino acid protein fragment contains adipogenic activity.

Figure 2:
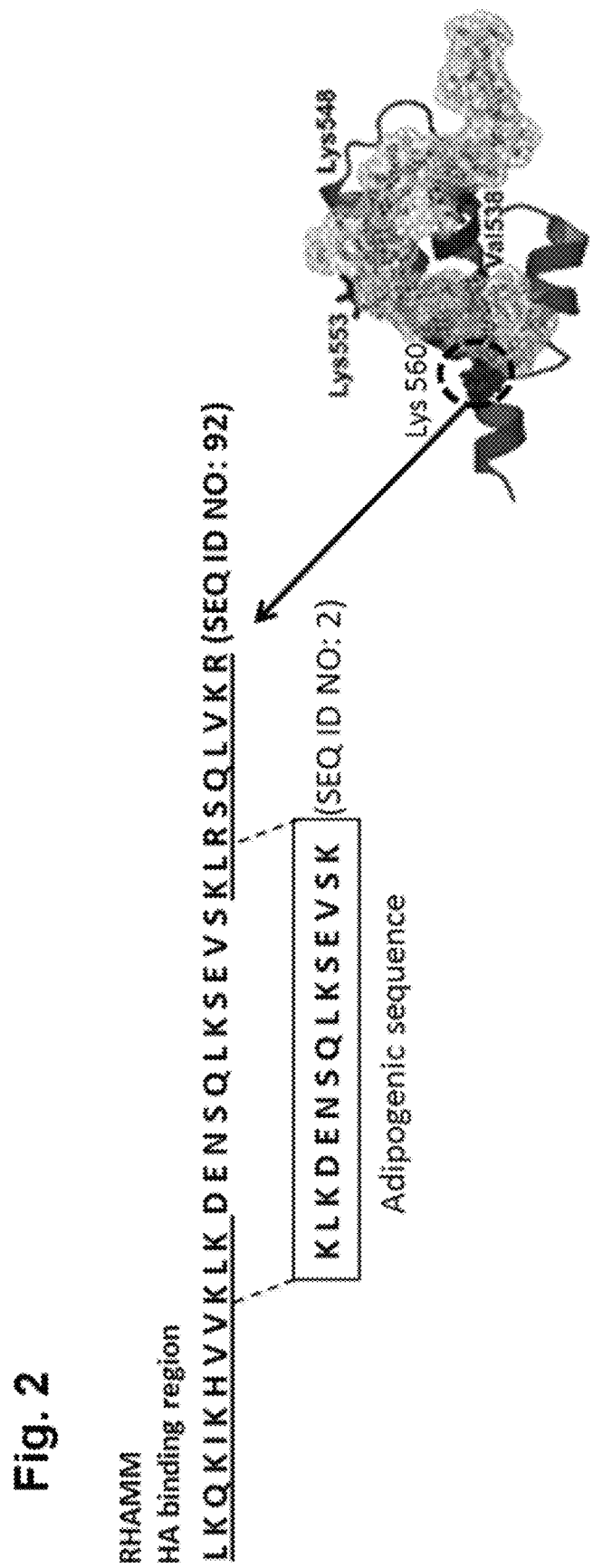
FIG. 2 illustrates the RHAMM HA binding region and the adipogenic subdomain.

We hypothesized that the fragment and the antibody were blocking RHAMM function by competitive inhibition and by direct binding/blocking of RHAMM, respectively. Using truncation analyses, we further reduced the size of the peptide to 32 amino acids (LKQKIKHVVKLKDENSQLK-SEVSKLRSQLVKR (SEQ ID NO: 92)) and showed that adipogenic activity is localized to a 15 amino acid peptide (KLKDENSQLKSEVSK (SEQ ID NO: 2); "peptide B" or "B-1" herein) shown in FIG. 2. We synthesized this peptide chemically to use as a competitive blocker and we prepared antibodies against this sequence tagged with keyhold lymphocyte hemacyanin (KLH) to directly bind/block RHAMM function. Both reagents effectively block RHAMM function and promote adipogenesis in tissue culture and in vivo.

Figure 7:
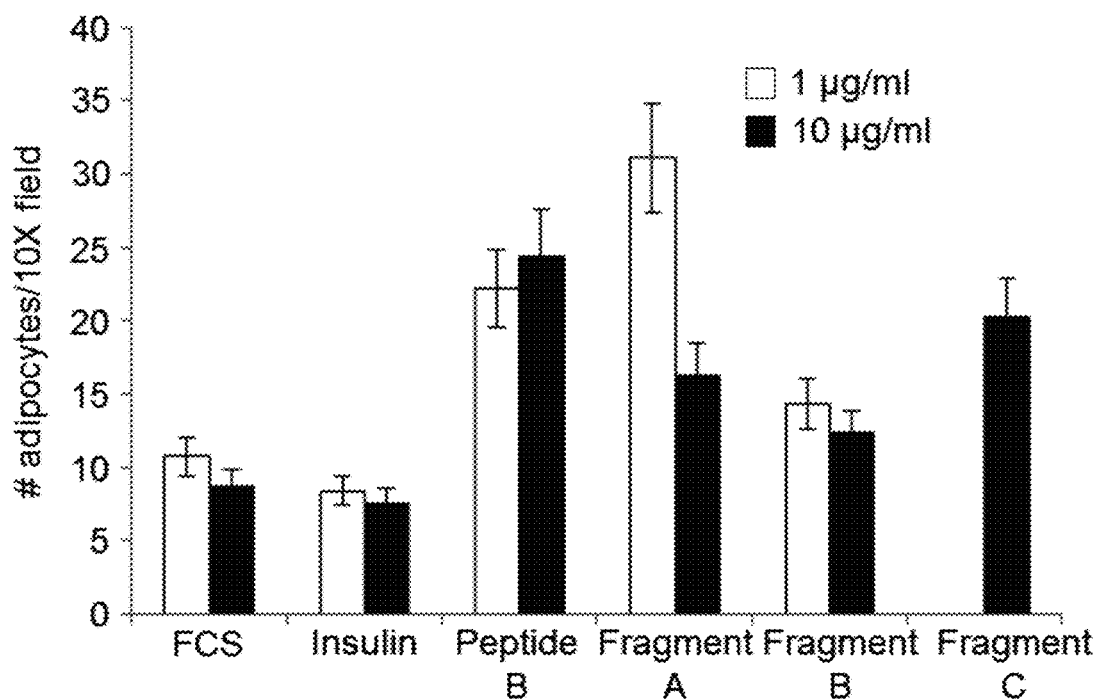
FIG. 7 provides illustrative data showing the adipogenic activity of various peptides.

We noted that the RHAMM sequence that contains adipogenic activity also contains the hyaluronan binding region of this protein. We therefore performed unbiased screening of a random phage library for peptides that bind to hyaluronan, and identified a hyaluronan binding peptide (SEQ ID NO: 1, peptide P15-1, also referred to as P-1) that similarly promotes adipogenesis in tissue culture and in vivo. The sequence of peptide P15-1 is shown in FIG. 7.

Examples of the adipogenic effects of RHAMM antagonists (peptide B (SEQ ID NO: 2), peptide P15-1 (SEQ ID NO: 1), and the antibody to peptide B) are summarized in Table 1. Peptide P15-1, peptide B, and a RHAMM antibody were assayed for their effects on pre-adipocyte stem cells in culture and when injected into the dermis of aged rats. Reagents were ranked on a scale of 0-5 with 5 representing the highest possible score and a completely filled in Harvey ball. "2D" refers to two-dimensional tissue culture.

TABLE 1

The adipogenic potential of peptide and antibody reagents.

| | 2D rat Pre-adipocytes (rat mesenchymal stem cells) | In vivo Rat skin | 2D human Pre-adipocytes |
|---|---|---|---|
| peptide P15-1 (SEQ ID NO: 1) | 2 | 2 | 2 |
| peptide B (SEQ ID NO: 2) | 5 | 5 | 5 |
| Antibody | 4 | 4 | 4 |

All of these reagents can replace insulin in their ability to promote adipogenesis in mesenchymal stem cells or papillary fibroblasts. However, peptide B (SEQ ID NO: 2) was the most adipogenic of these reagents (Table 1) and was therefore further characterized in culture for dose range activity and several animal models in vivo.

Figure 3A:
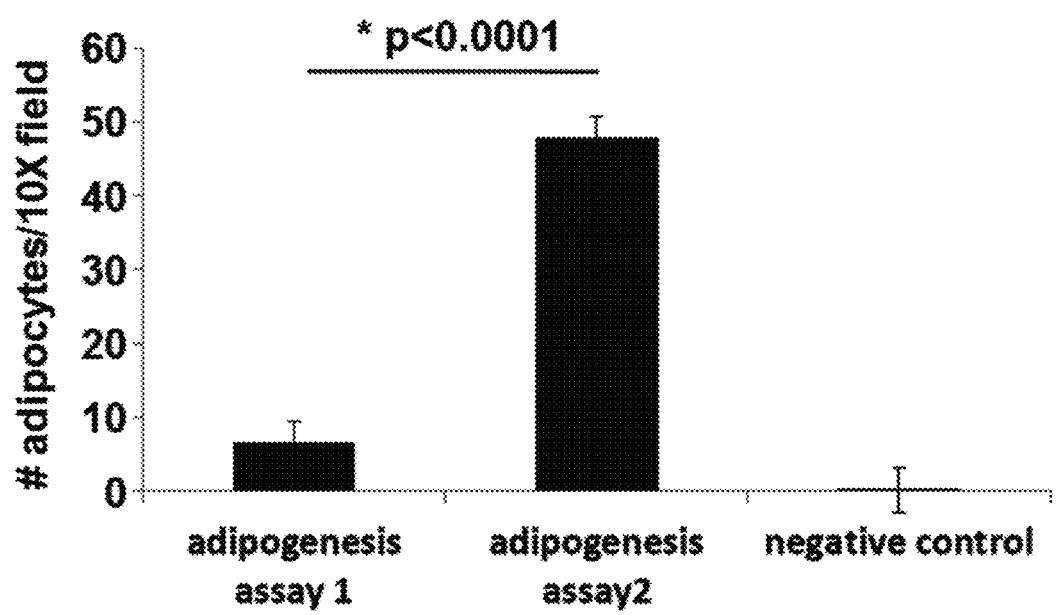
FIGS. 3A-3C provide illustrative adipogenesis dose-response data for peptide B (SEQ ID NO: 2).

FIG. 3A shows the adipogenic effect of insulin in assays 1 and 2 in bone marrow mesenchymal stem cells. The negative controls in this experiment were cells cultured in maintenance medium only.

Figure 3B:
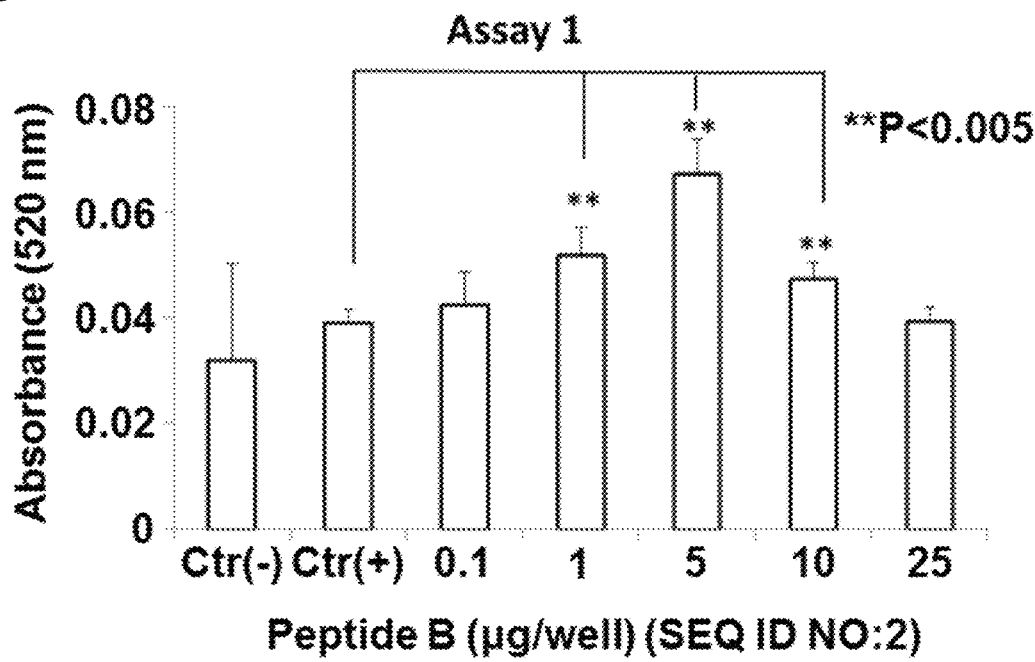
Figure 3C:
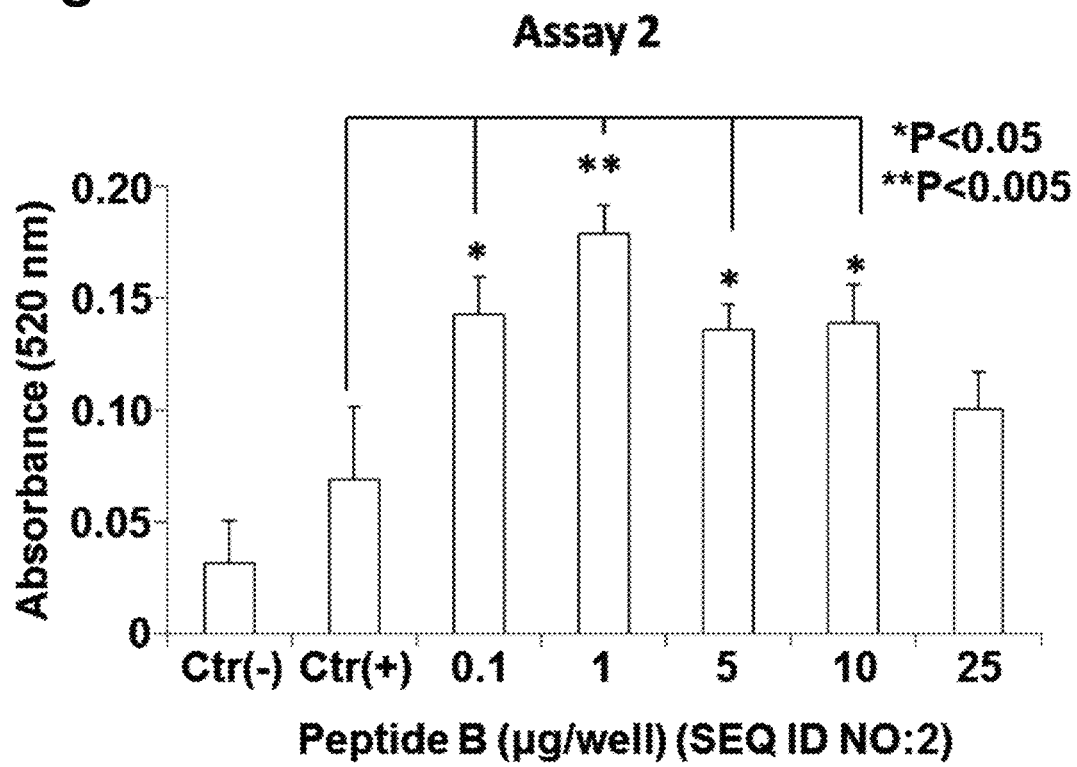
Figure 4:
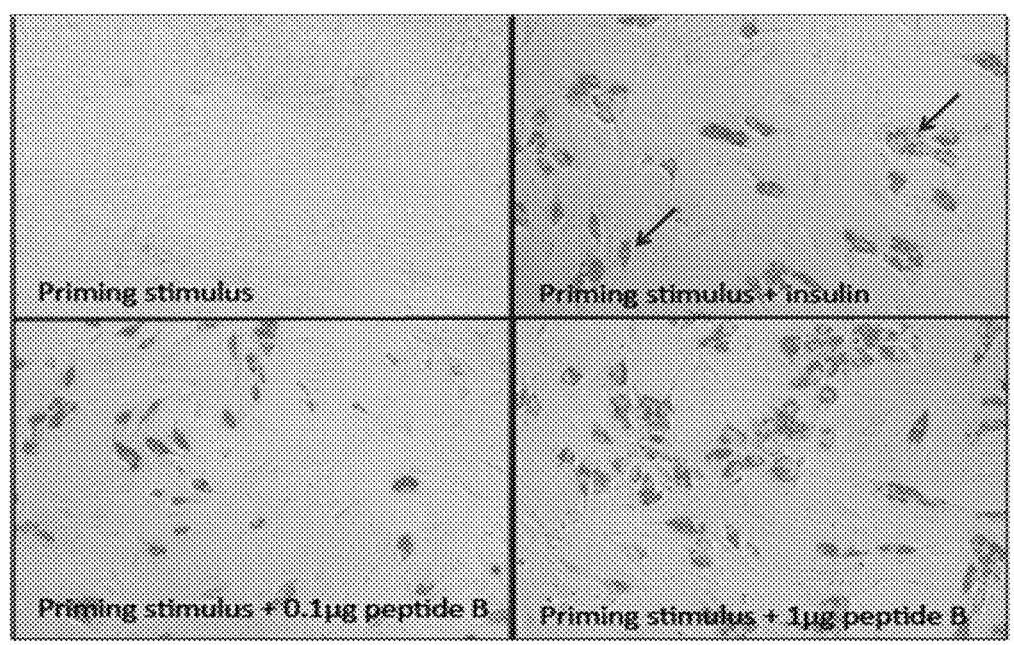
FIG. 4 shows illustrative micrographs showing lipid accumulation in cells in response to treatment with peptide B (SEQ ID NO: 2).

As shown in FIGS. 3B and 3C, and the micrographs in FIG. 4, in bone marrow mesenchymal stem cells, a maximum adipogenic effect was obtained at 1-5 µg of peptide B (SEQ ID NO: 2), depending upon the screening assay used. FIG. 4 shows the adipogenic effect of peptide B in rat bone marrow mesenchymal stem cells using assay 1. The arrows in FIG. 4 indicate lipid droplets, and "priming stimulus" refers to the treatment of the cells with dexamethasone and IBMX.

Figure 5A:
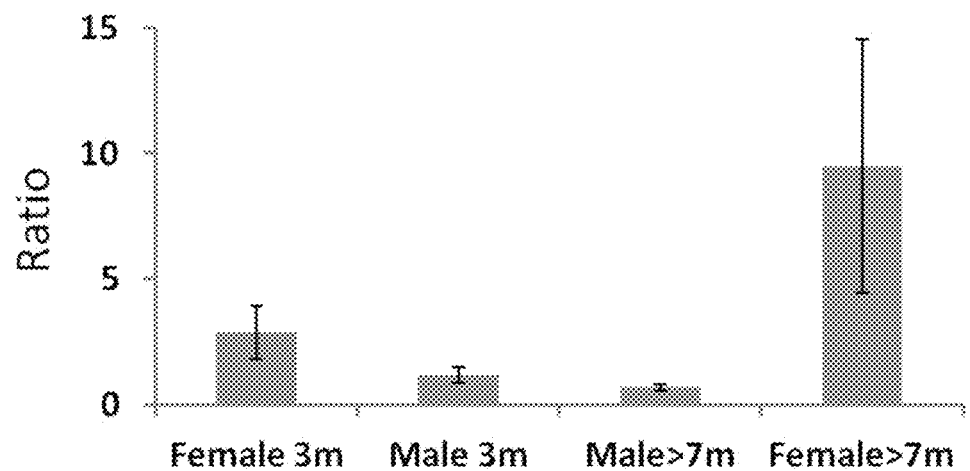
FIGS. 5A-5B show illustrative results from experiments using peptide B (SEQ ID NO: 2; 25-50 µg/injection site) or an adipogenic antibody in a rat dermal skin model of adipogenesis.
Figure 5B:
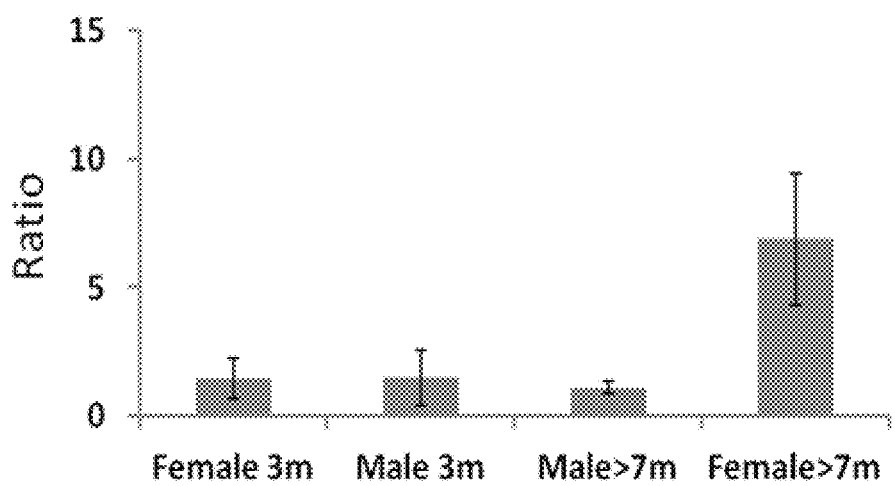
Figure 10:
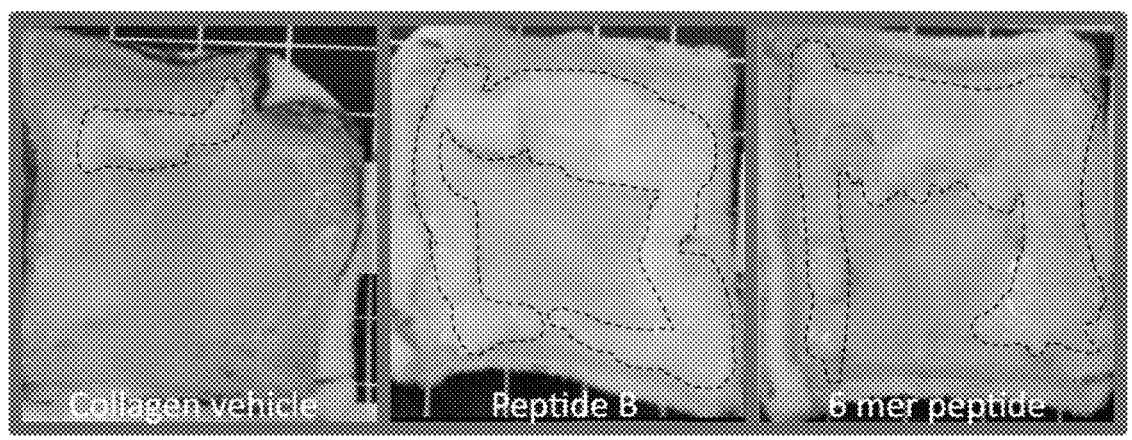
FIG. 10 shows illustrative results of in vivo testing of the 6-mer KSEVSK (SEQ ID NO: 3) for an adipogenic effect.

In vivo, 25-50 μg of peptide B (SEQ ID NO: 2)/injection site in a rat dermal skin model of adipogenesis induced significant fat accumulation (fat pads shown in FIG. 10). There was not an obvious difference between the two types of adipogenic reagents in vivo and both were most effective in old females (see, FIGS. 5A and 5B). In FIGS. 5A and 5B, data are shown as a ratio of the area ("surface area") of fat pads expressed as a ratio of experimental/control values. FIG. 5A shows the effect of the antibody to peptide B and FIG. 5B shows the effect of peptide B.

Figure 6:
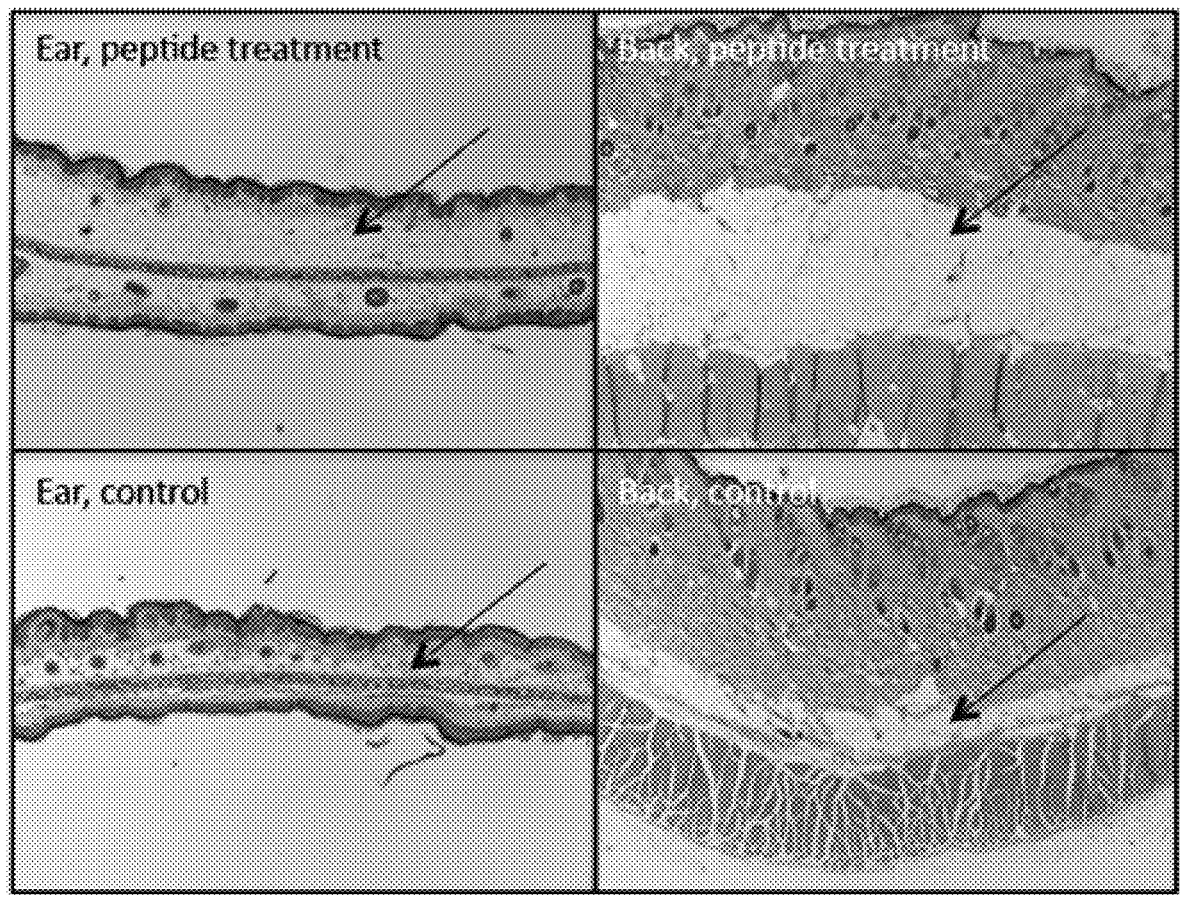
FIG. 6 shows illustrative results of testing of peptide B (SEQ ID NO: 2) in nude guinea pigs. An increase in subcutaneous fat deposition was observed on the upper back of these animals and in the ear fat pad after injection of peptide B in both locations. Arrows point to subcutaneous fat layer.

Peptide B (SEQ ID NO: 2) was also tested for its effect in nude guinea pigs since their skin structure resembles human facial skin. In particular, the skin of this animal model is more similar to human skin than is rat skin, in that it is hairless and the keratinocyte layer is thicker than in the rat model. As shown in FIG. 6, H and E staining revealed an increase in subcutaneous fat deposition was observed on the upper back of these animals and in the ear fat pad after injection of peptide B in both locations (control animals were injected with a collagen gel vehicle only). Thus, peptide B was effective in promoting adipogenesis in this nude guinea pig model.

In order to identify additional adipogenic peptides and to identify the key adipogenic sequences, two approaches were used. In the first, an unbiased screen was performed to identify hyaluronan-binding peptides using 15-mer random phage libraries. Peptide sequences identified in this screen were sorted for: (a) their alignment to the HA binding region of RHAMM, and (b) their lack of alignment to the HA binding region of CD44. Peptide P15-1 was identified in this manner. Peptide P15-1 has the sequence STMMSRSHKTRSHHV (SEQ ID NO: 1).

Figure 8A:
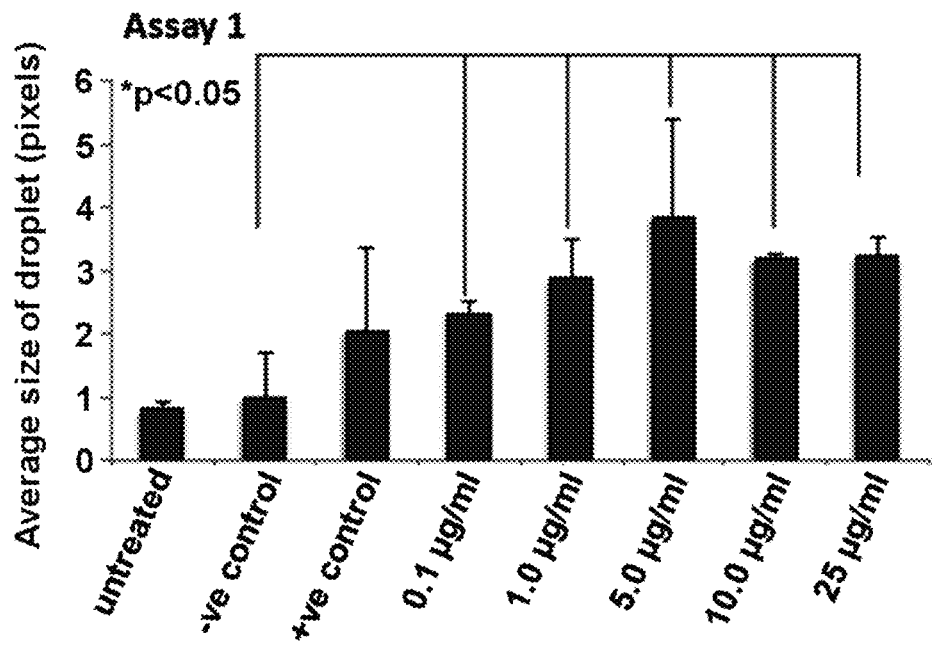
FIGS. 8A and 8B show illustrative dose-response adipogenesis data for the 6-mer peptide KSEVSK (SEQ ID NO: 3).
Figure 8B:
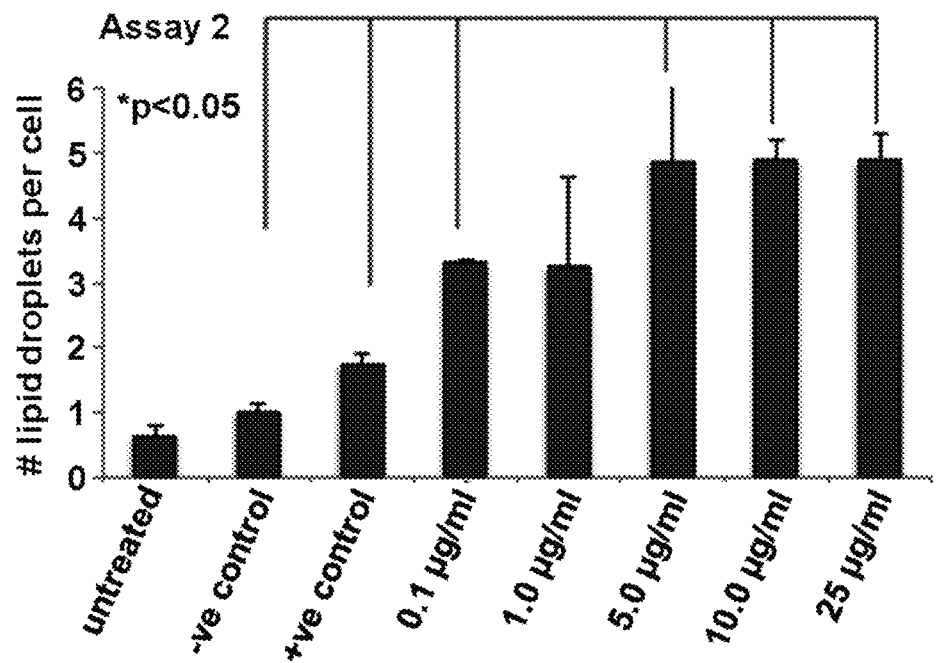
Figure 9:
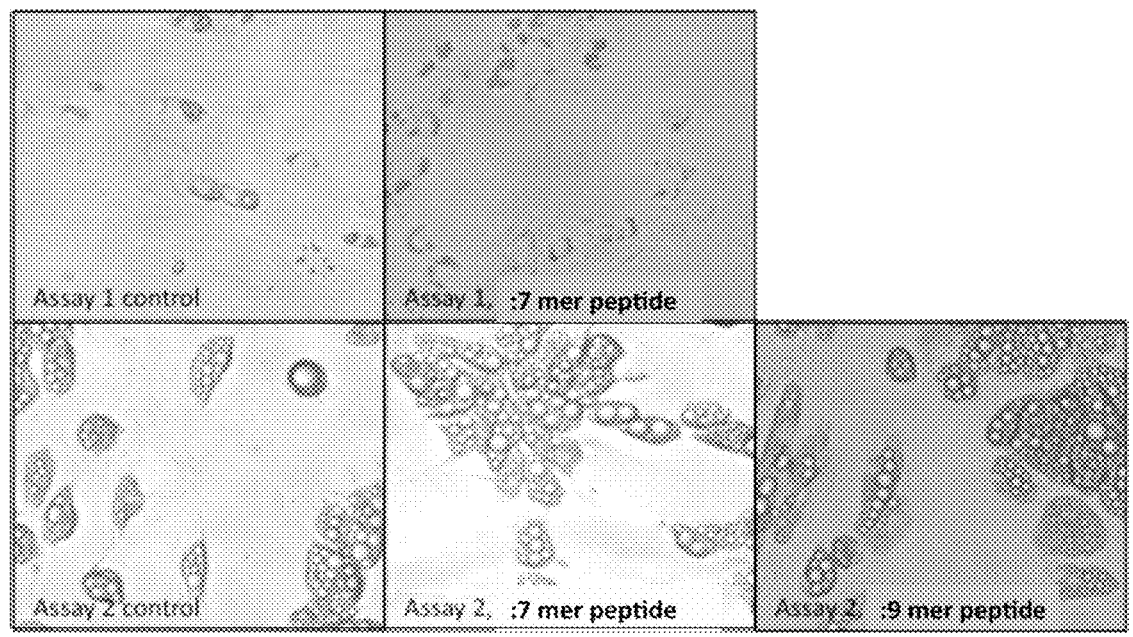
FIG. 9 provides illustrative micrographs showing lipid accumulation in cells in response to treatment with the 9-, 7-, and 6-mers (SEQ ID NOs: 44, 42, and 3, respectively).
Figure 9:
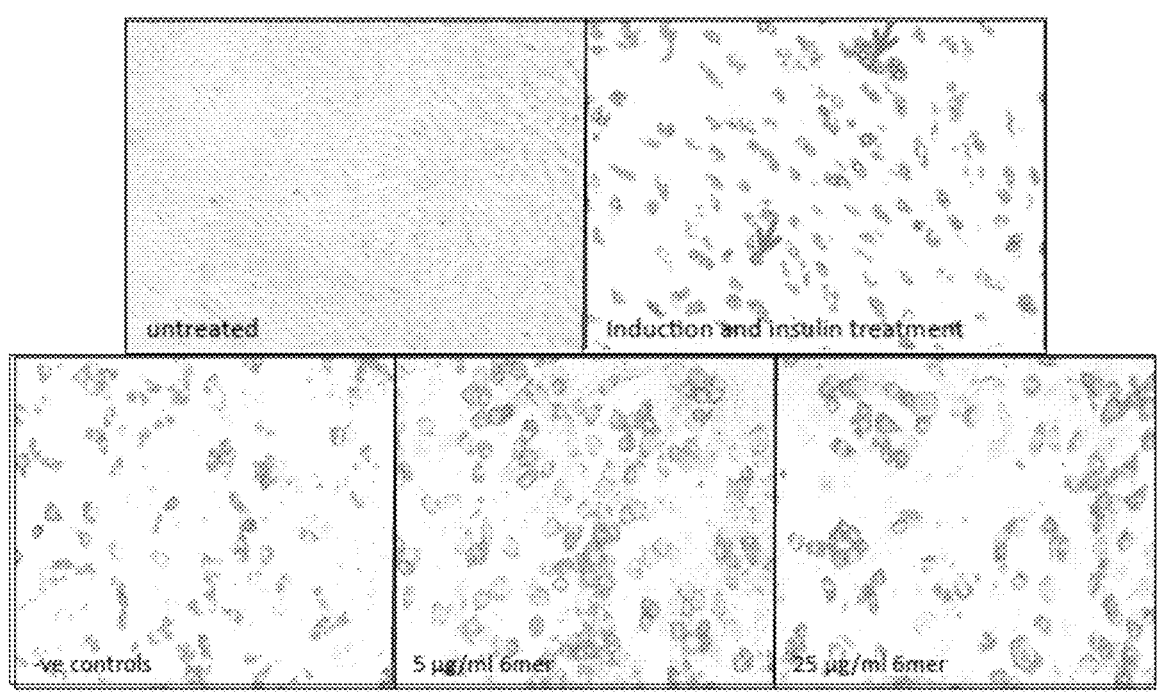

In the second approach, a series of truncations and alanine mutagenesis on peptide B (SEQ ID NO: 2) were performed in order to identify the smallest active sequence. Fragments of peptide B were prepared and assayed for adipogenesis. First, fragments corresponding to the two halves of peptide B were prepared (KLKDENS (SEQ ID NO:93) and SQLKSEVSK (SEQ ID NO: 44)). Only the SQLKSEVSK (SEQ ID NO: 44) fragment was found to be adipogenic. This fragment was then further shortened to LKSEVSK (SEQ ID NO: 42) and KSEVSK (SEQ ID NO: 3), both of which were also found to be adipogenic. Thus, the truncation experiments identified a 9-mer (SQLKSEVSK (SEQ ID NO: 44)), a 7-mer (LKSEVSK (SEQ ID NO: 42)) and a 6-mer (KSEVSK (SEQ ID NO: 3)) that exhibited adipogenic activity (see FIGS. 7, 8, and 9). In FIG. 7, the 7-mer is referred to as Fragment A and the 9-mer is referred to as Fragment C. In FIGS. 8 and 9, "−ve control" refers to the negative control, and "+ve control" refer so the positive control). FIG. 8 shows the adipogenic effects of the 6-mer (KSEVSK (SEQ ID NO: 3)) in assays 1 and 2. In FIG. 9, the upper panel of micrographs shows results from assays 1 and 2, and the lower panel of micrographs shows results from assay 1. In the upper panel of FIG. 9, the panels labeled "control" are a positive control (induction plus insulin). In the lower panel of FIG. 9, the cells in the untreated control were treated only with maintenance medium.

Peptide P15-1 (SEQ ID NO: 1) was also truncated to create a 9-mer having the sequence STMMSRSHK ("Fragment B"; SEQ ID NO: 62). As shown in FIG. 7, this 9-mer also has adipogenic activity.

As shown in FIG. 7, these fragments all had approximately the same adipogenic activity suggesting that the specific activity (activity per weight unit) is highest for the 6-mer KSEVSK (SEQ ID NO: 3). Specific activities (Table 2) were calculated for peptide B (SEQ ID NO: 2) and the 9-mer, 7-mer and 6-mer fragments (SEQ ID NOs: 44, 42, and 3, respectively) using adipogenesis data obtained in assays 1 and 2 as described above, and it was unexpectedly found that the 6-mer had the highest specific activity.

TABLE 2

Specific activity of peptide B and the 9-, 7-, and 6-mers.

| | Molecular weight (daltons) | Fold adipogenic induction vs. negative control | Specific activity (activity/ 1000 daltons) |
|---|---|---|---|
| Assay 1 | | | |
| Peptide B (15mer) (SEQ ID NO: 2) | 1839 | 1.85 | 1.0 |
| 9mer (SEQ ID NO: 44) | 1135 | 2.4 | 2.1 |
| 7mer (SEQ ID NO: 42) | 884 | 2 | 2.3 |
| 6mer (SEQ ID NO: 3) | 753 | 2.8 | 3.7 |
| Assay 2 | | | |
| 15mer (SEQ ID NO: 2) | 1839 | 3.1 | 1.7 |
| 9mer (SEQ ID NO: 44) | 1135 | 3.0 | 2.6 |
| 7mer (SEQ ID NO: 42) | 884 | 3.0 | 3.4 |
| 6mer (SEQ ID NO: 3) | 753 | 4.2 | 5.6 |

These results were surprising and unexpected and show that a shorter peptide is more active than longer peptides. In particular, the increased specific activity of the 6-mer (KSEVSK; SEQ ID NO: 3) as compared to peptide B (SEQ ID NO: 2; a 15-mer) was unexpected, since both the 6-mer and peptide B contain the same number key hyaluronan binding sequences.

The 6-mer (KSEVSK; SEQ ID NO: 3) was tested for adipogenic effect in rat skin in vivo. The results of this testing are shown in the photographs in FIG. 10. The 6-mer is able to induce large fat pads, possibly larger than peptide B.

Figure 11:
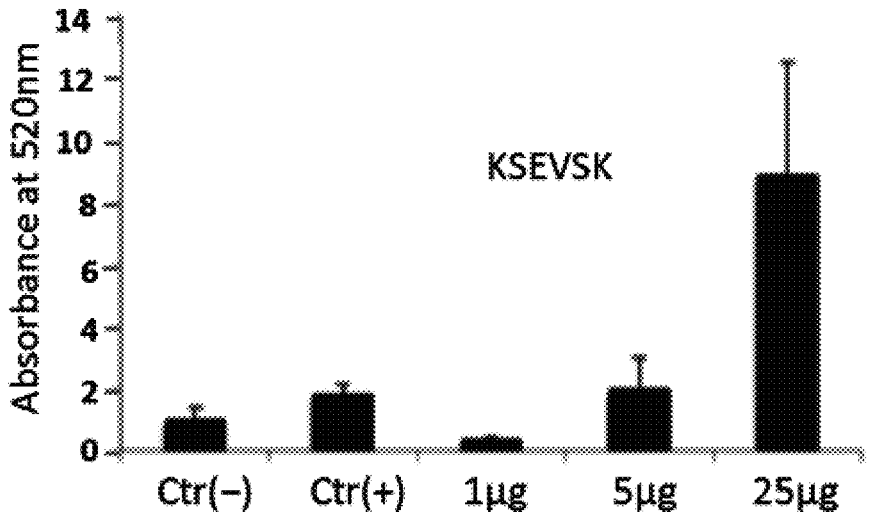
FIGS. 11 and 12 show illustrative adipogenic activity data for peptides in which flanking lysine residues have been mutated to alanine residues (ASEVSK (SEQ ID NO: 38) and KSEVSA (SEQ ID NO: 41)).
Figure 11:
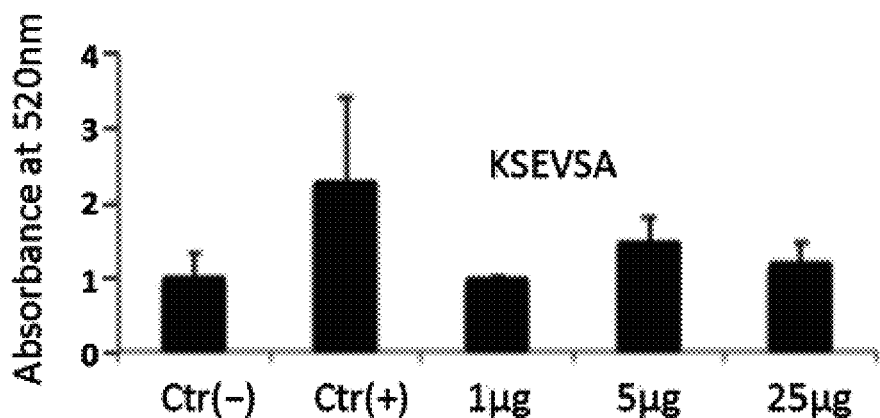
Figure 11:
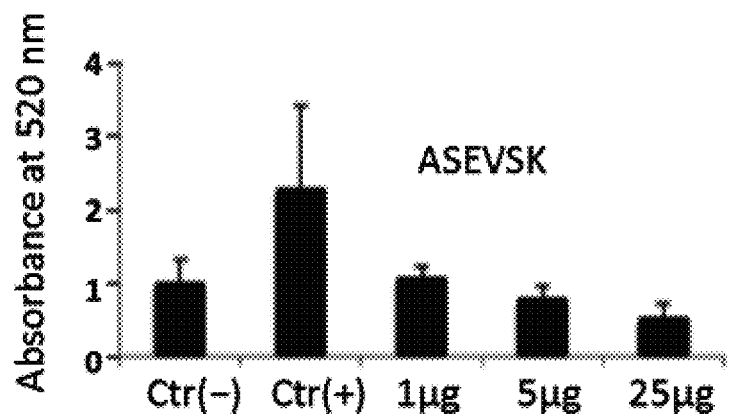
Figure 12:
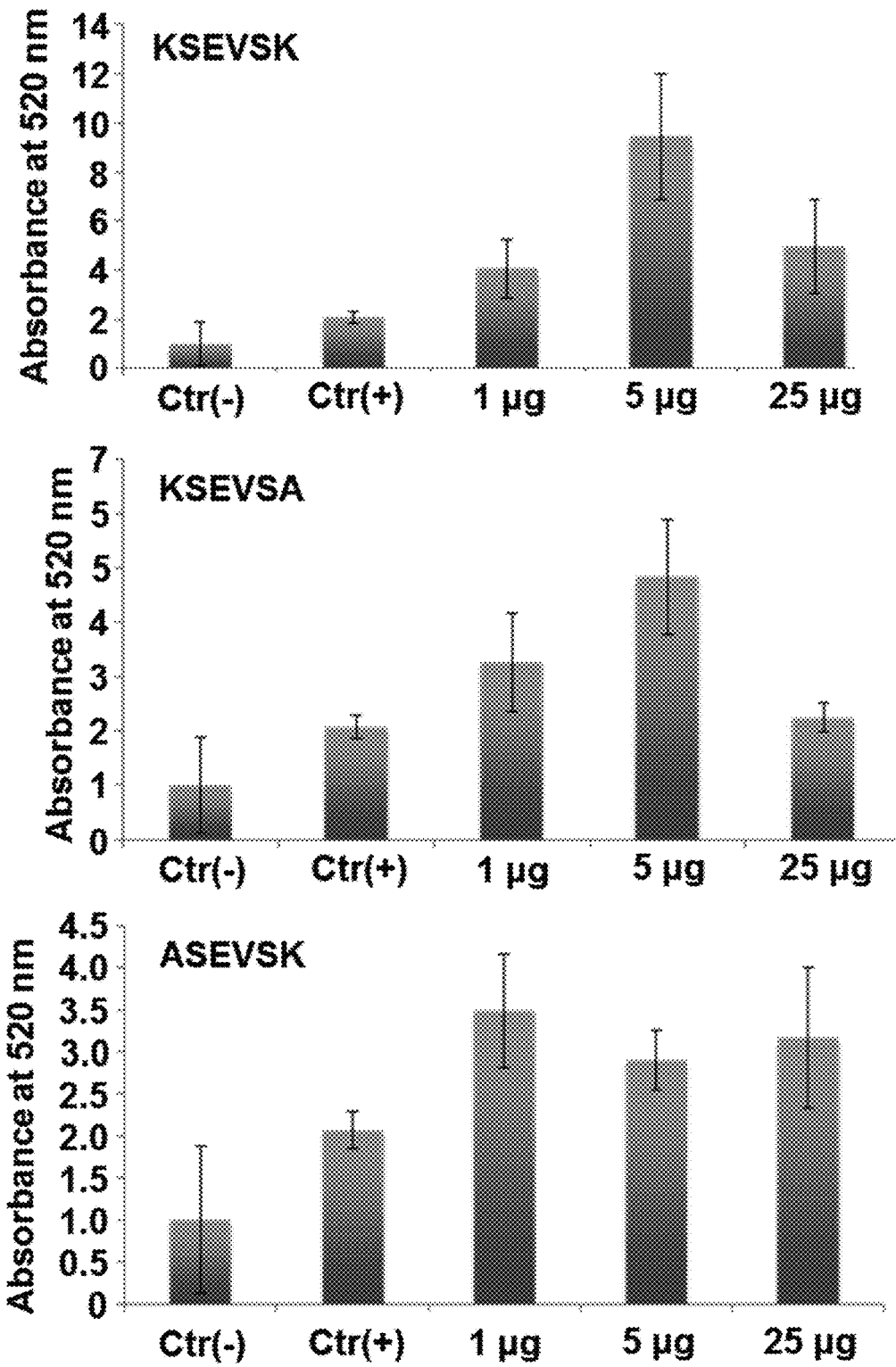

To identify the key amino acids needed for an adipogenic effect, alanine mutagenesis of the 6-mer (KSEVSK; SEQ ID NO: 3) was performed. Since there appears to be a link between hyaluronan binding and adipogenesis and since hyaluronan binding requires basic residues, the flanking lysine (K) residues were first mutated. As shown in FIGS. 11 and 12, the peptides ASEVSK (SEQ ID NO: 38) and KSEVSA (SEQ ID NO: 41) both had reduced adipogenic effects as compared to the KSEVSK (SEQ ID NO: 3) 6-mer when tested using assay 1 (FIG. 11) or assay 2 (FIG. 12).

Figure 13:
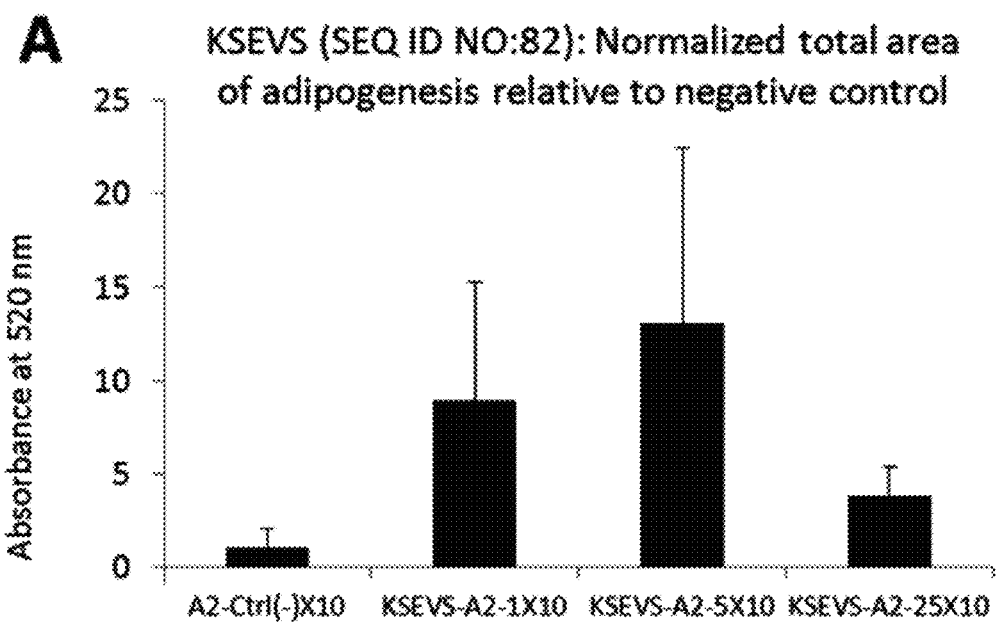
FIGS. 13A and 13B illustrate the adipogenic activity of two five-mer peptides (KSEVS (SEQ ID NO. 82), FIG. 13A) and (SEVSK (SEQ ID NO: 83), FIG. 13B).
Figure 13:
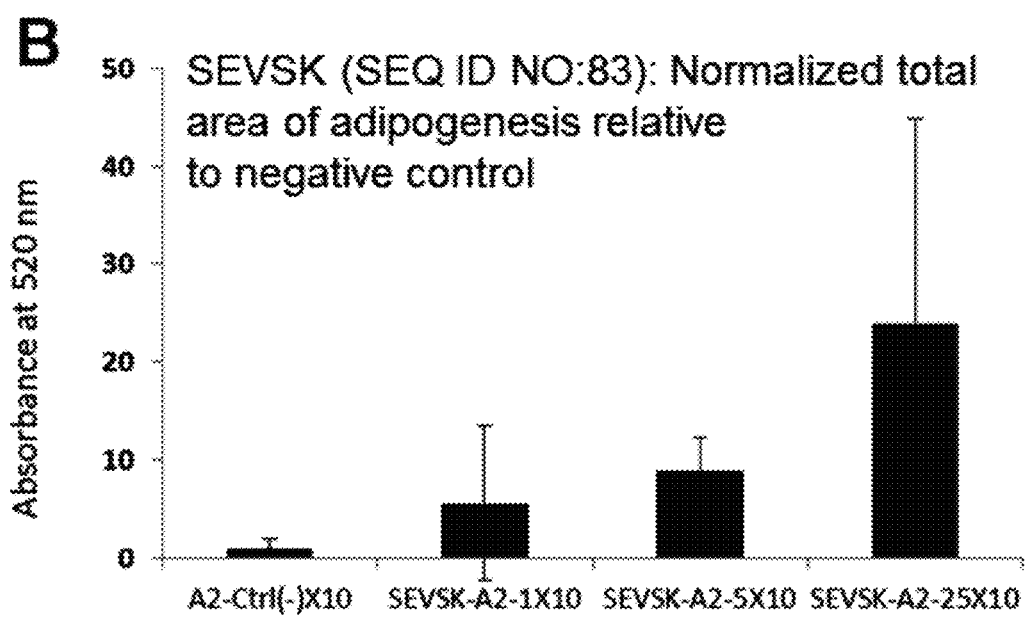

In addition, shorter sequences were also examined and it was discovered that pentamers also exhibited adipogenic activity. Pentamers in which each of the flanking lysine residues were deleted were also synthesized. As shown in FIG. 13, these pentamers (KSEVS (SEQ ID NO. 82) and SEVSK (SEQ ID NO: 83)) were both much less active than the KSEVSK (SEQ ID NO: 3) hexamer, further confirming the importance of the terminal lysine residues. However, both pentamers still exhibited a low level of adipogenic activity (in FIG. 13, A2-Ctrl(−)X10 is the negative control, A2-1X10 is a dose of 1 μg, A2-5X10 is a dose of 5 μg, and A2-25X10 is a dose of 25 μg; y-axes are absorbance at 520 nm).

The results of truncating the KSEVSK (SEQ ID NO: 3) peptide to pentamer peptides and of the alanine mutation experiments show that the loss of the flanking lysine residues reduces but does not ablate adipogenic activity, and indicate that presence of the two lysine residues can produce a peptide that has a high level of adipogenic activity.

To identify a minimal motif sufficient to impart adipogenic activity to a peptide, the KSEVSK (SEQ ID NO: 3) hexamer was used to query the BLAST database to identify evolutionarily conserved sequences in RHAMM proteins from other organisms. The results of this query are shown below in Table 3.

TABLE 3

Evolutionary conservation of the KSEVSK (SEQ ID NO: 3) sequence in RHAMM proteins from various species.

| | | |
|---|---|---|
| Human, mouse, rat, cow, and maccaca | KSEVSK | (SEQ ID NO: 3) |
| Goat | KSEVLK | (SEQ ID NO: 7) |
| Xenopus laevis | KQEVSK | (SEQ ID NO: 4) |
| Ciona intestinalis | KQENTK | (SEQ ID NO: 6) |
| Taeniopygia guttata | KQDVSK | (SEQ ID NO: 8) |

TABLE 3 -continued

Evolutionary conservation of the KSEVSK (SEQ ID NO: 3) sequence in RHAMM proteins from various species.

| | | |
|---|---|---|
| Danio rerio* | KQELDR | (SEQ ID NO: 9) |
| | KQEVDK | (SEQ ID NO: 5) |
| | KQEVSK | (SEQ ID NO: 4) |
| Thermatoga thermerum | LEEIFK | (SEQ ID NO: 10) |
| Thermodesulfovibrio yellowstonii | LSELEK | (SEQ ID NO: 11) |

*The BLAST database includes Danio rerio RHAMM proteins sequences including each of the three listed sequences.

In addition, a BLAST query of the KSEVSK (SEQ ID NO: 3) sequence identified a number of similar sequences found in other proteins linked to both adipogenesis and hyaluronan, for example Sox 2, Sox 21, and upstream binding factor-1. These sequences are shown below in Table 4.

TABLE 4

KSEVSK (SEQ ID NO: 3)-like sequences found in proteins linked to adipogenesis and hyaluronan.

| Sequence (SEQ ID NO) | Source Protein(s) |
|---|---|
| KSEISK (12) | cJnk interacting protein 4 |
| KNEVSK (13) | Salvador homologue 1 |
| KSEVTK (14) | interleukin1 receptor accessory protein |
| KSEVNK (15) | FAM 111B |
| KSDVSK (16) | casp8-associated protein 2 |
| KSQVSK (17) | zinc finger protein 432 |
| SEVSK (83) | myb binding protein 1A, leucine-rich repeat containing protein 16B, TOPB1 interacting check point and replication regulator |
| KSEVS (82) | rho guanine nucleotide exchange factor 5, YLP motif containing 1, ASP, mucin 16 |
| KPEVSK (18) | proline-rich transmembrane protein 2 |
| KSEVGK (19) | cysteine/serine rich nuclear protein 2 |
| KSDSSK (20) | nipped B homologue |
| KSSPSK (21) | nipped B-like protein |
| KSEASK (22) | galanin receptor 1, WD repeating protein, myosine VI |
| KSELRK (23) | amyotrophic lateral sclerosis 2 |
| KCEVSK (24) | titin isoform novex |
| KSKPSK (25) | titin isoform novex |
| KKEVSK (26) | actin binding Rho-activation protein, RFX4, regulator of nonsense transcripts 2 |
| KEEVSK (27) | glucocorticoid-induced transcript 1 |
| KSETSK (28) | ERI1 exoribonuclease family member, tubulin tyrosine ligase |
| KSNVSK (29) | leucine-rich repeat containing protein 8c |
| KDEVSK (30) | trasnlocated promoter region, nuclear basket protein |
| KSEVEK (31) | hect and RLD domain containing E3 ubiquitin ligase |

TABLE 4 -continued

KSEVSK (SEQ ID NO: 3)-like sequences found in proteins linked to adipogenesis and hyaluronan.

| Sequence (SEQ ID NO) | Source Protein(s) |
|---|---|
| KSAVSK (32) | nesprin 1, spectrin repeat containing nuclear envelope 1 |
| KWEVSK (33) | renalase, FAD-dependent amine oxidase |
| KMEVSK (34) | zinc transporter 5 |
| KSEVQK (35) | kinectin 1 |
| KSEVHK (36) | uncharacterized protein C14orf28 |
| KSSVSK (37) | upstream binding transcription factor RNA polymerase, zinc finger and BTB domain containing protein 1 |

The sequences from Tables 3 and 4 were aligned with one another and used to generate the motifs described herein. In view of the diversity of the amino acids at the second, third, fourth, and fifth positions of these sequences, it is expected that alanine mutagenesis at these positions will yield peptides having at least some adipogenic activity. Therefore, in generating the broadest motifs discussed herein, it was assumed that an alanine residue could be present at the second, third, fourth, or fifth position of the peptide.

In addition, as noted above, peptide P15-1 (SEQ ID NO: 1) was truncated to create a 9-mer having the sequence STMMSRSHK ("Fragment B"; SEQ ID NO: 62), and this 9-mer was shown to have adipogenic activity. Alignments of peptide P15-1 with the KSEVSK (SEQ ID NO: 3) hexamer using the COBALT and MUSCLE alignment tools revealed that the sequence KSEVSK aligns with the STMMSR portion of peptide P15-1, as shown below:

```
KSEVSK---------
STMMSRSHKTRSHHV
```

Thus, it is expected that shorter fragments of peptide P15-1 (SEQ ID NO: 1), and in particular the hexamer sequence STMMSR (SEQ ID NO: 51), will also have adipogenic activity. A BLAST query of the STMMSR sequence identified a number of similar sequences found in other proteins linked to both adipogenesis and hyaluronan, for example calcium binding protein 1, ribonuclease P protein, ADP ribosylation factor protein 5, transmembrane protein 236, plasma serine protease inhibitor, CD80, lysophosphatidic acid receptor, plasma serine protease inhibitor, angiopoietin 2, ADP-ribosylation factor binding protein, ubiquitin protein 2, clathrin heavy chain 2, metastasis suppressor protein 1, polycystin 2, and tetratricopeptide repeat protein 17. These sequences are shown below in Table 5.

TABLE 5

STMMSR-like sequences found in proteins linked to adipogenesis and hyaluronan.

| Sequence (SEQ ID NO) | Source Protein(s) |
|---|---|
| SIMMSR (52) | B-cell/CLL lymphoma protein 9 |
| STLMSR (53) | FAM 212B, olfactory receptor 5R1 |

TABLE 5 -continued

STMMSR-like sequences found in proteins linked to adipogenesis and hyaluronan.

| Sequence (SEQ ID NO) | Source Protein(s) |
|---|---|
| STVMSR (54) | dipeptidyl peptidase 4, splicing factor 3B |
| STGLSR (55) | E3 ubiquitin ligase RFWD2 |
| STTMSR (56) | metastasis suppressor 1 |
| STRMSR (57) | E3 ubiquitin ligase, RFWD2 |
| STLMRR (58) | mucin 16 |
| STPVSR (59) | mucin 16 |

The sequences in Table 5 were aligned with one another and with the STMMSR sequence (SEQ ID NO: 51) to generate the motifs described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

When introducing elements of the present invention or the preferred embodiments(s) thereof, the articles "a", "an", "the" and "said" are intended to mean that there are one or more of the elements. The terms "comprising", "comprises", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying figures shall be interpreted as illustrative and not in a limiting sense. All publications, patents, and patent applications cited herein are hereby incorporated by reference in their entirety for all purposes.

What is claimed is:

1. A pharmaceutical or cosmetic composition comprising a pharmaceutically or cosmetically acceptable carrier and a modified peptide or peptidomimetic, wherein the modified peptide or peptidomimetic is at least 6 amino acids in length, but not more than 8 amino acids in length, and comprises a motif having the sequence: KSEVSK (SEQ ID NO: 3), wherein the modified peptide:
  comprises a protecting group, wherein the modified peptide has improved ex vivo and/or in vivo peptide stability and/or improved skin penetration when administered topically, relative to an unmodified peptide of the same sequence; or
  is functionalized with a polymer selected from the group consisting of a polyethylene glycol, a cellulose, and a modified cellulose, wherein the modified peptide has increased bioavailability, relative to an unmodified peptide of the same sequence; and
  wherein the peptidomimetic comprises one or more peptide linkages replaced with a linkage selected from the group consisting of —CH$_2$NH—, —CH$_2$S—, —CH$_2$—CH$_2$—, —CH=CH—, —COCH$_2$—, —CH(OH)CH$_2$—, and —CH$_2$SO, wherein the peptidomimetic has an improvement in a property, relative to an unmodified peptide of the same sequence, wherein the property is selected from the group consisting of: economy of production, chemical stability, half-life, absorption, potency, efficacy, and/or reduced antigenicity.

2. The composition of claim 1, wherein the modified peptide or peptidomimetic is 6 amino acids in length.

3. The composition of claim 1, wherein the composition is for topical, subcutaneous, or transdermal administration.

4. The composition of claim 1, wherein the composition is for injection.

5. The composition of claim 1, wherein the composition further comprises collagen.

6. The composition of claim 5, wherein the collagen is a bovine collagen, a porcine collagen, or a human collagen.

7. The composition of claim 5, wherein the collagen is a synthetic collagen.

8. The composition of claim 1, wherein the composition further comprises an anesthetic.

9. The composition of claim 8, wherein the anesthetic comprises lidocaine.

10. The composition of claim 1, wherein the composition is a skin cream.

11. The composition of claim 1, wherein the modified peptide or peptidomimetic is a modified peptide comprising a protecting group, wherein the modified peptide has improved ex vivo and/or in vivo peptide stability and/or improved skin penetration when administered topically, relative to an unmodified peptide of the same sequence.

12. The composition of claim 11, wherein the protecting group comprises an acetyl group at the amino-terminus of the modified peptide or peptidomimetic.

13. The composition of claim 1, wherein the modified peptide or peptidomimetic is a modified peptide functionalized with a polymer selected from the group consisting of a polyethylene glycol, a cellulose, and a modified cellulose, wherein the modified peptide has increased bioavailability, relative to an unmodified peptide of the same sequence.

14. The composition of claim 1, wherein the modified peptide or peptidomimetic is a peptidomimetic comprising one or more peptide linkages replaced with a linkage selected from the group consisting of —CH$_2$NH—, —CH$_2$S—, —CH$_2$—CH$_2$—, —CH=CH—, —COCH$_2$—, —CH(OH)CH$_2$—, and —CH$_2$SO, wherein the peptidomimetic has an improvement in a property, relative to an unmodified peptide of the same sequence, wherein the property is selected from the group consisting of: economy of production, chemical stability, half-life, absorption, potency, efficacy, and/or reduced antigenicity.

15. A modified peptide or peptidomimetic of at least 6 amino acids in length, but not more than 8 amino acids in length, comprising a motif having the sequence: KSEVSK (SEQ ID NO: 3), wherein the modified peptide:
  comprises a protecting group, wherein the modified peptide has improved ex vivo and/or in vivo peptide stability and/or improved skin penetration when administered topically, relative to an unmodified peptide of the same sequence; or
  is functionalized with a polymer selected from the group consisting of a polyethylene glycol, a cellulose, and a modified cellulose, wherein the modified peptide has increased bioavailability, relative to an unmodified peptide of the same sequence; and
  wherein the peptidomimetic comprises one or more peptide linkages replaced with a linkage selected from the group consisting of —CH$_2$NH—, —CH$_2$S—, —CH$_2$—CH$_2$—, —CH=CH—, —COCH$_2$—, —CH(OH)CH$_2$—, and —CH$_2$SO, wherein the peptidomimetic has an improvement in a property, relative to an unmodified peptide of the same sequence, wherein the property is selected from the group consisting of: economy of production, chemical stability, half-life, absorption, potency, efficacy, and/or reduced antigenicity.

16. The modified peptide or peptidomimetic of claim 15, wherein the modified peptide or peptidomimetic is 6 amino acids in length.

17. The modified peptide or peptidomimetic of claim 15, which is a modified peptide comprising a protecting group, wherein the modified peptide has improved ex vivo and/or in vivo peptide stability and/or improved skin penetration when administered topically, relative to an unmodified peptide of the same sequence.

18. The modified peptide or peptidomimetic of claim 17, wherein the protecting group comprises an acetyl group at the amino-terminus of the peptide or peptidomimetic.

19. The modified peptide or peptidomimetic of claim 15, which is a modified peptide functionalized with a polymer selected from the group consisting of a polyethylene glycol, a cellulose, and a modified cellulose, wherein the modified peptide has increased bioavailability, relative to an unmodified peptide of the same sequence.

20. The modified peptide or peptidomimetic of claim 15, which is a peptidomimetic comprising one or more peptide linkages replaced with a linkage selected from the group consisting of —CH$_2$NH—, —CH$_2$S—, —CH$_2$—CH$_2$—, —CH=CH—, —COCH$_2$—, —CH(OH)CH$_2$—, and —CH$_2$SO, wherein the peptidomimetic has an improvement in a property, relative to an unmodified peptide of the same sequence, wherein the property is selected from the group consisting of: economy of production, chemical stability, half-life, absorption, potency, efficacy, and/or reduced antigenicity.

21. A method of stimulating adipogenesis in a subject, the method comprising administering the composition of claim 1 to the skin of a subject in an amount sufficient to stimulate adipogenesis.

22. The method of claim 21, wherein the skin comprises a burn scar, a surgical scar, an acne scar, a biopsy scar, or scarring produced by an injury.

23. The method of claim 21, wherein the subject is a human.

24. A method of stimulating adipogenesis in a subject, the method comprising administering the composition of claim 1 subcutaneously to a subject in an amount sufficient to stimulate adipogenesis.

25. The method of claim 24, wherein the composition is administered subcutaneously to a lip, an eye lid, a cheek, a forehead, a chin, or a neck.

26. The method of claim 24, wherein the subject is human.

* * * * *

SEQUENCE LISTING

<160> NUMBER OF SEQ ID NOS: 93

<210> SEQ ID NO 1
<211> LENGTH: 15
<212> TYPE: PRT
<213> ORGANISM: Artificial
<220> FEATURE:
<223> OTHER INFORMATION: Synthetic construct

<400> SEQUENCE: 1

Ser Thr Met Met Ser Arg Ser His Lys Thr Arg Ser His His Val
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic construct

<400> SEQUENCE: 2

Lys Leu Lys Asp Glu Asn Ser Gln Leu Lys Ser Glu Val Ser Lys
1               5                   10                  15

<210> SEQ ID NO 3
<211> LENGTH: 6
<212> TYPE: PRT
<213> ORGANISM: Artificial
<220> FEATURE:
<223> OTHER INFORMATION: Synthetic construct

<400> SEQUENCE: 3

Lys Ser Glu Val Ser Lys
1               5

<210> SEQ ID NO 4
<211> LENGTH: 6
<212> TYPE: PRT
<213> ORGANISM: Artificial
<220> FEATURE:
<223> OTHER INFORMATION: Synthetic construct

<400> SEQUENCE: 4

Lys Gln Glu Val Ser Lys
1               5

<210> SEQ ID NO 5
<211> LENGTH: 6
<212> TYPE: PRT
<213> ORGANISM: Artificial
<220> FEATURE:
<223> OTHER INFORMATION: Synthetic construct

<400> SEQUENCE: 5

Lys Gln Glu Val Asp Lys
1               5

<210> SEQ ID NO 6
<211> LENGTH: 6
<212> TYPE: PRT
<213> ORGANISM: Artificial
<220> FEATURE:
<223> OTHER INFORMATION: Synthetic construct

<400> SEQUENCE: 6

Lys Gln Glu Asn Thr Lys
1               5

```
<210> SEQ ID NO 7
<211> LENGTH: 6
<212> TYPE: PRT
<213> ORGANISM: Artificial
<220> FEATURE:
<223> OTHER INFORMATION: Synthetic construct

<400> SEQUENCE: 7

Lys Ser Glu Val Leu Lys
1               5

<210> SEQ ID NO 8
<211> LENGTH: 6
<212> TYPE: PRT
<213> ORGANISM: Artificial
<220> FEATURE:
<223> OTHER INFORMATION: Synthetic construct

<400> SEQUENCE: 8

Lys Gln Asp Val Ser Lys
1               5

<210> SEQ ID NO 9
<211> LENGTH: 6
<212> TYPE: PRT
<213> ORGANISM: Artificial
<220> FEATURE:
<223> OTHER INFORMATION: Synthetic construct

<400> SEQUENCE: 9

Lys Gln Glu Leu Asp Arg
1               5

<210> SEQ ID NO 10
<211> LENGTH: 6
<212> TYPE: PRT
<213> ORGANISM: Artificial
<220> FEATURE:
<223> OTHER INFORMATION: Synthetic construct

<400> SEQUENCE: 10

Leu Glu Glu Ile Phe Lys
1               5

<210> SEQ ID NO 11
<211> LENGTH: 6
<212> TYPE: PRT
<213> ORGANISM: Artificial
<220> FEATURE:
<223> OTHER INFORMATION: Synthetic construct

<400> SEQUENCE: 11

Leu Ser Glu Leu Glu Lys
1               5

<210> SEQ ID NO 12
<211> LENGTH: 6
<212> TYPE: PRT
<213> ORGANISM: Artificial
<220> FEATURE:
<223> OTHER INFORMATION: Synthetic construct

<400> SEQUENCE: 12

Lys Ser Glu Ile Ser Lys
1               5
```

<210> SEQ ID NO 13
<211> LENGTH: 6
<212> TYPE: PRT
<213> ORGANISM: Artificial
<220> FEATURE:
<223> OTHER INFORMATION: Synthetic construct

<400> SEQUENCE: 13

Lys Asn Glu Val Ser Lys
1               5

<210> SEQ ID NO 14
<211> LENGTH: 6
<212> TYPE: PRT
<213> ORGANISM: Artificial
<220> FEATURE:
<223> OTHER INFORMATION: Synthetic construct

<400> SEQUENCE: 14

Lys Ser Glu Val Thr Lys
1               5

<210> SEQ ID NO 15
<211> LENGTH: 6
<212> TYPE: PRT
<213> ORGANISM: Artificial
<220> FEATURE:
<223> OTHER INFORMATION: Synthetic construct

<400> SEQUENCE: 15

Lys Ser Glu Val Asn Lys
1               5

<210> SEQ ID NO 16
<211> LENGTH: 6
<212> TYPE: PRT
<213> ORGANISM: Artificial
<220> FEATURE:
<223> OTHER INFORMATION: Synthetic construct

<400> SEQUENCE: 16

Lys Ser Asp Val Ser Lys
1               5

<210> SEQ ID NO 17
<211> LENGTH: 6
<212> TYPE: PRT
<213> ORGANISM: Artificial
<220> FEATURE:
<223> OTHER INFORMATION: Synthetic construct

<400> SEQUENCE: 17

Lys Ser Gln Val Ser Lys
1               5

<210> SEQ ID NO 18
<211> LENGTH: 6
<212> TYPE: PRT
<213> ORGANISM: Artificial
<220> FEATURE:
<223> OTHER INFORMATION: Synthetic construct

<400> SEQUENCE: 18

Lys Pro Glu Val Ser Lys
1               5

```
<210> SEQ ID NO 19
<211> LENGTH: 6
<212> TYPE: PRT
<213> ORGANISM: Artificial
<220> FEATURE:
<223> OTHER INFORMATION: Synthetic construct

<400> SEQUENCE: 19

Lys Ser Glu Val Gly Lys
1               5

<210> SEQ ID NO 20
<211> LENGTH: 6
<212> TYPE: PRT
<213> ORGANISM: Artificial
<220> FEATURE:
<223> OTHER INFORMATION: Synthetic construct

<400> SEQUENCE: 20

Lys Ser Asp Ser Ser Lys
1               5

<210> SEQ ID NO 21
<211> LENGTH: 6
<212> TYPE: PRT
<213> ORGANISM: Artificial
<220> FEATURE:
<223> OTHER INFORMATION: Synthetic construct

<400> SEQUENCE: 21

Lys Ser Ser Pro Ser Lys
1               5

<210> SEQ ID NO 22
<211> LENGTH: 6
<212> TYPE: PRT
<213> ORGANISM: Artificial
<220> FEATURE:
<223> OTHER INFORMATION: Synthetic construct

<400> SEQUENCE: 22

Lys Ser Glu Ala Ser Lys
1               5

<210> SEQ ID NO 23
<211> LENGTH: 6
<212> TYPE: PRT
<213> ORGANISM: Artificial
<220> FEATURE:
<223> OTHER INFORMATION: Synthetic construct

<400> SEQUENCE: 23

Lys Ser Glu Leu Arg Lys
1               5

<210> SEQ ID NO 24
<211> LENGTH: 6
<212> TYPE: PRT
<213> ORGANISM: Artificial
<220> FEATURE:
<223> OTHER INFORMATION: Synthetic construct

<400> SEQUENCE: 24

Lys Cys Glu Val Ser Lys
1               5

<210> SEQ ID NO 25
```

```
<211> LENGTH: 6
<212> TYPE: PRT
<213> ORGANISM: Artificial
<220> FEATURE:
<223> OTHER INFORMATION: Synthetic construct

<400> SEQUENCE: 25

Lys Ser Lys Pro Ser Lys
1               5

<210> SEQ ID NO 26
<211> LENGTH: 6
<212> TYPE: PRT
<213> ORGANISM: Artificial
<220> FEATURE:
<223> OTHER INFORMATION: Synthetic construct

<400> SEQUENCE: 26

Lys Lys Glu Val Ser Lys
1               5

<210> SEQ ID NO 27
<211> LENGTH: 6
<212> TYPE: PRT
<213> ORGANISM: Artificial
<220> FEATURE:
<223> OTHER INFORMATION: Synthetic construct

<400> SEQUENCE: 27

Lys Glu Glu Val Ser Lys
1               5

<210> SEQ ID NO 28
<211> LENGTH: 6
<212> TYPE: PRT
<213> ORGANISM: Artificial
<220> FEATURE:
<223> OTHER INFORMATION: Synthetic construct

<400> SEQUENCE: 28

Lys Ser Glu Thr Ser Lys
1               5

<210> SEQ ID NO 29
<211> LENGTH: 6
<212> TYPE: PRT
<213> ORGANISM: Artificial
<220> FEATURE:
<223> OTHER INFORMATION: Synthetic construct

<400> SEQUENCE: 29

Lys Ser Asn Val Ser Lys
1               5

<210> SEQ ID NO 30
<211> LENGTH: 6
<212> TYPE: PRT
<213> ORGANISM: Artificial
<220> FEATURE:
<223> OTHER INFORMATION: Synthetic construct

<400> SEQUENCE: 30

Lys Asp Glu Val Ser Lys
1               5

<210> SEQ ID NO 31
<211> LENGTH: 6
```

```
<212> TYPE: PRT
<213> ORGANISM: Artificial
<220> FEATURE:
<223> OTHER INFORMATION: Synthetic construct

<400> SEQUENCE: 31

Lys Ser Glu Val Glu Lys
1               5

<210> SEQ ID NO 32
<211> LENGTH: 6
<212> TYPE: PRT
<213> ORGANISM: Artificial
<220> FEATURE:
<223> OTHER INFORMATION: Synthetic construct

<400> SEQUENCE: 32

Lys Ser Ala Val Ser Lys
1               5

<210> SEQ ID NO 33
<211> LENGTH: 6
<212> TYPE: PRT
<213> ORGANISM: Artificial
<220> FEATURE:
<223> OTHER INFORMATION: Synthetic construct

<400> SEQUENCE: 33

Lys Trp Glu Val Ser Lys
1               5

<210> SEQ ID NO 34
<211> LENGTH: 6
<212> TYPE: PRT
<213> ORGANISM: Artificial
<220> FEATURE:
<223> OTHER INFORMATION: Synthetic construct

<400> SEQUENCE: 34

Lys Met Glu Val Ser Lys
1               5

<210> SEQ ID NO 35
<211> LENGTH: 6
<212> TYPE: PRT
<213> ORGANISM: Artificial
<220> FEATURE:
<223> OTHER INFORMATION: Synthetic construct

<400> SEQUENCE: 35

Lys Ser Glu Val Gln Lys
1               5

<210> SEQ ID NO 36
<211> LENGTH: 6
<212> TYPE: PRT
<213> ORGANISM: Artificial
<220> FEATURE:
<223> OTHER INFORMATION: Synthetic construct

<400> SEQUENCE: 36

Lys Ser Glu Val His Lys
1               5

<210> SEQ ID NO 37
<211> LENGTH: 6
<212> TYPE: PRT
```

```
<213> ORGANISM: Artificial
<220> FEATURE:
<223> OTHER INFORMATION: Synthetic construct

<400> SEQUENCE: 37

Lys Ser Ser Val Ser Lys
1               5

<210> SEQ ID NO 38
<211> LENGTH: 6
<212> TYPE: PRT
<213> ORGANISM: Artificial
<220> FEATURE:
<223> OTHER INFORMATION: Synthetic construct

<400> SEQUENCE: 38

Ala Ser Glu Val Ser Lys
1               5

<210> SEQ ID NO 39
<211> LENGTH: 6
<212> TYPE: PRT
<213> ORGANISM: Artificial
<220> FEATURE:
<223> OTHER INFORMATION: Synthetic construct

<400> SEQUENCE: 39

Lys Ala Glu Val Ser Lys
1               5

<210> SEQ ID NO 40
<211> LENGTH: 6
<212> TYPE: PRT
<213> ORGANISM: Artificial
<220> FEATURE:
<223> OTHER INFORMATION: Synthetic construct

<400> SEQUENCE: 40

Lys Ser Glu Val Ala Lys
1               5

<210> SEQ ID NO 41
<211> LENGTH: 6
<212> TYPE: PRT
<213> ORGANISM: Artificial
<220> FEATURE:
<223> OTHER INFORMATION: Synthetic construct

<400> SEQUENCE: 41

Lys Ser Glu Val Ser Ala
1               5

<210> SEQ ID NO 42
<211> LENGTH: 7
<212> TYPE: PRT
<213> ORGANISM: Artificial
<220> FEATURE:
<223> OTHER INFORMATION: Synthetic construct

<400> SEQUENCE: 42

Leu Lys Ser Glu Val Ser Lys
1               5

<210> SEQ ID NO 43
<211> LENGTH: 8
<212> TYPE: PRT
<213> ORGANISM: Artificial
```

```
<220> FEATURE:
<223> OTHER INFORMATION: Synthetic construct

<400> SEQUENCE: 43

Gln Leu Lys Ser Glu Val Ser Lys
1               5

<210> SEQ ID NO 44
<211> LENGTH: 9
<212> TYPE: PRT
<213> ORGANISM: Artificial
<220> FEATURE:
<223> OTHER INFORMATION: Synthetic construct

<400> SEQUENCE: 44

Ser Gln Leu Lys Ser Glu Val Ser Lys
1               5

<210> SEQ ID NO 45
<211> LENGTH: 10
<212> TYPE: PRT
<213> ORGANISM: Artificial
<220> FEATURE:
<223> OTHER INFORMATION: Synthetic construct

<400> SEQUENCE: 45

Asn Ser Gln Leu Lys Ser Glu Val Ser Lys
1               5                   10

<210> SEQ ID NO 46
<211> LENGTH: 11
<212> TYPE: PRT
<213> ORGANISM: Artificial
<220> FEATURE:
<223> OTHER INFORMATION: Synthetic construct

<400> SEQUENCE: 46

Glu Asn Ser Gln Leu Lys Ser Glu Val Ser Lys
1               5                   10

<210> SEQ ID NO 47
<211> LENGTH: 12
<212> TYPE: PRT
<213> ORGANISM: Artificial
<220> FEATURE:
<223> OTHER INFORMATION: Synthetic construct

<400> SEQUENCE: 47

Asp Glu Asn Ser Gln Leu Lys Ser Glu Val Ser Lys
1               5                   10

<210> SEQ ID NO 48
<211> LENGTH: 13
<212> TYPE: PRT
<213> ORGANISM: Artificial
<220> FEATURE:
<223> OTHER INFORMATION: Synthetic construct

<400> SEQUENCE: 48

Lys Asp Glu Asn Ser Gln Leu Lys Ser Glu Val Ser Lys
1               5                   10

<210> SEQ ID NO 49
<211> LENGTH: 14
<212> TYPE: PRT
<213> ORGANISM: Artificial
<220> FEATURE:
```

<223> OTHER INFORMATION: Synthetic construct

<400> SEQUENCE: 49

Leu Lys Asp Glu Asn Ser Gln Leu Lys Ser Glu Val Ser Lys
1               5                   10

<210> SEQ ID NO 50
<211> LENGTH: 4
<212> TYPE: PRT
<213> ORGANISM: Artificial
<220> FEATURE:
<223> OTHER INFORMATION: Synthetic construct

<400> SEQUENCE: 50

Ser Glu Val Ser
1

<210> SEQ ID NO 51
<211> LENGTH: 6
<212> TYPE: PRT
<213> ORGANISM: Artificial
<220> FEATURE:
<223> OTHER INFORMATION: Synthetic construct

<400> SEQUENCE: 51

Ser Thr Met Met Ser Arg
1               5

<210> SEQ ID NO 52
<211> LENGTH: 6
<212> TYPE: PRT
<213> ORGANISM: Artificial
<220> FEATURE:
<223> OTHER INFORMATION: Synthetic construct

<400> SEQUENCE: 52

Ser Ile Met Met Ser Arg
1               5

<210> SEQ ID NO 53
<211> LENGTH: 6
<212> TYPE: PRT
<213> ORGANISM: Artificial
<220> FEATURE:
<223> OTHER INFORMATION: Synthetic construct

<400> SEQUENCE: 53

Ser Thr Leu Met Ser Arg
1               5

<210> SEQ ID NO 54
<211> LENGTH: 6
<212> TYPE: PRT
<213> ORGANISM: Artificial
<220> FEATURE:
<223> OTHER INFORMATION: Synthetic construct

<400> SEQUENCE: 54

Ser Thr Val Met Ser Arg
1               5

<210> SEQ ID NO 55
<211> LENGTH: 6
<212> TYPE: PRT
<213> ORGANISM: Artificial
<220> FEATURE:
<223> OTHER INFORMATION: Synthetic construct

```
<400> SEQUENCE: 55

Ser Thr Gly Leu Ser Arg
1               5

<210> SEQ ID NO 56
<211> LENGTH: 6
<212> TYPE: PRT
<213> ORGANISM: Artificial
<220> FEATURE:
<223> OTHER INFORMATION: Synthetic construct

<400> SEQUENCE: 56

Ser Thr Thr Met Ser Arg
1               5

<210> SEQ ID NO 57
<211> LENGTH: 6
<212> TYPE: PRT
<213> ORGANISM: Artificial
<220> FEATURE:
<223> OTHER INFORMATION: Synthetic construct

<400> SEQUENCE: 57

Ser Thr Arg Met Ser Arg
1               5

<210> SEQ ID NO 58
<211> LENGTH: 6
<212> TYPE: PRT
<213> ORGANISM: Artificial
<220> FEATURE:
<223> OTHER INFORMATION: Synthetic construct

<400> SEQUENCE: 58

Ser Thr Leu Met Arg Arg
1               5

<210> SEQ ID NO 59
<211> LENGTH: 6
<212> TYPE: PRT
<213> ORGANISM: Artificial
<220> FEATURE:
<223> OTHER INFORMATION: Synthetic construct

<400> SEQUENCE: 59

Ser Thr Pro Val Ser Arg
1               5

<210> SEQ ID NO 60
<211> LENGTH: 7
<212> TYPE: PRT
<213> ORGANISM: Artificial
<220> FEATURE:
<223> OTHER INFORMATION: Synthetic construct

<400> SEQUENCE: 60

Ser Thr Met Met Ser Arg Ser
1               5

<210> SEQ ID NO 61
<211> LENGTH: 8
<212> TYPE: PRT
<213> ORGANISM: Artificial
<220> FEATURE:
<223> OTHER INFORMATION: Synthetic construct
```

```
<400> SEQUENCE: 61

Ser Thr Met Met Ser Arg Ser His
1               5

<210> SEQ ID NO 62
<211> LENGTH: 9
<212> TYPE: PRT
<213> ORGANISM: Artificial
<220> FEATURE:
<223> OTHER INFORMATION: Synthetic construct

<400> SEQUENCE: 62

Ser Thr Met Met Ser Arg Ser His Lys
1               5

<210> SEQ ID NO 63
<211> LENGTH: 10
<212> TYPE: PRT
<213> ORGANISM: Artificial
<220> FEATURE:
<223> OTHER INFORMATION: Synthetic construct

<400> SEQUENCE: 63

Ser Thr Met Met Ser Arg Ser His Lys Thr
1               5                   10

<210> SEQ ID NO 64
<211> LENGTH: 11
<212> TYPE: PRT
<213> ORGANISM: Artificial
<220> FEATURE:
<223> OTHER INFORMATION: Synthetic construct

<400> SEQUENCE: 64

Ser Thr Met Met Ser Arg Ser His Lys Thr Arg
1               5                   10

<210> SEQ ID NO 65
<211> LENGTH: 12
<212> TYPE: PRT
<213> ORGANISM: Artificial
<220> FEATURE:
<223> OTHER INFORMATION: Synthetic construct

<400> SEQUENCE: 65

Ser Thr Met Met Ser Arg Ser His Lys Thr Arg Ser
1               5                   10

<210> SEQ ID NO 66
<211> LENGTH: 13
<212> TYPE: PRT
<213> ORGANISM: Artificial
<220> FEATURE:
<223> OTHER INFORMATION: Synthetic construct

<400> SEQUENCE: 66

Ser Thr Met Met Ser Arg Ser His Lys Thr Arg Ser His
1               5                   10

<210> SEQ ID NO 67
<211> LENGTH: 4
<212> TYPE: PRT
<213> ORGANISM: Artificial
<220> FEATURE:
<223> OTHER INFORMATION: Synthetic construct

<400> SEQUENCE: 67
```

Thr Met Met Ser
1

<210> SEQ ID NO 68
<211> LENGTH: 4
<212> TYPE: PRT
<213> ORGANISM: Artificial
<220> FEATURE:
<223> OTHER INFORMATION: Synthetic construct

<400> SEQUENCE: 68

Thr Met Ala Gln
1

<210> SEQ ID NO 69
<211> LENGTH: 4
<212> TYPE: PRT
<213> ORGANISM: Artificial
<220> FEATURE:
<223> OTHER INFORMATION: Synthetic construct

<400> SEQUENCE: 69

Thr Arg Met Trp
1

<210> SEQ ID NO 70
<211> LENGTH: 4
<212> TYPE: PRT
<213> ORGANISM: Artificial
<220> FEATURE:
<223> OTHER INFORMATION: Synthetic construct

<400> SEQUENCE: 70

Thr Val Leu Ser
1

<210> SEQ ID NO 71
<211> LENGTH: 4
<212> TYPE: PRT
<213> ORGANISM: Artificial
<220> FEATURE:
<223> OTHER INFORMATION: Synthetic construct

<400> SEQUENCE: 71

Ile Gly Met Ser
1

<210> SEQ ID NO 72
<211> LENGTH: 4
<212> TYPE: PRT
<213> ORGANISM: Artificial
<220> FEATURE:
<223> OTHER INFORMATION: Synthetic construct

<400> SEQUENCE: 72

Lys Met Thr Ser
1

<210> SEQ ID NO 73
<211> LENGTH: 8
<212> TYPE: PRT
<213> ORGANISM: Artificial
<220> FEATURE:
<223> OTHER INFORMATION: Synthetic construct

<400> SEQUENCE: 73

```
Thr Met Met Ala Ala Ala Ala Ser
1               5

<210> SEQ ID NO 74
<211> LENGTH: 8
<212> TYPE: PRT
<213> ORGANISM: Artificial
<220> FEATURE:
<223> OTHER INFORMATION: Synthetic construct

<400> SEQUENCE: 74

Thr Ala Ala Met Met Ser Ala Ala
1               5

<210> SEQ ID NO 75
<211> LENGTH: 8
<212> TYPE: PRT
<213> ORGANISM: Artificial
<220> FEATURE:
<223> OTHER INFORMATION: Synthetic construct

<400> SEQUENCE: 75

Thr Met Ala Ala Ala Met Ala Ser
1               5

<210> SEQ ID NO 76
<211> LENGTH: 6
<212> TYPE: PRT
<213> ORGANISM: Artificial
<220> FEATURE:
<223> OTHER INFORMATION: Synthetic construct

<400> SEQUENCE: 76

Thr Leu Leu Met Met Thr
1               5

<210> SEQ ID NO 77
<211> LENGTH: 6
<212> TYPE: PRT
<213> ORGANISM: Artificial
<220> FEATURE:
<223> OTHER INFORMATION: Synthetic construct

<400> SEQUENCE: 77

Ala Met Leu Ile Met Ser
1               5

<210> SEQ ID NO 78
<211> LENGTH: 4
<212> TYPE: PRT
<213> ORGANISM: Artificial
<220> FEATURE:
<223> OTHER INFORMATION: Synthetic construct

<400> SEQUENCE: 78

Thr Ala Ala Met
1

<210> SEQ ID NO 79
<211> LENGTH: 4
<212> TYPE: PRT
<213> ORGANISM: Artificial
<220> FEATURE:
<223> OTHER INFORMATION: Synthetic construct

<400> SEQUENCE: 79

Phe Thr Met Ala
```

```
<210> SEQ ID NO 80
<211> LENGTH: 5
<212> TYPE: PRT
<213> ORGANISM: Artificial
<220> FEATURE:
<223> OTHER INFORMATION: Synthetic construct

<400> SEQUENCE: 80

Thr Cys Cys Arg Ser
1               5

<210> SEQ ID NO 81
<211> LENGTH: 5
<212> TYPE: PRT
<213> ORGANISM: Artificial
<220> FEATURE:
<223> OTHER INFORMATION: Synthetic construct

<400> SEQUENCE: 81

Thr Leu Ala Leu Met
1               5

<210> SEQ ID NO 82
<211> LENGTH: 5
<212> TYPE: PRT
<213> ORGANISM: Artificial
<220> FEATURE:
<223> OTHER INFORMATION: Synthetic construct

<400> SEQUENCE: 82

Lys Ser Glu Val Ser
1               5

<210> SEQ ID NO 83
<211> LENGTH: 5
<212> TYPE: PRT
<213> ORGANISM: Artificial
<220> FEATURE:
<223> OTHER INFORMATION: Synthetic construct

<400> SEQUENCE: 83

Ser Glu Val Ser Lys
1               5

<210> SEQ ID NO 84
<211> LENGTH: 6
<212> TYPE: PRT
<213> ORGANISM: Artificial
<220> FEATURE:
<223> OTHER INFORMATION: Synthetic construct

<400> SEQUENCE: 84

Arg Gln Lys Val Leu Lys
1               5

<210> SEQ ID NO 85
<211> LENGTH: 6
<212> TYPE: PRT
<213> ORGANISM: Artificial
<220> FEATURE:
<223> OTHER INFORMATION: Synthetic construct

<400> SEQUENCE: 85

Leu Gln Ala Thr Gln Lys
1               5
```

<210> SEQ ID NO 86
<211> LENGTH: 6
<212> TYPE: PRT
<213> ORGANISM: Artificial
<220> FEATURE:
<223> OTHER INFORMATION: Synthetic construct

<400> SEQUENCE: 86

Gln Leu Val Lys Arg Lys
1               5

<210> SEQ ID NO 87
<211> LENGTH: 6
<212> TYPE: PRT
<213> ORGANISM: Artificial
<220> FEATURE:
<223> OTHER INFORMATION: Synthetic construct

<400> SEQUENCE: 87

Gln Lys Val Leu Lys Arg
1               5

<210> SEQ ID NO 88
<211> LENGTH: 6
<212> TYPE: PRT
<213> ORGANISM: Artificial
<220> FEATURE:
<223> OTHER INFORMATION: Synthetic construct

<400> SEQUENCE: 88

Gly Gly Arg Gly Arg Arg
1               5

<210> SEQ ID NO 89
<211> LENGTH: 6
<212> TYPE: PRT
<213> ORGANISM: Artificial
<220> FEATURE:
<223> OTHER INFORMATION: Synthetic construct

<400> SEQUENCE: 89

Gly Gly Arg Gly Gly Arg
1               5

<210> SEQ ID NO 90
<211> LENGTH: 6
<212> TYPE: PRT
<213> ORGANISM: Artificial
<220> FEATURE:
<223> OTHER INFORMATION: Synthetic construct

<400> SEQUENCE: 90

Gly Gly Gly Gly Gly Arg
1               5

<210> SEQ ID NO 91
<211> LENGTH: 114
<212> TYPE: PRT
<213> ORGANISM: Artificial
<220> FEATURE:
<223> OTHER INFORMATION: Synthetic construct

<400> SEQUENCE: 91

Leu Asp Ala Phe Glu Ala Glu Lys Gln Ala Leu Leu Asn Glu His Gly
1               5                   10                  15

```
Ala Thr Gln Glu Gln Leu Asn Lys Ile Arg Asp Ser Tyr Ala Gln Leu
            20                  25                  30

Leu Gly His Gln Asn Leu Lys Gln Lys Ile Lys His Val Val Lys Leu
        35                  40                  45

Lys Asp Glu Asn Ser Gln Leu Lys Ser Glu Val Ser Lys Leu Arg Ser
    50                  55                  60

Gln Leu Val Lys Arg Lys Gln Asn Glu Leu Arg Leu Gln Gly Glu Leu
65                  70                  75                  80

Asp Lys Ala Leu Gly Ile Arg His Phe Asp Pro Ser Lys Ala Phe Cys
            85                  90                  95

His Ala Ser Lys Glu Asn Phe Thr Pro Leu Lys Glu Gly Asn Pro Asn
            100                 105                 110

Cys Cys

<210> SEQ ID NO 92
<211> LENGTH: 32
<212> TYPE: PRT
<213> ORGANISM: Artificial
<220> FEATURE:
<223> OTHER INFORMATION: Synthetic construct

<400> SEQUENCE: 92

Leu Lys Gln Lys Ile Lys His Val Val Lys Leu Lys Asp Glu Asn Ser
1               5                   10                  15

Gln Leu Lys Ser Glu Val Ser Lys Leu Arg Ser Gln Leu Val Lys Arg
            20                  25                  30

<210> SEQ ID NO 93
<211> LENGTH: 7
<212> TYPE: PRT
<213> ORGANISM: Artificial
<220> FEATURE:
<223> OTHER INFORMATION: Synthetic construct

<400> SEQUENCE: 93

Lys Leu Lys Asp Glu Asn Ser
1               5
```